(12) United States Patent
Freel Meyers et al.

(10) Patent No.: US 8,772,268 B2
(45) Date of Patent: Jul. 8, 2014

(54) BISPHOSPHONAMIDATE PRODRUGS AND USES THEREOF

(75) Inventors: Caren Laura Freel Meyers, Baltimore, MD (US); Marie Webster, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/695,018

(22) PCT Filed: Apr. 27, 2011

(86) PCT No.: PCT/US2011/034189
§ 371 (c)(1),
(2), (4) Date: Oct. 26, 2012

(87) PCT Pub. No.: WO2011/139791
PCT Pub. Date: Nov. 10, 2011

(65) Prior Publication Data
US 2013/0090311 A1    Apr. 11, 2013

Related U.S. Application Data

(60) Provisional application No. 61/328,466, filed on Apr. 27, 2010.

(51) Int. Cl.
*C07F 9/6574* (2006.01)
*C07F 9/44* (2006.01)

(52) U.S. Cl.
USPC ............. 514/94; 514/107; 514/108; 514/105; 548/112; 558/157; 558/84

(58) Field of Classification Search
USPC ............. 558/84, 157; 514/94, 107, 108, 105; 548/112
See application file for complete search history.

(56) References Cited

PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Barney et al., Bioorg. Med. Chem., vol. 18, No. 20, pp. 7212-7220, 2010.*
Boissier et al., Cancer Res., vol. 57, No. 18, pp. 3890-3894, 1997.*
Boucher and Doolittle, Mol. Microbiol., vol. 37, No. 4, pp. 703-716, 2000.*
Boyd et al., in Cytotoxic Anticancer Drugs: Models and Concepts for Drug Discovery and Development; Eds., Kluwer Academic: Hingham, MA, p. 11, 1992.*
Cox et al., Chem. Rev., vol. 64, No. 4, pp. 317-352, 1964.*
Croucher et al., J. Bone Miner. Res., vol. 18, No. 3, pp. 482-492, 2003.*
Desjardins et al., Antimicrob. Agents Chemother., vol. 16, No. 6, p. 710-718, 1979.*
Domcheck et al., Cancer, vol. 89, No. 2, pp. 363-368, 2000.*
Frith et al., J. Bone Miner. Res., vol. 12, No. 9, pp. 1358-1367, 1997.*
Gnant et al., Curr. Cancer Drug Targets, vol. 9, pp. 824-833, 2009.*
Hamma-Kourbali et al., Biochem. Biophys. Res. Commun., vol. 310, No. 3, pp. 816-823, 2003.*
Knight et al., Anti-Cancer Drugs, vol. 16, No. 9, pp. 969-976, 2005.*
Lehenkari et al., Mol. Pharmacol., vol. 62, pp. 1255-1262, 2002.*
Li et al., Lung Cancer, vol. 59, No. 2, pp. 180-191, 2008.*
Lipton et al., Cancer Treatment Reviews, vol. 34, pp. S25-S30, 2008.*
Matsumoto et al., Lung Cancer, vol. 47, No. 1, pp. 31-39, 2005.*
Meyers et al., Org. Lett., vol. 3, No. 23, pp. 3765-3768, 2001.*
Milhous et al., Antimicrob. Agents Chemother., vol. 27, No. 4, pp. 525-530, 1985.*
Mönkkönen et al., Anti-Cancer Drugs, vol. 19, No. 4, pp. 391-399, 2008.*
Monks et al., JNCI, J. Natl. Cancer Inst., vol. 83, No. 11, pp. 757-766, 1991.*
Morgan et al., Seminars in Oncology, vol. 37, No. 5, pp. S30-S40, 2010.*
Posner et al. Tetrahedron, vol. 53, No. 1, pp. 37-50, 1997.*
Röaikköönen et al., Biochem. Biophys. Res. Commun., Mar. 2011, vol. 407, pp. 663-667.*
Rogers et al., Biochem. J., vol. 303, pp. 303-311, 1994.*
Russell et al., Osteoporosis Int., vol. 19, No. 6, pp. 733-759, 2008.*
Santini et al., Clin. Cancer Res., vol. 13, No. 15, pp. 4482-4486, 2007.*
Shull et al., Bioorg. Med. Chem., vol. 14, No. 12, pp. 4130-4136, 2006.*
Sillero et al., FEBS Letters, vol. 580, No. 24, pp. 5723-5727, 2006.*
Szabo et al., J. Med. Chem., vol. 45, No. 11, pp. 2185-2196, 2002.*
Vepsäläinen et al., "Bisphosphanate Prodrugs," Curr. Med. Chem., vol. 9, pp. 1201-1208, 2002.*
Wiemer et al., Bioorg. Med. Chem. vol. 16, No. 7, pp. 3652-3660, 2008.*
Wood et al., J. Pharmacol. Exp. Ther., vol. 302, No. 3, pp. 1055-1061, 2002.*
Zhang et al., J. Med. Chem., vol. 49, No. 19, pp. 5804-5814, 2006.*
Wiemer et al., Biochem. Biophys. Res. Commun., vol. 353, pp. 921-925, 2007.*
Nakatsu et al., Microvasc. Res., vol. 66, pp. 102-112, 2003.*
Hecker et al., "Prodrugs of Phosphates and Phosphonates," Journal of Medicinal Chemistry, vol. 51, No. 8, pp. 2328-2345, 2008.
Tobias, "Synthesis and Biological Studies of Novel Nucleoside Phosphoramidate Prodrugs," Journal of Medicinal Chemistry, vol. 44, No. 25, pp. 4475-4480, 2001.

(Continued)

*Primary Examiner* — Kristin Vajda
(74) *Attorney, Agent, or Firm* — Venable LLP; Keith G. Haddaway; Lars H. Genieser

(57) ABSTRACT

Bisphosphonamidate prodrugs of therapeutic bisphosphonate compounds and uses thereof to treat diseases are described.

45 Claims, 28 Drawing Sheets

(56) References Cited

PUBLICATIONS

Wu et al., "Synthesis and Biological Activity of a Gemcitabine Phosphoramidate Prodrug," Journal of Medicinal Chemistry, vol. 50, No. 15, pp. 3743-3746, 2007.

Schultz, "Prodrugs of Biologically Active Phosphate Esters," Bioorganic and Medicinal Chemistry, vol. 11, pp. 885-898, 2003.

Ahlmark et al., "Bisphosphonate Prodrugs: Synthesis and in Vitro Evaluation of Novel Clodronic Acid Dianhydrides as Bioreversible Prodrugs of Clondonate," Journal of Medicinal Chemistry, vol. 42, No. 8, pp. 1473-1476, 1999.

Niemi et al., "Bisphosphonate prodrugs: synthesis and in vitro evaluation of alkyl and acyloxymethyl esters of etidronic acid as bioreversible prodrugs of etidronate," European Journal of Pharmaceutical Sciences, vol. 11, pp. 173-180, 2000.

International Search Report issued in International Application No. PCT/US2011/034189 dated Jan. 19, 2012.

Written Opinion issued in International Application No. PCT/US2011/034189 dated Jan. 19, 2012.

Boissier et al., *Cancer Res.*, vol. 60, pp. 2949-2954 (2000).

\* cited by examiner

6A

6B

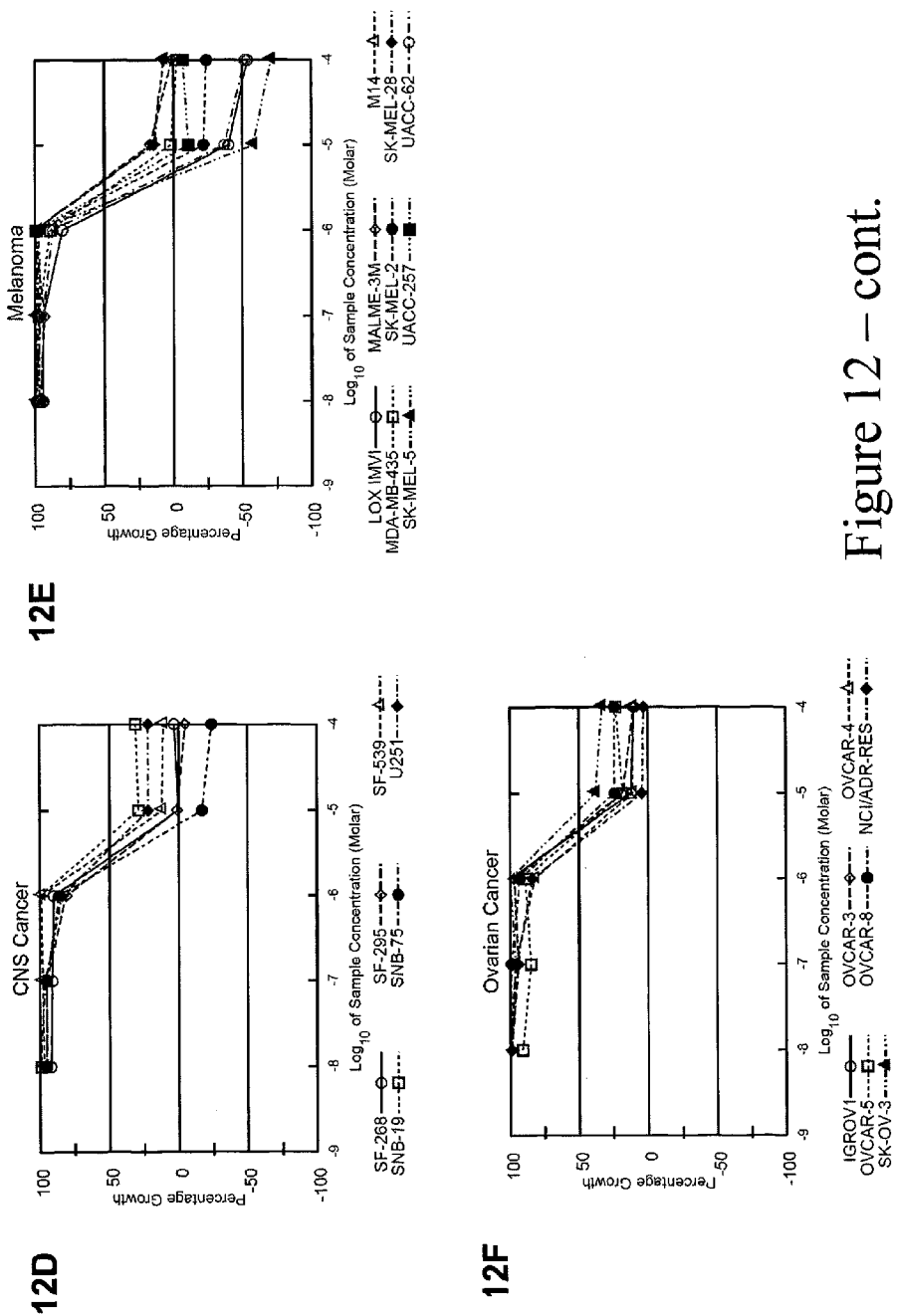
Figure 12 – cont.

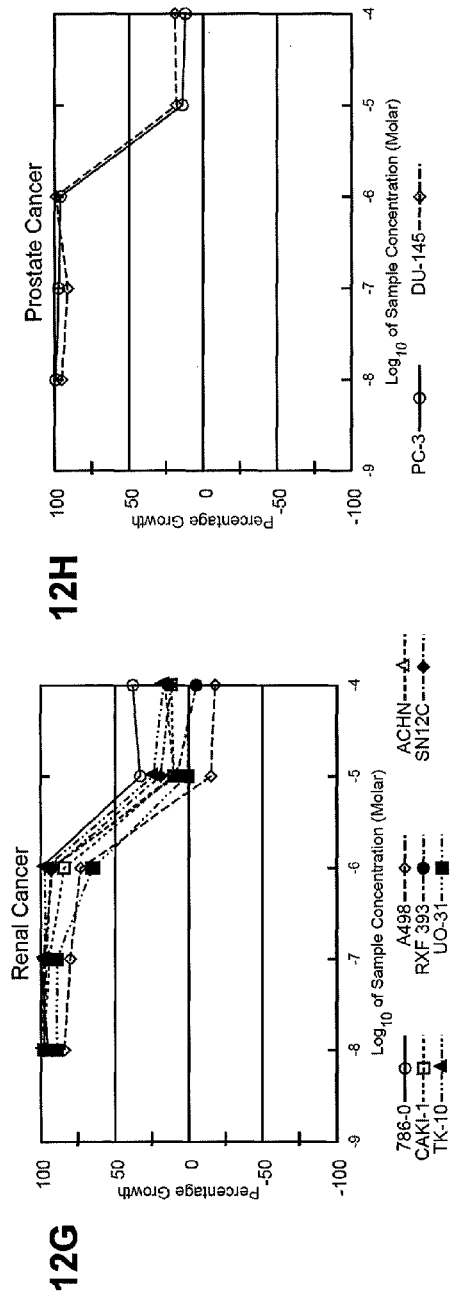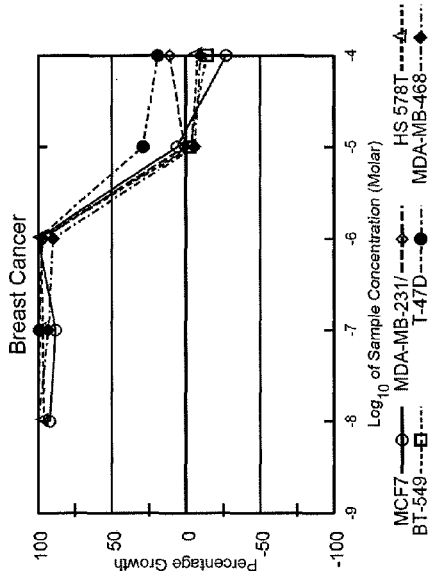
Figure 12 – cont.

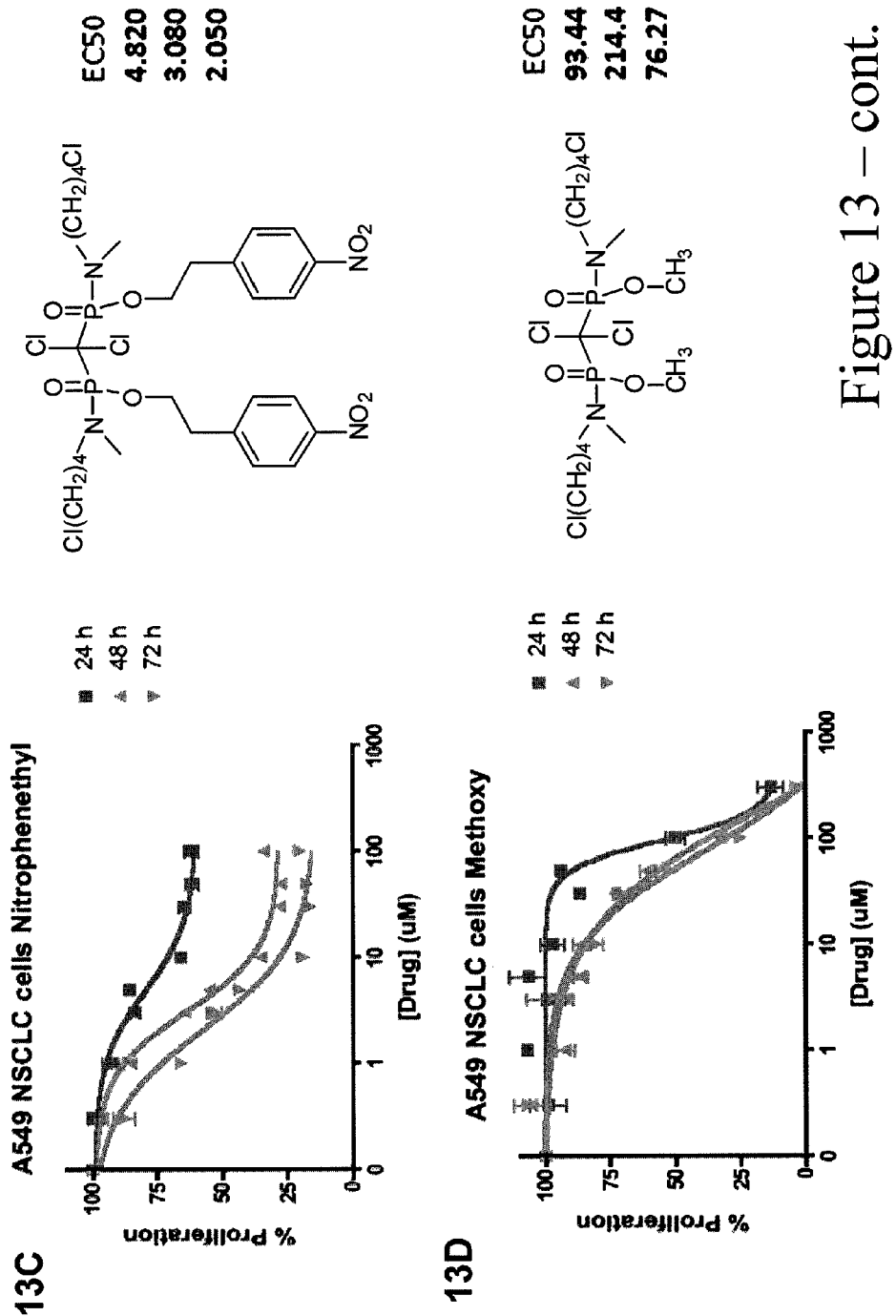
Figure 13 – cont.

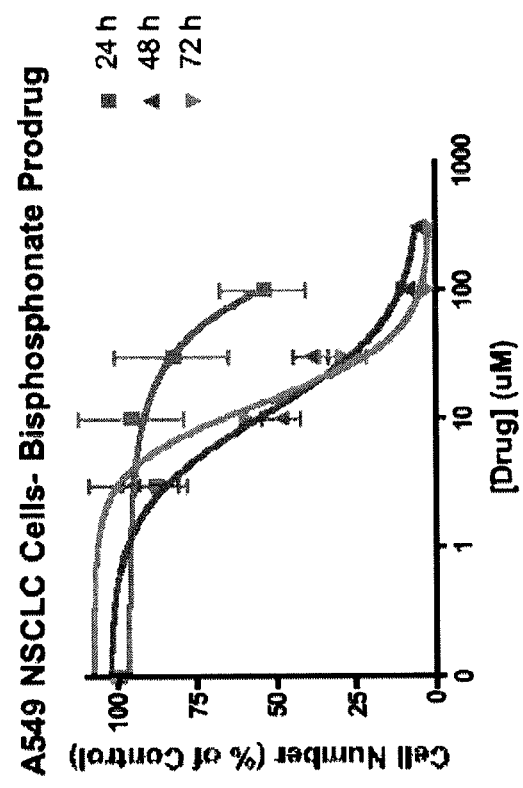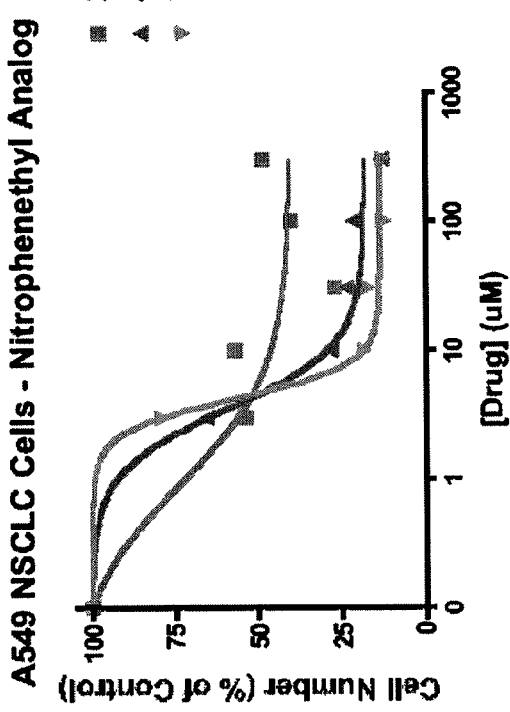
Figure 13 – cont.

BISPHOSPHONAMIDATE PRODRUGS AND USES THEREOF

CROSS-REFERENCE TO RELATED APPLICATION

This application claims priority to U.S. Provisional Application No. 61/329,466 filed Apr. 27, 2010, the entire contents of which are hereby incorporated by reference.

BACKGROUND

1. Field of the Invention

The present invention relates to prodrugs of therapeutic bisphosphonate compounds and uses thereof to treat or prevent diseases or disorders.

2. Background of the Invention

Clinically used bisphosphonates (BPs) are stable analogs of naturally occurring pyrophosphate (Knight et al., *Anticancer Drugs*, vol. 16, no. 9, pp. 969-976, 2005; Gnant et al., *Curr. Cancer Drug Targets*, vol. 9, pp. 824-833, 2009). BPs are known to inhibit cancer cell adhesion and invasion, and inhibit the growth of cancer cells in the bone microenvironment (Boissier et al., *Cancer Res., vol.* 57, no. 18, pp. 3890-3894, 1997; Boissier et al., *Cancer Res.* vol. 60, no. 11, pp. 2949-2954, 2000). The two bisphosphonate classes, nitrogen-containing (NBP) and non-nitrogen-containing (NNBP), are distinguished structurally by the substitution pattern at the bridging methylene of the P—C—P linkage. The NBP class incorporates a nitrogen-containing substituent at the bridging methylene (e.g. zoledronate, aledronate, pamidronate) whereas the NNBP class lacks this nitrogen-containing substituent (e.g. clodronate, etidronate) (FIG. 1).

These BP classes are further distinguished by differences in mechanism of action. The NBP class inhibits an essential enzyme in isoprenoid biosynthesis, farnesyl pyrophosphate synthase (FPPS), leading to lower farnesyl pyrophosphate (FPP) levels and subsequent reduction in downstream protein prenylation events in osteoclasts and malignant bone cells. Recent reports suggest that increased levels of the FPPS substrate, IPP, caused by inhibition of FPPS by NBPs, promote formation of AppIPP (triphosphoric acid 1-adenosine-5'yl ester 3-(3-methylbut-3-enyl) ester), which is believed to induce apoptosis (Räikkönen et al., *Biochem. Biophys. Res. Commun.*, Mar. 21, 2011). In contrast, NNBPs undergo conversion to the corresponding non-hydrolyzable ATP analogs. Clodronate is metabolized to the ATP analog AppCCl$_2$p (adenosine 5'-β-γ-dichloromethylene)triphosphosphate), which is believed to be the active metabolite responsible for the apoptotic activity of clodronate in observed osteoclasts and malignant bone cells (Rogers et al., *Biochem. J., vol.* 303, pp. 303-311, 1994; Frith et al., *J. Bone Miner. Res., vol.* 12, no. 9, pp. 1358-1367, 1997). Further, AppCCl$_2$p was shown to inhibit mitochondrial metabolism through inhibition of ADP/ATP translocase, and it is conceivable that additional targets are susceptible to inhibition by AppCCl$_2$p (Lehenkari et al., *Mol. Pharmacol., vol.* 62, pp. 1255-1262, 2002).

Skeletal-related events (SKE) such as fracture, spinal cord compression and hypercalcemia, are common and cause of significant morbidity in cancer patients with bone metastases (Domcheck et al., *Cancer*, vol. 89, pp. 363-368, 2000). Bisphosphonate therapy has been shown to reduce the rate of SKE in several clinical trials leading to its use as a standard adjunct therapy in patients with bone metastases. The clinical success of NBPs in the prevention and management of bone metastatases has led to the evaluation of BPs as potential therapeutic agents for the treatment of cancer in soft tissues (Morgan et al., *Seminars in Oncology*, vol. 37, no. 5, pp. S30-S40, 2010). The NBP zoledronate (5, FIG. 1) is a commonly used BP in metastatic bone disease and exhibits varying anti-cancer activities with IC$_{50}$s ranging from 3 to >100 μM in several cancer cell lines (Knight et al., *Anticancer Drugs, vol.* 16, no. 9, pp. 969-976, 2005; Morgan et al., *Seminars in Oncology*, vol. 37, no. 5, pp. S30-S40, 2010; Matsumoto et al., *Lung Cancer, vol.* 47, no. 1, pp. 31-39, 2005). The cytotoxic effects of zoledronate in cancer cells are believed to be exerted through a variety of mechanisms, including blockage of cell cycle in models of non-small cell lung cancer (Li et al., *Lung Cancer*, vol. 59, no. 2, pp. 180-191, 2008), inhibition of angiogenesis (Wood et al., *J. Pharmacol. Exp. Ther.*, vol. 302, no. 3, pp. 1055-1061, 2002; Croucher et al., *J. Bone Miner. Res., vol.* 18, no. 3, pp. 482-492, 2003; Santini et al., *Clin. Cancer Res., vol.* 13, no. 15, pp. 4482-4486, 2007; Hamma-Kourbali et al., *Biochem Biophys Res Commun., vol.* 310, no. 3, pp. 816-823, 2003), and induction of apoptosis in small cell lung cancer cell lines (Matsumoto et al., *Lung Cancer*, vol. 47, no. 1, pp. 31-39, 2005), although the molecular mechanisms beyond inhibition of FPPS are not well-understood.

NNBPs, including clodronate (1, FIG. 1) are significantly less potent anticancer agents (Lipton et al., *Cancer Treatment Reviews*, vol. 34, pp. 525-530, 2008), exhibiting growth inhibition in the high micromolar or low millimolar range in breast and ovarian cancers (Knight et al., *Anticancer Drugs*, vol. 16, no. 9, pp. 969-976, 2005), and minimal activity against lung cancer cell lines (Knight et al., *Anticancer Drugs*, vol. 16, no. 9, pp. 969-976, 2005). The anticancer activity of clodronate is thought to correlate with formation of AppCCl$_2$p in breast, prostate and myeloma cells (Mönkkönen et al., *Anticancer Drugs*, vol. 19, no. 4, pp. 391-399, 2008); however, the molecular mechanisms underlying the anticancer effects of clodronate are not well-understood.

BPs are polyanionic at physiologic pH, and are consequently concentrated in the mineralized bone matrix (Russell et al., *Osteoporosis Int.*, vol. 19, no. 6, pp. 733-759, 2008). While beneficial for the treatment of bone disorders, this structural characteristic of BPs precludes efficient uptake into extraskeletal tumor cells. The low cellular uptake of BPs presents a critical barrier both for the development of these agents to treat tumors in soft tissues and for studies to elucidate the intracellular mechanisms by which BPs exert antitumor effects.

Existing strategies to increase bioavailability of NNBPs such as clodronate have involved masking of the BP scaffold with biodegradable or chemically labile groups designed to release the corresponding BP through non-specific esterase activation or chemical hydrolysis post-intestinal absorption (Ahlmark et al., *J. Med. Chem., vol.* 42, no. 8, pp. 1473-1476, 1999; Vepsalainen et al., *Curr. Med. Chem., vol.* 9, pp. 1201-1208, 2002; Zhang et al., *J. Med. Chem., vol.* 49, no. 9, pp. 5804-5814, 2006). These prodrugs generally undergo rapid extracellular bioactivation in serum, leading to partially unmasked, impermeable intermediates, which are often inefficiently converted to the fully unmasked BP. There are no such prodrug strategies reported for BPs bearing the tertiary hydroxyl group at the bridging methylene position, including the NBP class, owing to the intrinsic instability of these compounds when masked as tetraesters (Neimi et al., *Eur. J. Pharm. Sci.*, vol. 11, no. 2, pp. 173-180, 2000). Other strategies to increase BP cell permeability have focused on introducing modifications at the bridging methylene of the P—C—P linkage to increase hydrophobicity. Such modifications have also been shown to impart changes in target specificity (Szabo et al., *J. Med. Chem., vol.* 45, no. 11, pp. 2185-2196, 2002; Shull et al., *Bioorg. Med. Chem., vol.* 14, no. 12, pp. 4130-4136, 2006; Barney et al. *Bioorg. Med. Chem.* vol.

18, no. 20, pp. 7212-722, 2010). However, increasing hydrophobicity of substituents at the bridging methylene group does not overcome low membrane permeability entirely, as phosphonate masking strategies have been employed in these cases as well (Zhang et al. *J. Med. Chem.* vol. 49, no. 9, pp. 5804-5814, 2006; Wiemer et al. *Bioorg. Med. Chem.* vol. 16, no. 7, pp. 3652-3660, 2008).

SUMMARY

Embodiments of the invention include compounds of the formula

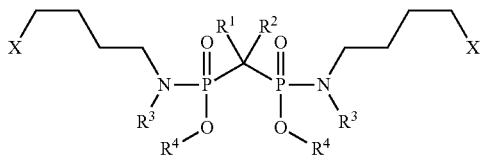

are the same or different and each is selected is H, halogen, alkyl, alkenyl, haloalkyl, aralkyl, heteroaralkyl, aryloxy, arylthio, aminoalkyl, hydroxylalkyl, alkoxyalkyl hydroxyl, amino, alkylamino, arylamino, heteroarylamino, alkylaminoalkyl, arylaminoalkyl, heteroarylaminoalkyl, alkoxy, alkoxyalkyl, alkylthio, O-acyl, N-acyl, or S-acyl, or $R^1$ is H, halogen, alkyl, alkenyl, haloalkyl, aralkyl, heteroaralkyl, aryloxy, arylthio, aminoalkyl, hydroxylalkyl, alkoxyalkyl and $R^2$ is H, halogen, alkyl, alkenyl, haloalkyl, hydroxyl, amino, alkoxy, alkylthio, O-acyl, N-acyl, or S-acyl. Each $R^3$ is the same or different and is alkyl, hydroxyl, or alkoxy. X is a leaving group. Each $R^4$ is the same or different and is alkyl, aralkyl, heteroaralkyl or

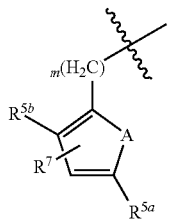

where m is 1, 2, 3, 4, 5, or 6. One of $R^{5a}$ and $R^{5b}$ is H or $R^7$ and the other of $R^{5a}$ and $R^{5b}$ is H, halogen, nitro, alkyl, haloalkyl, hydroxyl, amino, alkoxy, alkylthio, O-acyl, N-acyl, S-acyl or N—O-Acyl. $R^7$ represents one or more substituents up to the total number of available positions and is hydrogen, halogen, alkyl, haloalkyl, or alkoxy. A is —O—, —S—, —N($R^8$)—, —C=C—; —C=N—, or N=C and $R^8$ is hydrogen or alkyl. Alternatively, both R4 taken together are

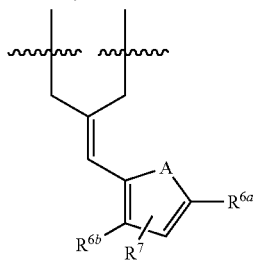

wherein $R^7$ is defined as above and one of $R^{6a}$ and $R^{6b}$ is H or $R^7$ and the other of $R^{6a}$ and $R^{6b}$ is nitro, O-acyl, N-acyl, N—O-acyl or —N=N—$R^9$ where $R^9$ is alkyl or aryl. Embodiments also include pharmaceutically acceptable salts of any of the above compounds.

In some embodiments, $R^1$ is hydrogen, alkyl, halogen, aminoalkyl, thioaryl, or heteroalkyl. In some embodiments, $R^2$ is H, halogen, or hydroxyl. In some embodiments, $R^1$ and $R^2$ are H. In some embodiments, $R^1$ and $R^2$ are Cl. In some embodiments, $R^1$ is heteroaralkyl or aminoalkyl, and $R^2$ is hydroxyl.

In some embodiments, $R^3$ is alkyl.
In some embodiments, $R^4$ is alkyl or aralkyl.
In some embodiments, X is Cl.
Embodiments include compounds having the formula

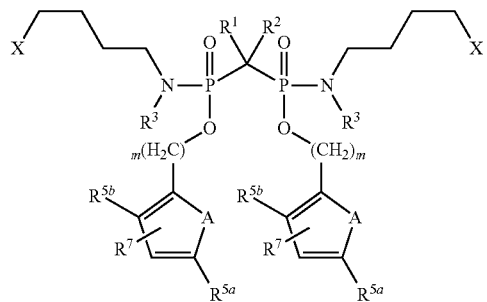

where $R^1$ is H, halogen, alkyl, haloalkyl, aralkyl, heteroaralkyl, aryloxy, arylthio, aminoalkyl, hydroxylalkyl, alkoxyalkyl and $R^2$ is H, halogen, alkyl, haloalkyl, hydroxyl, amino, alkoxy, alkylthio, O-acyl, N-acyl, or S-acyl.

In some embodiment, $R^5$ is hydrogen or nitro.
In some embodiments, $R^1$ is hydrogen, alkyl, halogen, aminoalkyl, thioaryl, heteroalkyl. In some embodiments, $R^2$ is H, halogen, or hydroxyl. In some embodiments, $R^1$ and $R^2$ are H. In some embodiments, $R^1$ and $R^2$ are Cl. In some embodiments, $R^1$ is heteroaralkyl or aminoalkyl, and $R^2$ is hydroxyl.

In some embodiments, $R^3$ is alkyl.
In some embodiments, A is —C=C—.
In some embodiments, X is Cl.
Embodiments of the invention include compounds having the structure

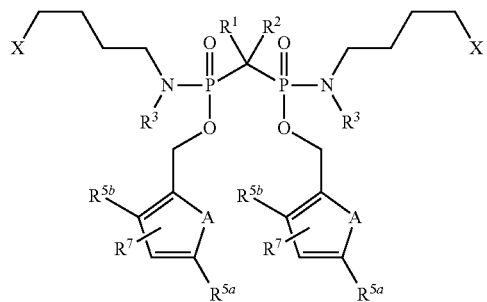

where one of $R^{5a}$ and $R^{5b}$ is H or $R^7$ and the other of $R^{5a}$ and $R^{5b}$ is O-acyl, N-acyl, N—O-acyl. In some embodiments, $R^5$ is nitro.

In some embodiments, $R^1$ is hydrogen, alkyl, halogen, aminoalkyl, thioaryl, heteroalkyl. In some embodiments, $R^2$ is H, halogen, or hydroxyl. In some embodiments, $R^1$ and $R^2$ are H. In some embodiments, $R^1$ and $R^2$ are Cl. In some embodiments, $R^1$ is heteroaralkyl or aminoalkyl, and $R^2$ is hydroxyl.

In some embodiments, $R^3$ is alkyl.
In some embodiments, A is —C=C—.
In some embodiments, X is Cl.

Embodiments of the invention include compounds having the structure

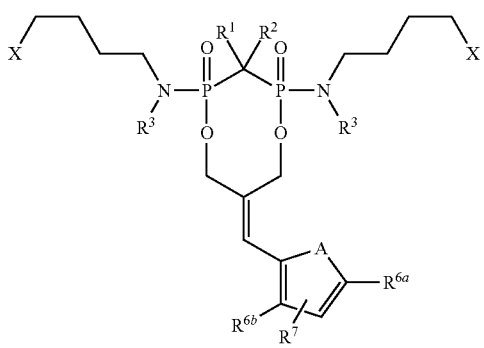

where $R^1$ is H, halogen, alkyl, haloalkyl, aralkyl, heteroaralkyl, aryloxy, arylthio, aminoalkyl, hydroxylalkyl, or alkoxyalkyl, and $R^2$ is H, halogen, alkyl, haloalkyl, hydroxyl, amino, alkoxy, alkylthio, O-acyl, N-acyl, or S-acyl.

In some embodiments, $R^6$ is nitro.

In some embodiments, $R^1$ is hydrogen, alkyl, halogen, aminoalkyl, thioaryl, heteroaralkyl. In some embodiments, $R^2$ is H, halogen, or hydroxyl. In some embodiments, $R^1$ and $R^2$ are H. In some embodiments, $R^1$ and $R^2$ are Cl. In some embodiments, $R^1$ is heteroaralkyl or aminoalkyl, and $R^2$ is hydroxyl.

In some embodiments, $R^3$ is alkyl.

In some embodiments, A is —C=C—.

In some embodiments, X is Cl.

Embodiments of the invention include pharmaceutical compositions having any bisphosphonamidate compound described herein.

Embodiments of the invention include methods of treating a disease by administering to a subject in need of treatment a therapeutically effective amount of a compound described herein. In some embodiments, the disease is hypercalcemia, osteoporosis or malignant bone disease.

In some embodiments, the disease is a hyperproliferative disorder. In some embodiments, the hyperproliferative disorder is non-small cell lung cancer, colon cancer, leukemia, CNS cancer, melanoma, ovarian cancer, renal cancer, prostate cancer, or breast cancer.

In some embodiments, the disease is an infection by a bacteria or parasite. In some embodiments, the parasite is *plasmodium falciparum* or *trypanosoma brucei brucei*.

BRIEF DESCRIPTION OF THE DRAWINGS

FIG. 4A shows Bisphosphonate prodrug (13) (■) enhanced anti-proliferative effect compared to bisphosphate (●). FIG. 4B shows Clodronate prodrug (14) (■) enhanced anti-proliferative effect compared to clodronate (●). FIG. 4C shows effect of 13 at 24 h (□), 48 h (▲), and 72 h (○). FIG. 4D shows effect of 14 at 24 h (□), 48 h (▲), and 72 h (○).

FIG. 7A shows the effect of clodronate prodrug (14) on proliferation of melanoma cells after 24 h. FIG. 7B shows the effect of clodronate prodrug (14) on proliferation of melanoma cells after 48 h. FIG. 7C shows the effect of clodronate prodrug (14) on proliferation of melanoma cells after 72 h.

FIG. 8A shows the effect of clodronate prodrug (14) on proliferation of NSCLC cells after 24 h drug treatment and additional 24 h growth in drug free media. FIG. 8B shows the effect of clodronate prodrug (14) on proliferation of NSCLC cells after 2 h exposure followed by 46 h of growth in drug free media.

FIG. 9A shows the effect of clodronate prodrug (14) on proliferation of NSCLC cells grown under normoxic conditions when exposed to 14 for 24 h, then grown for an additional 24 h in drug free media. FIG. 9B shows the effect of clodronate prodrug (14) on proliferation of NSCLC cells grown under hypoxic conditions when treated with 14 for 24 h followed by 24 h growth in drug free media.

FIG. 13E shows the activity of the nitrophenethyl prodrug of clodronate measured using the trypan blue assay, which measures change in cell number in the wells dosed with drug compared to control (% of control). FIG. 13F shows the activity of the bisphosphonate prodrug (compound 13) measured using the trypan blue assay.

FIG. 20 shows annexin V staining and flow cytometry to analyze markers of early apoptosis.

FIG. 21A shows a positive control, supernatant from lung fibroblasts. FIG. 21B shows treatment with 2 μM clodronate prodrug, FIG. 21C shows treatment with 6 μM clodronate prodrug, FIG. 21D shows treatment with 10 μM clodronate prodrug. At 6 μM clodronate prodrug, sprouting was delayed for the first few days and "punched through" late in the assay. At 10 μM clodronate prodrug, sprouting is inhibited.

DETAILED DESCRIPTION

Definitions

Figure 1:
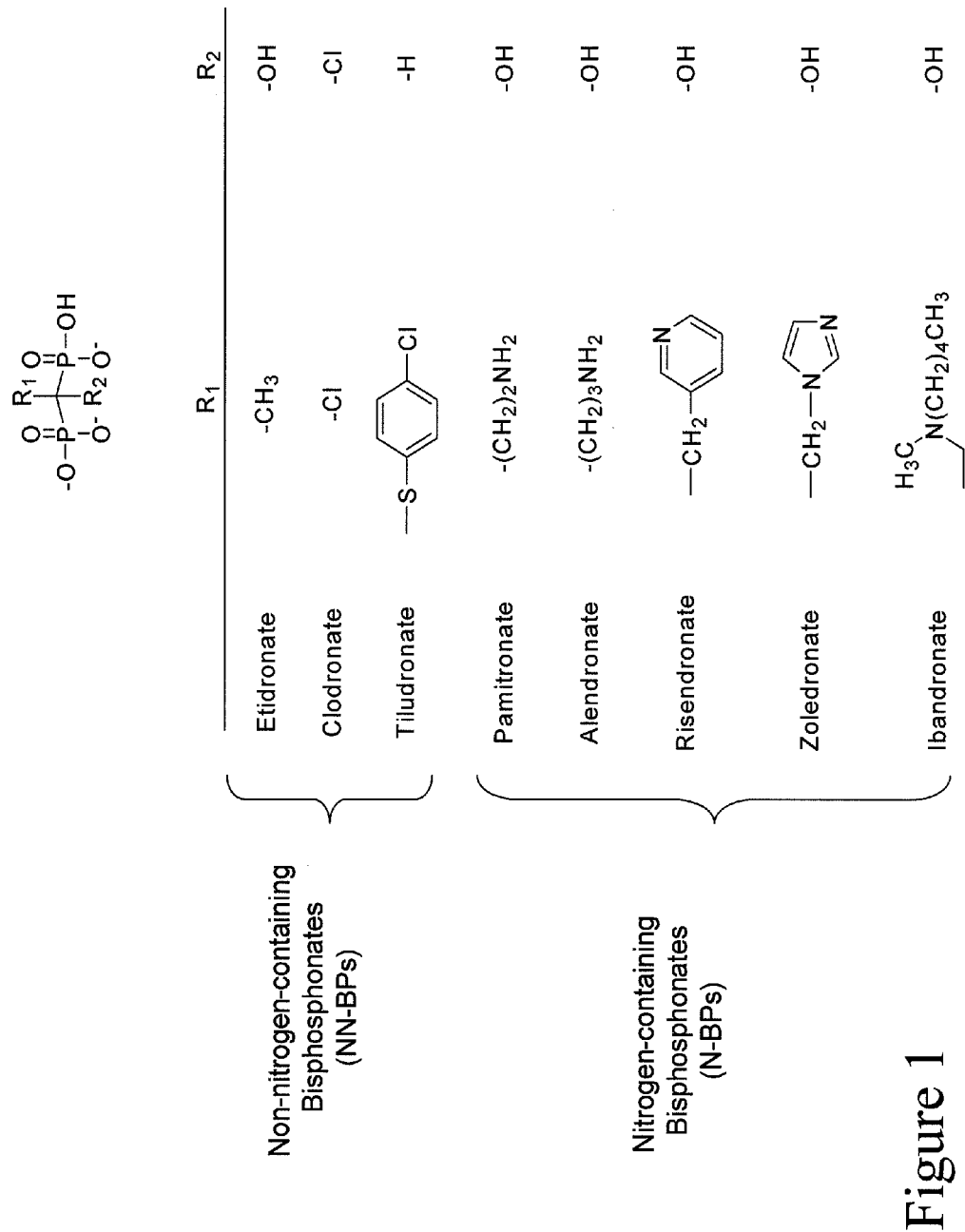
FIG. 1 shows clinically-used NBPs and NNBPs.

Terms used herein have their normal meaning as would be understood by persons skilled in the art. By way of example, and not to contradict or alter the generally accepted meanings, certain terms are defined below for clarity.

As used herein, "agent" is a non-peptide, small molecule compound according to the invention.

By "control" is meant a standard or reference condition.

By "disease" is meant any condition or disorder that damages or interferes with the normal function of a cell, tissue, organ or subject.

By "effective amount" is meant the amount of an agent required to ameliorate the symptoms of a disease relative to an untreated subject. The effective amount of an active therapeutic agent for the treatment of a disease or injury varies depending upon the manner of administration, the age, body weight, and general health of the subject. Ultimately, the attending clinician will decide the appropriate amount and dosage regimen.

By "modifies" is meant alters. An agent that modifies a cell, substrate, or cellular environment produces a biochemical alteration in a component (e.g., polypeptide, nucleotide, or molecular component) of the cell, substrate, or cellular environment.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

As used herein, a "prodrug" is a compound that, while not itself necessarily pharmacologically inactive, is converted into a pharmacologically active agent by a transformation, for example a metabolic transformation, after administration.

By "subject" is meant a mammal, including, but not limited to, a human or non-human mammal, such as a bovine, equine, canine, ovine, or feline.

As used herein, the terms "treat," treating," "treatment," "therapeutic" and the like refer to reducing or ameliorating a disorder and/or symptoms associated therewith. It will be appreciated that, although not precluded, treating a disorder or condition does not require that the disorder, condition or symptoms associated therewith be completely eliminated.

Compounds

Embodiments include compounds having the formula shown below

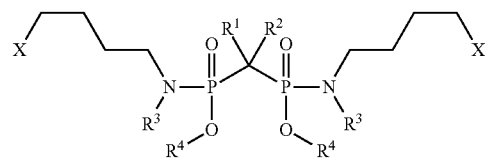

where $R^1$ and $R^2$ may be the same or different, and may be H, halogen, alkyl, alkenyl, haloalkyl, aralkyl, heteroaralkyl, aryloxy, arylthio, aminoalkyl, hydroxylalkyl, alkoxyalkyl hydroxyl, amino, alkylamino, arylamino, heteroarylamino, alkylaminoalkyl, arylaminoalkyl, heteroarylaminoalkyl, alkoxy, alkoxyalkyl, alkylthio, O-acyl, N-acyl, or S-acyl, so long as $R^1$, $R^2$ and the carbon atom between them do not form O—C—O, O—C—N, O—C—S, N—C—S, N—C—N or S—C—S. In other words, $R^1$, $R^2$ and the carbon atom between them do not form ketals, monothioketals, dithioketals, monoaminoketals or diaminoketals. In some embodiments, $R^1$ is H, halogen, alkyl, haloalkyl, aralkyl, heteroaralkyl, aryloxy, alkoxy, amino, arylthio, aminoalkyl, hydroxylalkyl, or alkoxyalkyl and $R^2$ is H, halogen, alkyl, alkenyl, haloalkyl, hydroxyl, amino, alkoxy, alkylthio, O-acyl, N-acyl, or S-acyl. Each $R^3$ can be alkyl, hydroxyl, or alkoxy; and each $R^3$ may be the same or may be different. X is a leaving group. Each $R^4$ can be alkyl, aralkyl, heteroaralkyl or the substructure shown below.

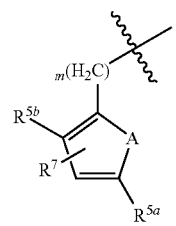

where m is 1, 2, 3, 4, 5, or 6. One of $R^{5a}$ and $R^{5b}$ is H or $R^7$ and the other of $R^{5a}$ and $R^{5b}$ is H, halogen, nitro, alkyl, haloalkyl, hydroxyl, amino, alkoxy, alkylthio, O-acyl, N-acyl, S-acyl or N—O-acyl. $R^7$ represents one or more substituents up to the total number of available positions and is hydrogen, halogen, alkyl, haloalkyl, or alkoxy. Each $R^4$ may be the same or may be different. A is —O—, —S—, —N($R^8$)—, —C═C—; —C═N—, or N═C and $R^8$ is hydrogen or alkyl. Alternatively, the two $R^4$ groups can be taken together to form

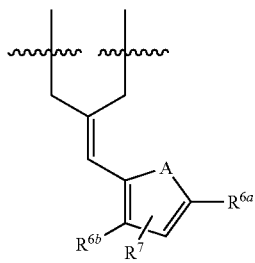

where one of $R^{6a}$ and $R^{6b}$ is H or $R^7$ and the other of $R^{6a}$ and $R^{6b}$ is nitro, O-acyl, N-acyl, N—O-acyl, or —N=N—$R^9$ where $R^9$ is alkyl or aryl. In other words, embodiments include compounds having the formula shown below.

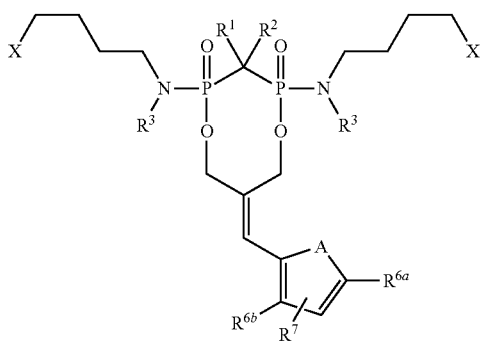

where $R^1$, $R^2$, $R^3$, and $R^7$ are defined as above and one of $R^{6a}$ and $R^{6b}$ is H or $R^7$ and the other of $R^{6a}$ and $R^{6b}$ is nitro, O-acyl, N-acyl, N—O-acyl, or —N=N—$R^9$ where $R^9$ is alkyl or aryl.

Embodiments include compounds having the formula shown below.

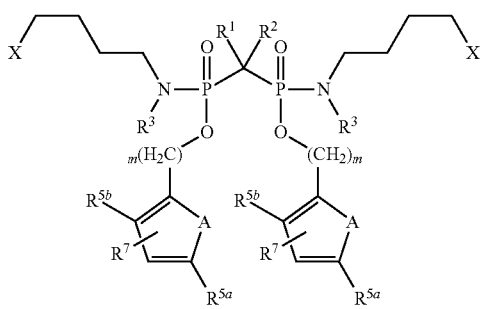

where m is 1, 2, 3, 4, 5, or 6. $R^1$, $R^2$, $R^3$, $R^{5a}$, $R^{5b}$, and $R^7$ are defined above.

Embodiments include compounds having the structure shown below.

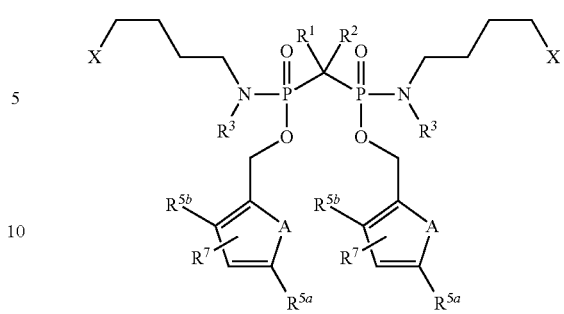

where m is 1, 2, 3, 4, 5, or 6. $R^1$, $R^2$, $R^3$, $R^{5a}$, $R^{5b}$, and $R^7$ are defined above.

In any embodiment, $R^1$ may be H, halogen, alkyl, alkenyl, haloalkyl, aralkyl, heteroaralkyl, aryloxy, arylthio, aminoalkyl, hydroxylalkyl, alkoxyalkyl. In any embodiment, $R^1$ may be H, halogen, alkyl, haloalkyl, aralkyl, heteroaralkyl, aryloxy, alkoxy, amino, arylthio, aminoalkyl, hydroxylalkyl, or alkoxyalkyl. In any embodiment, $R^1$ may be hydrogen, alkyl, halogen, aminoalkyl, thioaryl, heteroaralkyl. In any of embodiment, $R^1$ may be H or halogen. In any embodiment, $R^1$ may be Cl.

Example $R^1$ include, for example, H, methyl, chloro, 2-aminoethyl, 3-aminopropyl, and structures shown below.

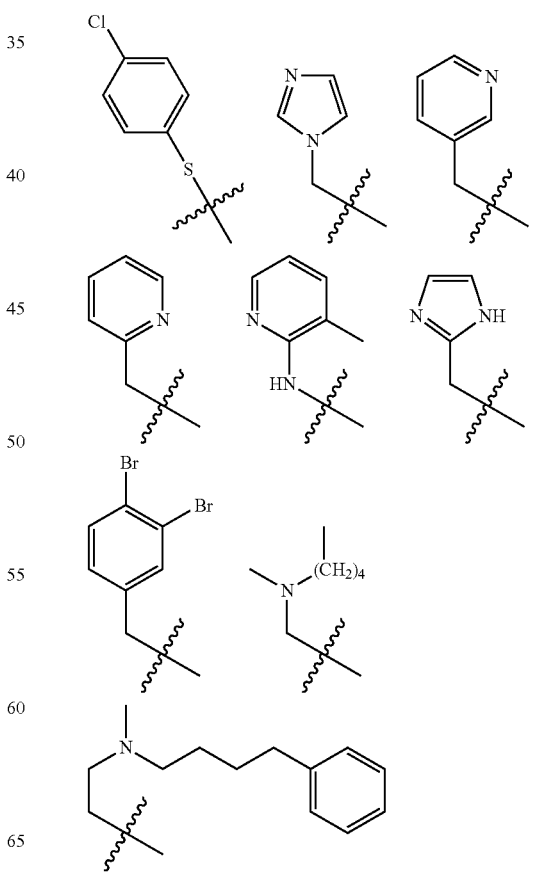

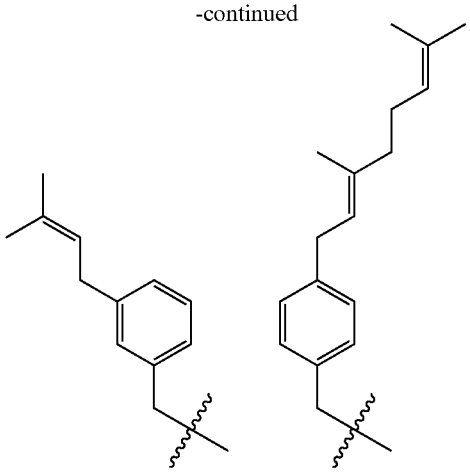

In any embodiment, $R^2$ may H, halogen, alkyl, haloalkyl, alkenyl, hydroxyl, amino, alkylamino, arylamino, heteroarylamino, alkylaminoalkyl, arylaminoalkyl, heteroarylaminoalkyl, alkoxy, alkoxyalkyl, alkylthio, O-acyl, N-acyl, or S-acyl. In any embodiment, $R^2$ may be H, halogen, alkyl, haloalkyl, hydroxyl, amino, alkoxy, alkylthio, O-acyl, N-acyl, or S-acyl. In any embodiment, $R^2$ may be H, halogen, or hydroxyl. In any embodiment, $R^2$ may be H or Cl.

Example $R^2$ include, for example, H, chloro, hydroxyl, or geranyl (shown below)

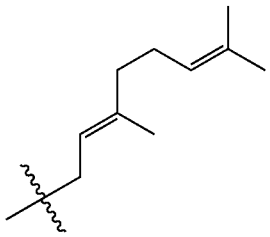 [SMILES: *C/C=C(\C)CCC=C(C)C]

In any embodiment, $R^1$ may be heteroaralkyl or aminoalkyl and $R^2$ may be hydroxyl. In any embodiment, $R^1$ and $R^2$ may be H. In any embodiment, $R^1$ and $R^2$ may be Cl.

$R^1$ and $R^2$ define a pharmaceutically active, bisphosphonate compound that is unmasked from the prodrug. Many pharmaceutically active bisphosphonate compounds are known, and may be prepared as prodrugs in accordance with this invention. Examples of pharmaceutically active bisphosphonate compounds are shown in FIG. 1. In general, any bisphosphonate compound may be prepared as a bisphosphonamidate prodrug according to this invention.

In any embodiment, $R^3$ may be alkyl. In any embodiment, $R^3$ may be methyl.

In any embodiment, $R^5$ may be H, nitro, O-acyl, N-acyl or N—O-acyl. In any embodiment, $R^5$ may be nitro.

In any embodiment, $R^6$ may be nitro, O-acyl, N-acyl or N—O-acyl. In any embodiment, $R^6$ may be nitro.

In any embodiment, $R^7$ may be one or more substituents, up to the total number of available positions. When multiple $R^7$ are present, they may be the same or different. In any embodiment, $R^7$ may be hydrogen, halogen, alkyl, haloalkyl, or alkoxy. In any embodiment, $R^7$ may be hydrogen.

In any embodiment, $R^5$ or $R^6$ may be a targeting ligand. As used herein, a targeting ligand is a chemical structure that binds to a cell surface protein. Examples include, for example, PSA (prostate-specific antigen) peptides. In any embodiment, $R^7$ may be a targeting ligand, such as, for example, PSA peptide.

In any embodiment, X is a leaving group. A leaving group (LG), as used herein, is an atom (or a group of atoms) that is displaced as stable species taking with it the bonding electrons. Examples of leaving groups include halogen ions, such as chloride, bromide or iodide, and sulfonate esters, such as, for example, fluorosulfonate, alkylsulfonates, such as mesylate, aryl sulfonates, such as toluene sulfonate, or haloalkyl mesylates, (including perfluorinated alkyl) such as trifluoromethylsulfonate (triflate) or perfluorobutylsulfonates (nonaflates). In any embodiment, X may be Cl.

In any embodiment, A may be —O—, —S—, —C=C—; —C=N—, N=C, or —N($R^8$)— where $R^8$ is hydrogen or alkyl. In other words, the ring containing A may be phenyl, pyridyl, furanyl, thiophenyl, or pyrrolyl. In any embodiment, A may be —C=C—. In other words, in any embodiment, the ring containing A may be a phenyl ring.

In any embodiment, the compound may be a pharmaceutically acceptable salt.

Specific examples of compounds are shown below.

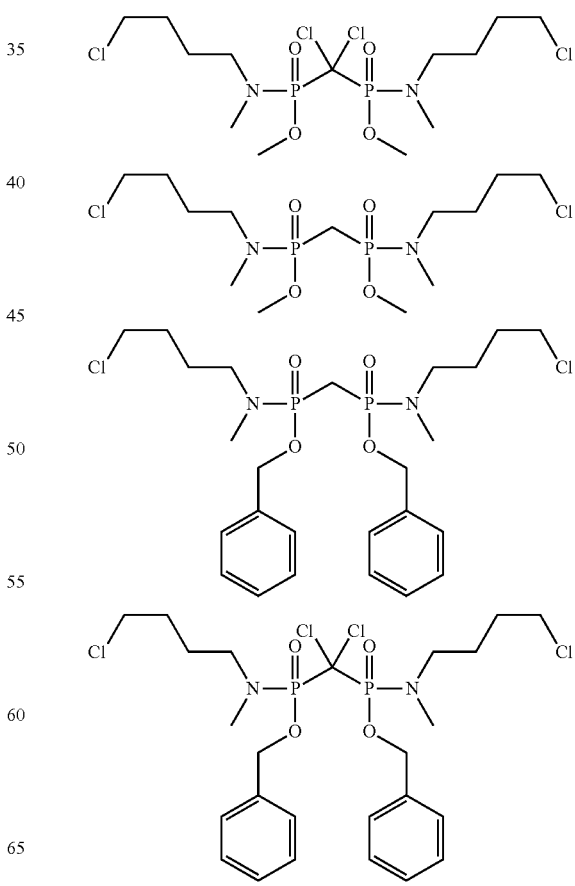

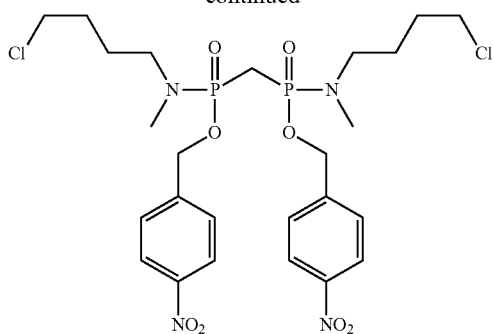
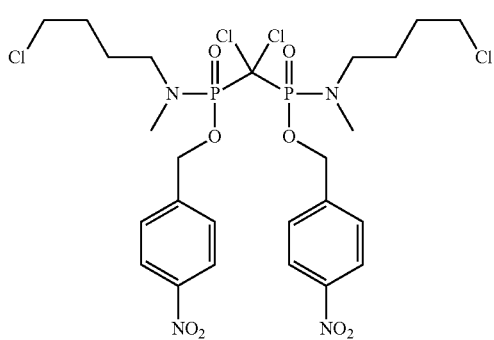
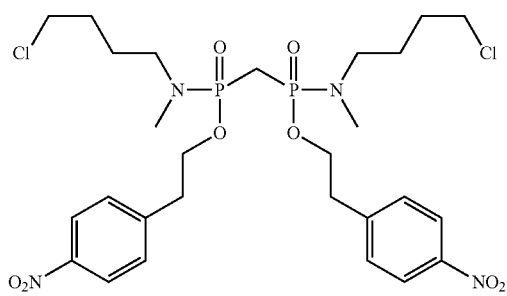
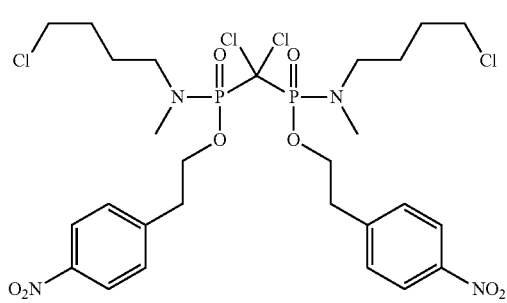
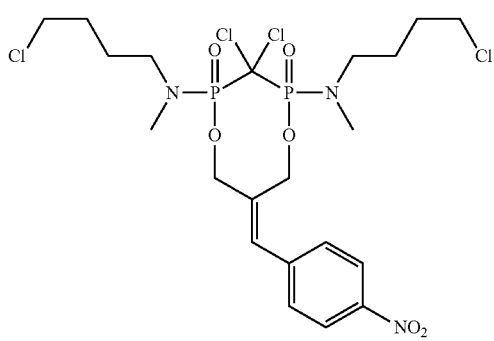

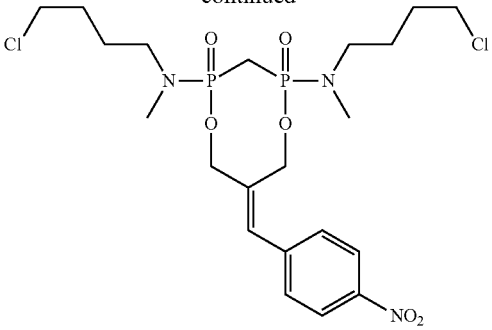

The terms "alkyl" used alone or as part of a larger moiety (i.e. "alkoxy," "hydroxyalkyl," "alkoxyalkyl," and "alkoxycarbonyl") include both straight and branched chains containing one to ten carbon atoms (i.e. 1, 2, 3, 4, 5, 6, 7, 8, 9, or 10 carbon atoms), as well as cyclic structures such as cyclopropyl and cyclobutyl. Examples of alkyl groups include methyl (Me), ethyl (Et), propyl (Pr) (including n-propyl ($^n$Pr or n-Pr), isopropyl ($^i$Pr or i-Pr) and cyclopropyl ($^c$Pr or c-Pr)), butyl (Bu) (including n-butyl ($^n$Bu or n-Bu), isobutyl ($^i$Bu or i-Bu), tert-butyl ($^t$Bu or t-Bu) and cyclobutyl ($^c$Bu or c-Bu)), pentyl (Pe) (including n-pentyl) and so forth. Alkyl groups also include mixed cyclic and linear alkyl groups, such as cyclopentylmethyl, cyclopentylethyl, cyclohexylmethyl, etc., so long as the total number of carbon atoms is not exceeded. The term "alkoxy" refers to an —O-alkyl radical, such as, for example —O-Me, —O-Et, —O—Pr, and so on. The term "hydroxyalkyl" refers to an alkyl group substituted with one or more hydroxyl, such as, for example, hydroxymethyl, 1-hydroxyethyl, 2-hydroxyethyl, 1,2-dihydroxyethyl, and so forth. The term "thioalkyl" refers to an —S-alkyl group, such as, for example, example —S-Me, —S-Et, —S—Pr. The term "haloalkyl" means alkyl, substituted with one or more halogen atoms, such as trifluoromethyl, chloromethyl, 2,2,2-trifluoroethyl, 1,1,2,2,2,-petanfluoroethyl, and so on. The term "aminoalkyl" means alkyl, substituted with an amine group ($NH_2$), such as, for example, aminomethyl, 1-aminoethyl, 2-aminoethyl, 3-aminopropyl and so forth. The term "alkoxyalkyl" refers to an alkyl group, substituted with an alkoxy group, such as, for example, methoxymethyl, ethoxymethyl, methoxyethyl, and so forth. As used herein, the term "alkylaminoalkyl" refers to an alkyl group substituted with an alkylamine group, such as, for example, N-methylaminomethyl, N,N-dimethylaminomethyl, N,N-methylpentylaminomethyl, 2-(N-methylamino)ethyl, 2-(N,N-dimethylamino)ethyl, and so forth.

The term "halogen" or "halo" means F, Cl, Br, or I.

The term "nitro" means (—$NO_2$).

The term "amine" or "amino" used alone or as part of a larger moiety refers to unsubstituted (—$NH_2$). The term "alkylamine" refers to mono-(—NRH) or di-substituted (—$NR_2$) amine where at least one R group is an alkyl substituent, as defined above. Examples include methylamino (—$NHCH_3$), dimethylamino (—$N(CH_3)_2$), The term "arylamine" refers to a mono (—NRH) or di-substituted (—$NR_2$) amine, where at least one R group is an aryl group as defined below, including, for example, phenylamino, diphenylamino, and so forth. The term "heteroarylamine" refers to a mono (—NRH) or di-substituted (—$NR_2$) amine, where at least one R group is a heteroaryl group as defined below, including, for example, 2-pyridylamino, 3-pyridylamino and so forth. The term "aralkylamine" refers to a mono (—NRH) or di-substituted (—$NR_2$) amine, where at least one R group is an aralkyl group, including, for example, benzylamino, phenethylamino, and so forth. The term "heteroaralkylamine" refers to a mono (—NRH) or di-substituted (—NR$_2$) amine, where at least one R group is a heteroaralkyl group. As used herein, the term "alkylaminoalkyl" refers to an alkyl group substituted with an alkylamine group. Analogously, "arylaminoalkyl" refers to an alkyl group substituted with an arylamine, and so forth, for any substituted amine described herein.

The term "alkenyl" used alone or as part of a larger moiety include both straight and branched chains containing at least one double bond and two to ten carbon atoms (i.e. 2, 3, 4, 5, 6, 7, 8, 9, or 10 carbon atoms), as well as cyclic, non-aromatic alkenyl groups such as cyclopropenyl, cyclobutenyl, cyclopentenyl, cyclopentadienyl, cyclohexenyl, cyclohexadienyl, etc. As used herein, alkenyl groups also include mixed cyclic and linear alkyl groups, such as cyclopentenylmethyl, cyclopentenylmethyl, cyclohexenylmethyl, etc., so long as the total number of carbon atoms is not exceeded. When the total number of carbons allows (i.e. more than 4 carbons), an alkenyl group may have multiple double bonds, whether conjugated or non-conjugated, but do not include aromatic structures. Examples of alkenyl groups include ethenyl, propenyl, butenyl, butadienyl, isoprenyl, dimethylallyl, geranyl and so forth.

The term "aryl" used alone or as part of a larger moiety, refers to mono-, bi-, or tricyclic aromatic hydrocarbon ring systems having five to fourteen members, such as phenyl, 1-naphthyl, 2-naphthyl, 1-anthracyl and 2-anthracyl. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenanthridinyl or tetrahydronaphthyl, where the radical or point of attachment is on the aromatic ring. The term "aralkyl" refers to an alkyl substituent substituted by an aryl group. The term "aryloxy" refers to an —O-aryl group, such as, for example phenoxy, 4-chlorophenoxy and so forth. The term "arylthio" refers to an —S-aryl group such as, for example phenylthio, 4-chlorophenylthio, and so forth. The term "aryl" used alone or as part of a larger moiety also refers to aryl rings that are substituted such as, for example, 4-chlorophenyl, 3,4-dibromophenyl and so forth. An aryl group may have more than one substituent, up to the total number of free substitution positions. For example, an aryl group may have 1, 2, 3, 4, or 5 substituents. The substituents may the same or different. Substituents on an aryl group include hydrogen, halogen, alkyl, alkenyl, nitro, hydroxyl, amino, alkylamino, alkoxy, and alkylthio, O-acyl, N-acyl, S-acyl as defined herein.

The term "heteroaryl", used alone or as part of a larger moiety, refers to heteroaromatic ring groups having five to fourteen members, preferably five to ten, in which one or more ring carbons, preferably one to four, are each replaced by a heteroatom such as N, O, or S. Examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 3-pyrazolyl, 4-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, or benzoisoxazolyl. Also included within the scope of the term "heteroaryl", as it is used herein, is a group in which a heteroaromatic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" may be used interchangeably with the term "heteroaryl ring" or the term "heteroaromatic." The term "heteroaralkyl" refers to an alkyl group substituted by a heteroaryl, such as, for example, 2-pyridylmethyl, 3-pyridylmethyl, 1-imidazolomethyl, 2-imidazolomethyl and so forth. The term "heteroaryloxy" refers to an —O-heteroaryl group. The term "heteroarylthio" refers to an —S-aryl group. A heteroaryl group may have more than one substituent, up to the total number of free substitution positions. For example, a heteroaryl group may have 1, 2, 3, 4, or 5 substituents. The substituents may the same or different. Substituents on a heteroaryl group include hydrogen, halogen, alkyl, alkenyl, nitro, hydroxyl, amino, alkylamino, alkoxy, and alkylthio, O-acyl, N-acyl, S-acyl as defined herein.

The term "O-acyl" refers to an "—O—C(O)-alkyl," "—O—C(O)-aryl," or "—O—C(O)-heteroaryl" group. The term "N-acyl" refers to an "—NR—C(O)-alkyl," "—NR—C(O)-aryl," or "—NR—C(O)-heteroaryl" where R is an alkyl, hydroxyl, or alkoxy group. The term "S-acyl" refers to "—S—C(O)-alkyl," "—S—C(O)-aryl," or "—S—C(O)-heteroaryl." The term "N—O-acyl" refers to an "N—O—C(O)-alkyl," "N—O—C(O)-aryl," or "N—O—C(O)-heteroaryl" group.

As used herein, a "substituted" structure refers to a chemical structure where a hydrogen atom has been replaced by a substituent. A "substituent" is a chemical structure that replaces a hydrogen atom on the substituted structure. The term "substituent" does not imply that the substituent is smaller than the substituted structure.

Preparation

Compounds according to the invention may be made using methods described herein, for example, in the Examples given below, or according to procedures known in the art.

For example, compounds may be prepared from methylene (bisphosphonic dichloride) by reacting with an alcohol, such as, for example, p-nitrobenzyl alcohol and a chlorobutyl amine, such as, for example, N-chlorobutyl-N-methylamine to prepare the bisphosphonamidate prodrug of bisphosphonate, followed by substitution of the bisphosphonamidate to add substitutents $R^1$ and $R^2$ of the compounds described above using procedures known in the art. In some embodiments, methylene(bisphosphonic dichloride) is reacted with the chlorobutyl amine first, followed by the alcohol. In other embodiments, the opposite order is used.

Alternatively, compounds may be prepared from substituted bisphosphonate having $R^1$ and $R^2$ (where $R^1$ and $R^2$ are not both H) substituents already present by reacting the substituted bisphosphonate with, for example, a halide, mesylate, or other leaving-group bearing reagent, such as, for example, p-nitrobenzyl bromide to form a bisphosphonate diester. Other suitable leaving groups will be readily apparent to one of ordinary skill in the art. The bisphosphonate diester may then be activated with, for example, a carbodiimide reagent. Other activating reagents will be readily apparent to one of ordinary skill in the art. The activated bisphosphonate diester is reacted with a chlorobutyl amine, such as, for example N-chlorobutyl-N-methylamine to form a bisphosphonamidate prodrug of the invention.

If necessary, reactive substituents, such as, for example, hydroxyl or amine groups, may be protected using protecting group chemistry known in the art.

Mechanism

The low membrane permeability of bisphosphonates imposes a significant bather to the development of these agents for the treatment of extraskeletal tumors. Clodronate displays varying effects in different cancer cell types (Knight et al., *Anticancer Drugs*, vol. 16, no. 9, pp. 969-976, 2005), with minimal activity against lung cancer cells. Studies to investigate differences in the mechanism of clodronate action that could account for these differences are also impeded by poor cellular uptake. A bisphosphoamidate prodrug strategy has been developed that significantly enhances the membrane permeability of bisphosphonates through incorporation of two biodegradable delivery groups and two halobutyl amine masking groups. Biodegradable delivery groups is intended to mean groups that are removed, for example by reduction, enzymatic hydrolysis or non-enzymatic hydrolysis, in the body. The use of only two biodegradable delivery groups takes advantage of the most efficient enzymatic activation steps and exploits the exquisite reactivity of chemically labile halobutyl phosphonamidate anion intermediates along the prodrug activation pathway for rapid intracellular activation and release of the fully unmasked bisphosphonate. This advantage may be increased by the use of cyclic prodrugs described herein, which can require only a single enzymatic activation (see FIG. 14). The remarkable enhancement of activity of bisphosphonamidate prodrugs in A549 cells compared to the parent BPs highlights the potential utility of this approach to extend the use of bisphosphonates beyond the treatment of skeletal diseases and presents a new tool for investigating bisphosphonate mechanism of action.

Figure 3:
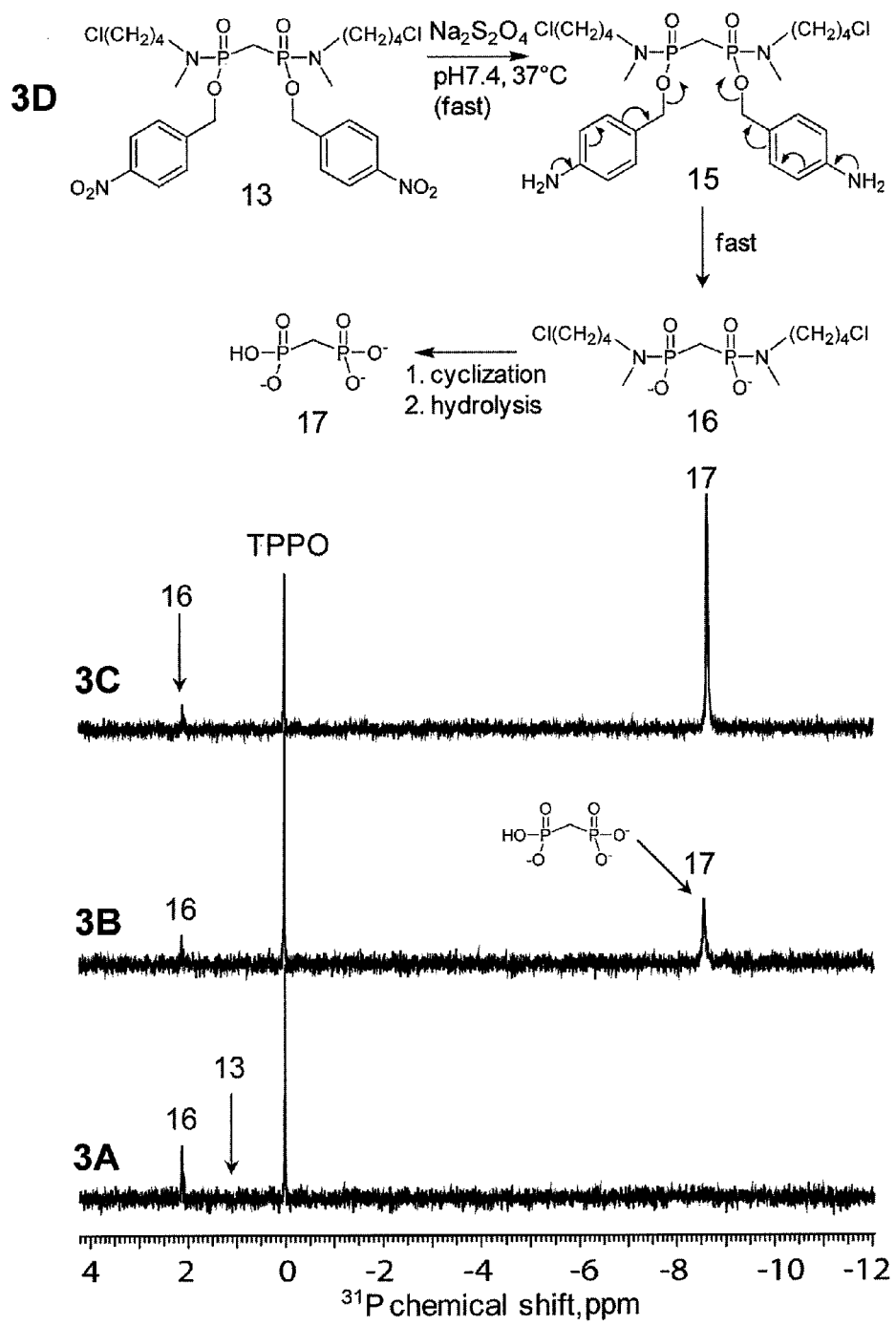
FIG. 3 shows a proposed mechanism for reductive activation of BP prodrug 13 and $^{31}$P NMR data supporting the mechanism Immediately following addition of dithionite to 13 (FIG. 3A); after 4 hours (FIG. 3B); following addition of authentic 17 (FIG. 3C) to reaction mixture shown in FIG. 3D.

The poor cellular uptake of bisphosphonates into soft tissues has limited their use in the treatment of extraskeletal diseases and detailed studies to elucidate the molecular mechanisms underlying the anticancer activity of this compound class. A more efficient strategy for the intracellular delivery of bisphosphonates was sought in order to realize the potential of this clinically-used compound class for the treatment of extraskeletal tumors. The bisphosphonamidate prodrugs described here are designed to be more membrane permeable than the corresponding free bisphosphonates and undergo efficient bioreductive activation to release either bisphosphate or clodronate intracellularly. For example, a bisphosphonamidate prodrug was rapidly activated to the corresponding bisphosphonate under model physiological conditions following chemical reduction of the nitroaryl delivery groups. Formation of free bisphosphonate as the only product is consistent with an activation mechanism that takes place via elimination, cyclization and P—N bond hydrolysis (FIG. 3). As no other bisphosphonate ester intermediates were observed in the $^{31}$P NMR spectrum in the systems studied, P—N bond hydrolysis prior to C—O cleavage is an unlikely activation pathway.

Without wishing to be bound by theory, it is believed that bisphosphonamidate prodrugs act by being metabolized intracellularly into active bisphosphonate compounds. However, intrinsic activity of the prodrugs themselves can not be excluded.

In some embodiments, membrane permeable bisphosphonamidate prodrugs 6 are designed to undergo rapid intracellular bioreduction to produce the corresponding hydroxylamine 7 (FIG. 2), which undergoes elimination through the aromatic ring and expulsion of phosphonamidate anion 8. The resulting increase in electron density of the phosphonamide nitrogen atom facilitates a cyclization reaction to produce the corresponding zwitterionic intermediate 9. Subsequent rapid P—N bond hydrolysis affords the unmasked phosphonate 10 in a similar manner to nucleotide release (Meyers et al., *Org. Lett.*, vol. 3, no. 23, pp. 3765-3768, 2001). The release of the second phosphonyl group is achieved in the same manner to give the fully unmasked bisphosphate, 11. Although it is difficult to predict the kinetics of activation, efficient release of the fully unmasked bisphosphonate is observed. An advantage of this strategy over existing bisphosphonate prodrug strategies is the requirement of a minimal number of enzymatic bioactivation steps to unmask multiple negative charges. As with the chemical deprotection of phosphoryl ester groups, removal of the first protective group is most often rapid, while removal of the second masking group is considerably slower, as a result of increased electron density at the phosphoryl leaving group and a slower rate of elimination (Cox et al., *Chem. Rev.*, vol. 64, no. 4, pp. 317-352, 1964). In some embodiments, the prodrug design incorporates a single nitroaryl delivery group at each phosphonyl group that is susceptible to rapid intracellular enzymatic activation by nitroreduction. The subsequent activation steps to release the fully unmasked bisphosphonate rely only upon the intrinsic chemical reactivity of the enzymatically reduced bisphosphonamidate 7, rather than subsequent, inefficient enzymatic activation events.

Figure 2:
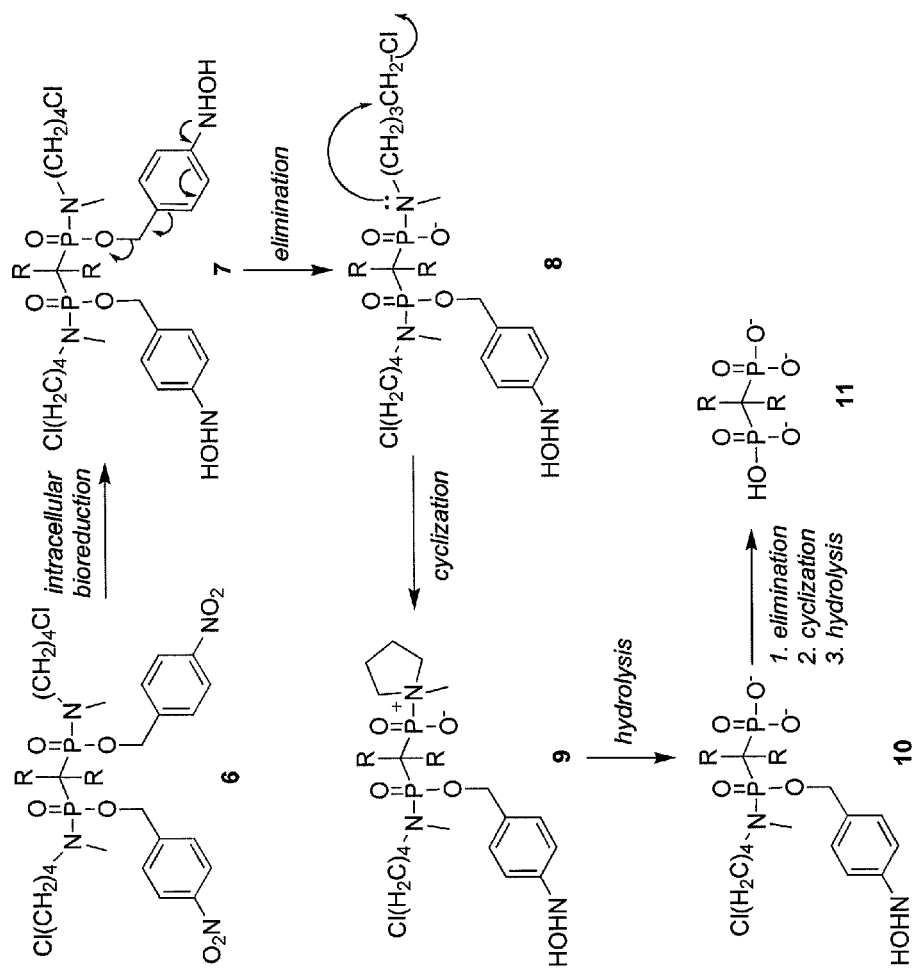
FIG. 2 shows a possible mechanism for intracellular bioreductive activation of bisphosphonamidate prodrugs (R=H, Cl).

In some embodiments, for example, bisphosphonamidate ester prodrugs may be activated by hydrolysis (enzymatically or non-enzymatically) to release phosphonamidate anion (analogous to 8 in FIG. 2). Alternatively, the compounds may be metabolized in vivo to an activated form that releases the phosphonamidate anion. For example, hydroxylation of an aromatic ring, followed by elimination as described above. Cyclization and hydrolysis of the phosphonamide follow to release the active bisphosphonate.

In other embodiments, for example, where $R^5$ and $R^6$ are O-acyl or N-acyl, an electron rich substituent may be released by hydrolysis (enzymatically or non-enzymatically) of the O-acyl or N-acyl group to produce an electron rich —OH or —NH substituent. The resulting substituent undergoes elimination through the aromatic ring, followed by expulsion of phosphonamidate anion (analogous to 8 in FIG. 2). Cyclization and hydrolysis of the phosphonamide follow to release the active bisphosphonate.

Figure 14:
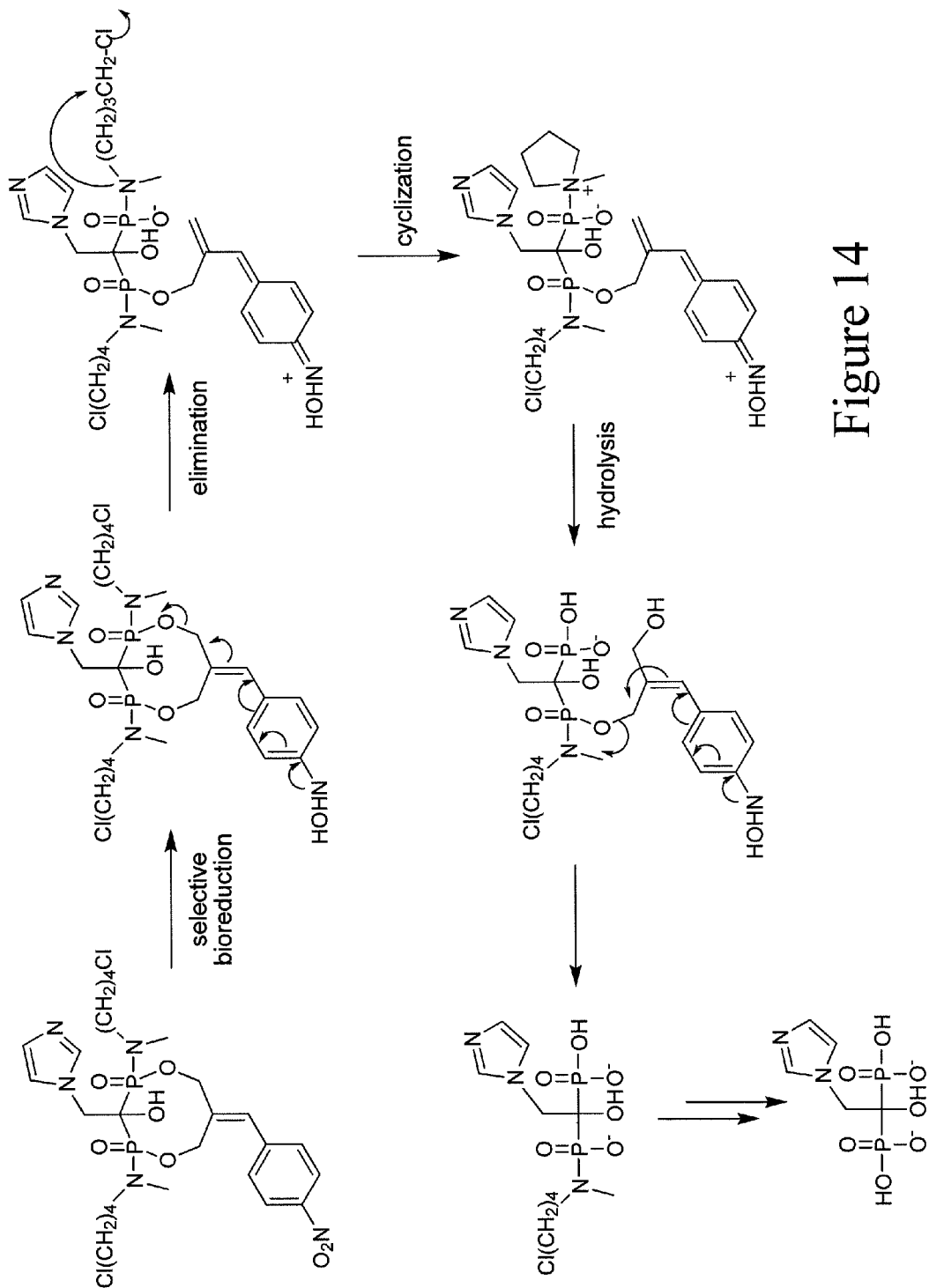
FIG. 14 shows a proposed mechanism for the activation and release of active bisphosphonate from cyclic bisphosphonamidate prodrug.
Figure 15:
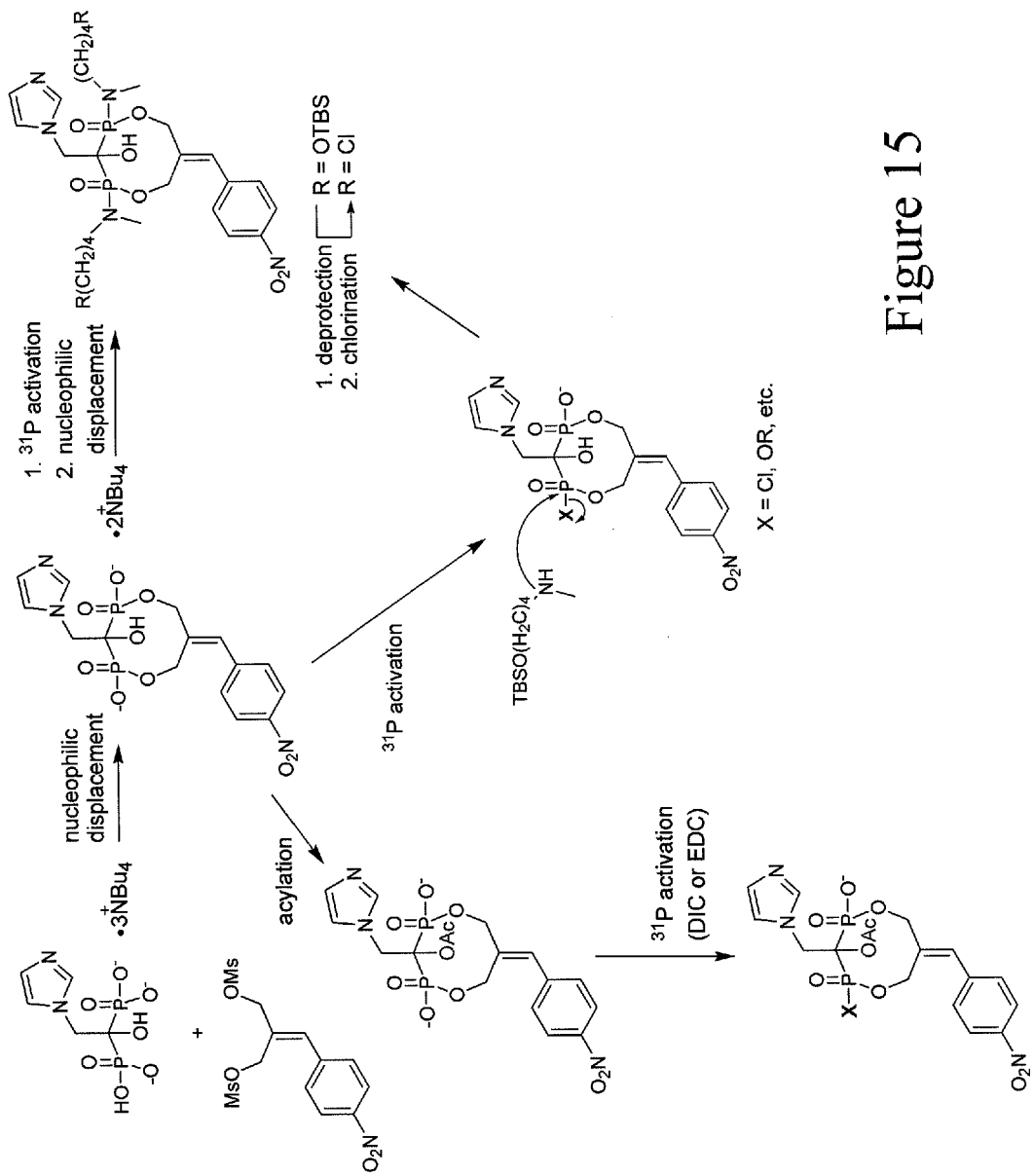
FIG. 15 shows the synthesis of cyclic bisphosphonamidate prodrug of zoledronate.
Figure 16:
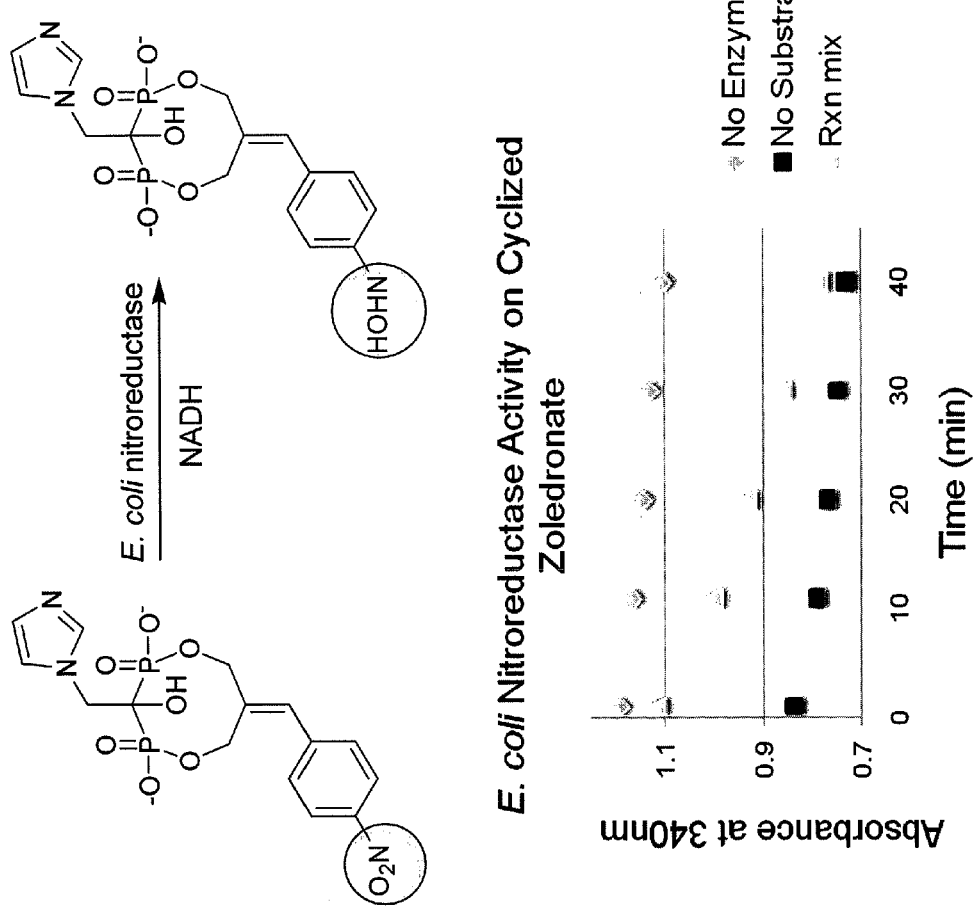
FIG. 16 suggests that a prodrug of zoledronate is a substrate for *E. coli* nitroreductase.
Figure 17:
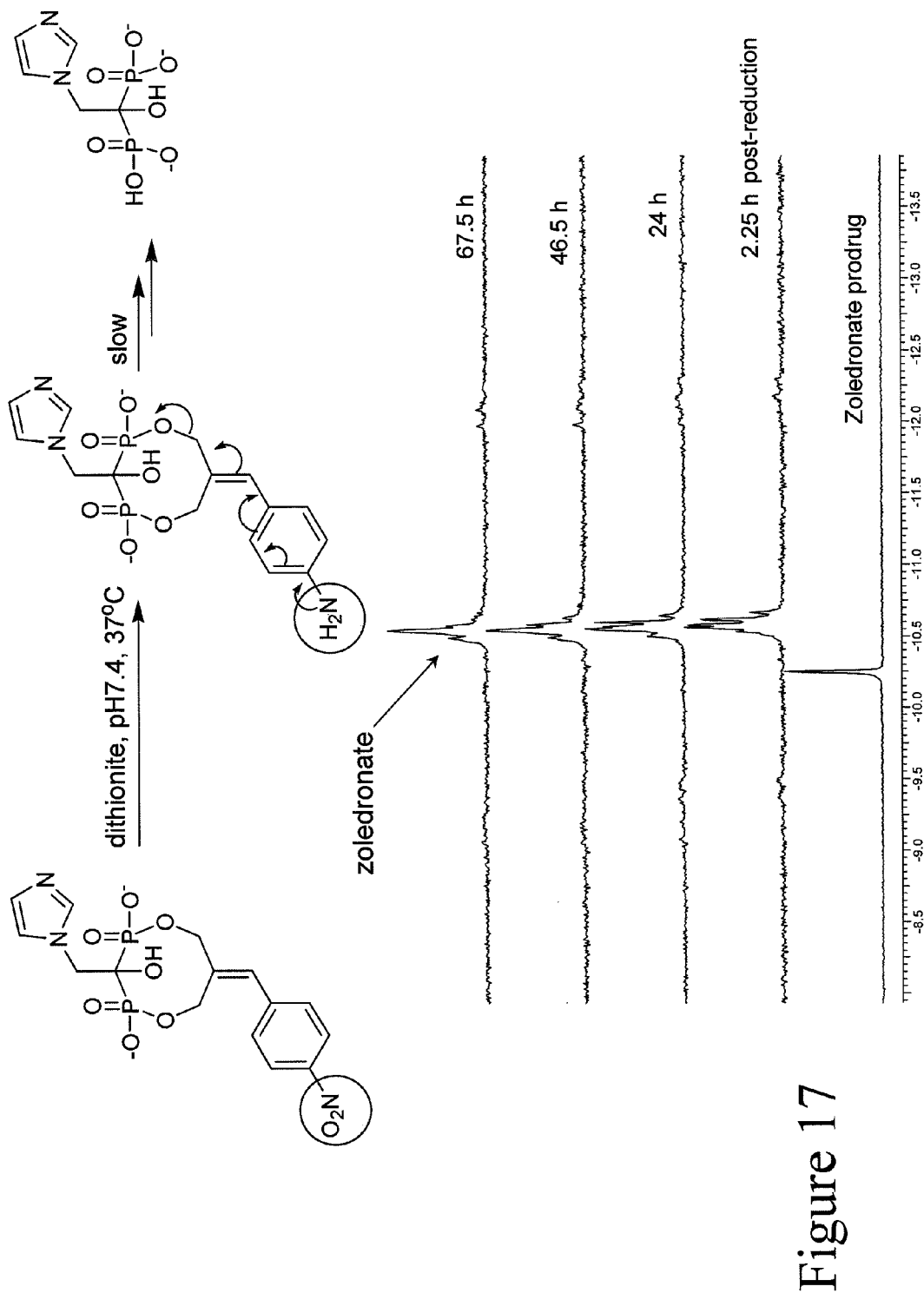
FIG. 17 shows $^{31}$P NMR detection of activation of cyclic bisphosphonate prodrug of zolendronate in the presence of dithionite.
Figure 18:
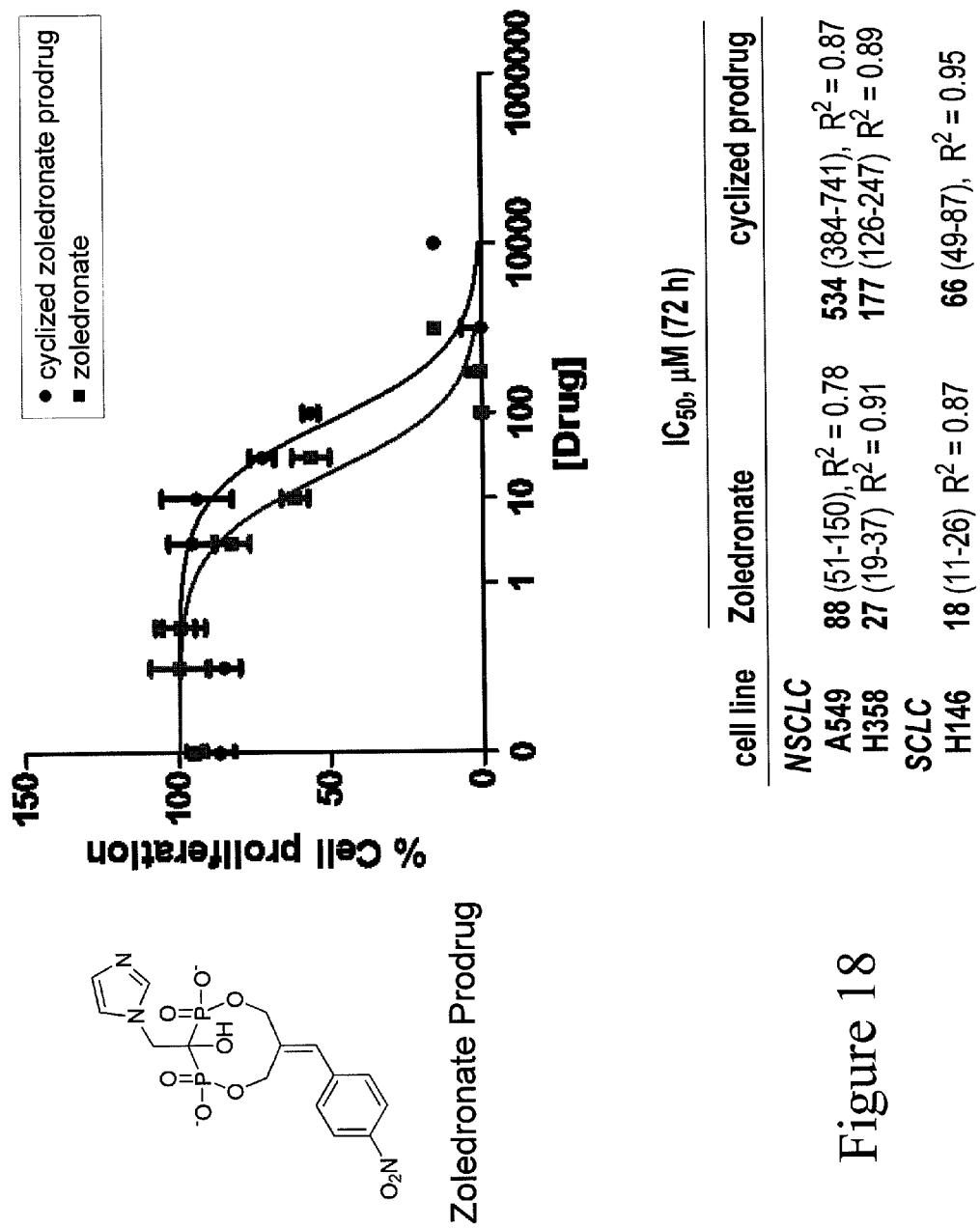
FIG. 18 shows the effect of cyclic bisphosphonamidate prodrug of zolendronate on SCLC and NSCLC compared to zolendronate.

In other embodiments, for example, cyclic bisphosphonamidate prodrugs, may release the active bisphosphonate by a single activation process (such as nitro reduction, or O-acyl or N-acyl hydrolysis), as shown in FIG. 14.

Bisphosphonamidate prodrug are developed on the basis of the highly efficient cyclization reaction of a halobutylamine masking group that results in release of nucleotides intracellularly. The chemistry has been extended to enable intracellular delivery of bisphosphonates, a class of clinically-used polyphosphonylated agents, which pose the additional chemical challenge of bearing more negative charges at physiologic pH.

A prodrug strategy has been developed to enhance membrane permeability of bisphosphonates through incorporation of biodegradable delivery groups and two halobutyl amine masking groups, which effectively mask the polyanionic charges (FIG. 2). The bisphosphonate design shown here extends the halobutyl phosphoramidate prodrug strategy developed for the intracellular delivery of nucleotides (Meyers et al., *Org. Lett.*, vol. 3, no. 23, pp. 3765-3768, 2001).

Additional differences highlight the unpredictability of the comparison between bisphosphonamidate prodrugs and nucleoside phosphoramidates. For example, the leaving group ability of the bisphosphonamidate anion following activation and elimination is unknown, and may exhibit substantially different behavior when compared to phosphoramidate prodrugs. Secondly, the kinetics of the cyclization reaction of the phosphonamidate to release chloride anion are unknown, and the presence of a P—C bond (lacking in phosphoramidate prodrugs) may substantially affect the reaction kinetics. The P—N bond of bisphosphonamidates is expected to exhibit different susceptibility to direct, acid-catalyzed hydrolysis when compared to phosphoramidate prodrugs. Finally, selective phosphorylation chemistry needed to produce either symmetrical or nonsymmetrical bisphosphonamidates, and new chemistry needed to synthesize an 8-membered ring of the cyclic phosphonamidate prodrugs, present bisphosphonamidates as a unique challenge.

Pharmaceutical Compositions

A further embodiment includes pharmaceutical compositions comprising any compound (BP prodrug), discussed herein or pharmaceutically acceptable salts thereof.

In certain embodiments the compositions may include one or more than one BP prodrug, and may further contain other suitable substances and excipients, including but not limited to physiologically acceptable buffering agents, stabilizers (e.g. antioxidants), flavoring agents, agents to effect the solubilization of the compound, and the like.

In certain embodiments, the composition may be in any suitable form such as a solution, a suspension, an emulsion, an infusion device, or a delivery device for implantation or it may be presented as a dry powder to be reconstituted with water or another suitable vehicle before use. The composition may include suitable parenterally acceptable carriers and/or excipients.

In certain embodiments, the compositions may comprise an effective amount of a BP prodrug in a physiologically-acceptable carrier. The carrier may take a wide variety of forms depending on the form of preparation desired for a particular route of administration. Suitable carriers and their formulation are described, for example, in Remington's Pharmaceutical Sciences by E. W. Martin.

In certain embodiments, the BP prodrug may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) or oral administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

In certain embodiments, the compositions may be in a form suitable for administration by sterile injection. To prepare such a composition, the compositions(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). For parenteral formulations, the carrier will usually comprise sterile water, though other ingredients, for example, ingredients that aid solubility or for preservation, may be included. Injectable solutions may also be prepared in which case appropriate stabilizing agents may be employed.

Formulations suitable for parenteral administration usually comprise a sterile aqueous preparation of the BP prodrug, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of systemic delivery or localized delivery. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

In certain embodiments, the compositions may be in a form suitable for oral administration. In compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like. For solid oral preparations such as, for example, powders, capsules and tablets, suitable carriers and additives include starches, sugars, diluents, granulating agents, lubricants, binders, disintegrating agents and the like. If desired, tablets may be sugar coated or enteric coated by standard techniques.

Compositions suitable for oral administration may be presented as discrete units such as capsules, cachets, tablets, or lozenges, each containing a predetermined amount of the BP prodrug as a powder or granules. Optionally, a suspension in an aqueous liquor or a non-aqueous liquid may be employed, such as a syrup, an elixir, an emulsion, or a draught. Formulations for oral use include tablets containing active ingredient(s) in a mixture with pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

A syrup may be made by adding the BP prodrug to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

In some embodiments, the composition may be in a form of nasal or other mucosal spray formulations (e.g. inhalable forms). These formulations comprise purified aqueous solutions of the BP prodrug with preservative agents and isotonic agents. Such formulations are preferably adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

In some embodiments, the composition may be in a form suitable for rectal administration. These formulations may be presented as a suppository with a suitable carrier such as cocoa butter, hydrogenated fats, or hydrogenated fatty carboxylic acids.

In some embodiments, the composition may be in a form suitable for transdermal administration. These formulations may be prepared by incorporating the BP prodrug in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, compositions of the invention may further include one or more accessory ingredient(s) selected from encapsulants, diluents, buffers, flavoring agents, binders, disintegrants, surface active agents, thickeners, lubricants, preservatives (including antioxidants), and the like.

In some embodiments, compositions may be formulated for immediate release, sustained release, delayed-onset release or any other release profile known to one skilled in the art.

In some embodiments, the pharmaceutical composition may be formulated to release the BP prodrug substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in the central nervous system or cerebrospinal fluid; (v) formulations that allow for convenient dosing, such that doses are administered, for example, once every one or two weeks; and (vi) formulations that target the site of a pathology. For some applications, controlled release formulations obviate the need for frequent dosing to sustain activity at a medically advantageous level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the BP prodrug is formulated with appropriate excipients into a pharmaceutical composition that, upon administration, releases the BP prodrug in a controlled manner. Examples include single or multiple unit tablet or capsule compositions, oil solutions, suspensions, emulsions, microcapsules, microspheres, molecular complexes, nanoparticles, patches, and liposomes.

In some embodiments, the composition may comprise a "vectorized" form, such as by encapsulation of the BP prodrug in a liposome or other encapsulate medium, or by fixation of the BP prodrug, e.g., by covalent bonding, chelation, or associative coordination, on a suitable biomolecule, such as those selected from proteins, lipoproteins, glycoproteins, and polysaccharides.

In some embodiments, the composition can be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents. Alternatively, the BP prodrug may be incorporated in biocompatible carriers, implants, or infusion devices.

Materials for use in the preparation of microspheres and/or microcapsules are, e.g., biodegradable/bioerodible polymers such as polyglactin, poly-(isobutyl cyanoacrylate), poly(2-hydroxyethyl-L-glutamine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly (caprolactone), poly(lactic acid), poly(glycolic acid) or poly (ortho esters) or combinations thereof).

Unless the context clearly indicates otherwise, compositions of all embodiments can comprise various pharmaceutically acceptable salts, ether derivatives, ester derivatives, acid derivatives, and aqueous solubility altering derivatives of the BP prodrug. Certain embodiments can comprise all individual enantiomers, diastereomers, racemates, and other isomer of compounds of the invention. The invention also includes all polymorphs and solvates, such as hydrates and those formed with organic solvents, of this compound. Such isomers, polymorphs, and solvates may be prepared by methods known in the art, such as by regiospecific and/or enantioselective synthesis and resolution, based on the disclosure provided herein.

Suitable salts of the compound include, but are not limited to, acid addition salts, such as those made with hydrochloric, hydrobromic, hydroiodic, perchloric, sulfuric, nitric, phosphoric, acetic, propionic, glycolic, lactic pyruvic, malonic, succinic, maleic, fumaric, malic, tartaric, citric, benzoic, carbonic cinnamic, mandelic, methanesulfonic, ethanesulfonic, hydroxyethanesulfonic, benzenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as sodium and potassium salts; alkaline earth metal salts, such as calcium and magnesium salts; and salts formed with organic or inorganic ligands, such as quaternary ammonium salts.

Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the compound of the present invention.

The formulation and preparation of such compositions are well known to those skilled in the art of pharmaceutical formulation. Formulations can be found in Remington: The Science and Practice of Pharmacy.

Methods

A further embodiment includes uses of compounds described herein for treating a disease in a subject. Embodiments include methods for treating a disease by administering a subject a therapeutically effective amount of a compound described herein.

The activity of the compound is based on the particular bisphosphonate. Any disease or disorder that may be treated by a bisphosphonate compound may be treated using the bisphosphonate prodrugs described herein because the bisphosphonamidate prodrugs described herein undergo intracellular degradation and release active bisphosphonate compound.

Examples of biologically active bisphosphonates include the compounds shown in FIG. 1, as well as the compounds shown below, all of which may be used to prepare bisphosphonamidate prodrugs of the invention.

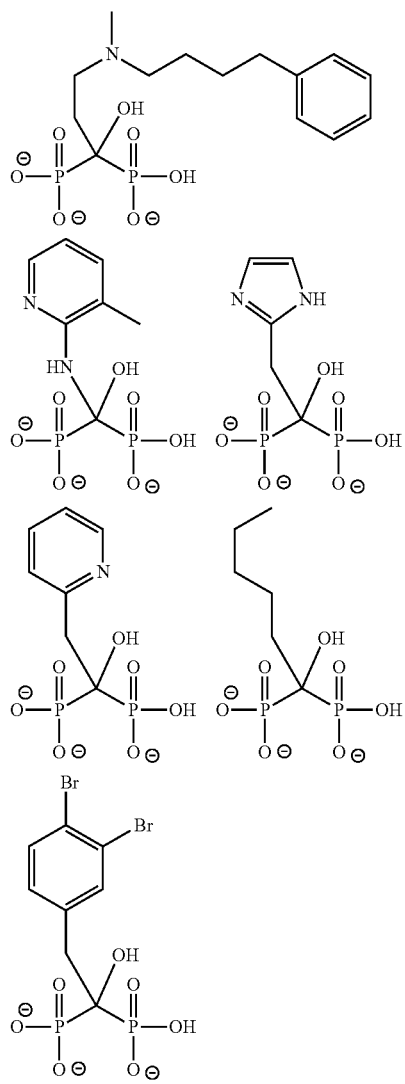

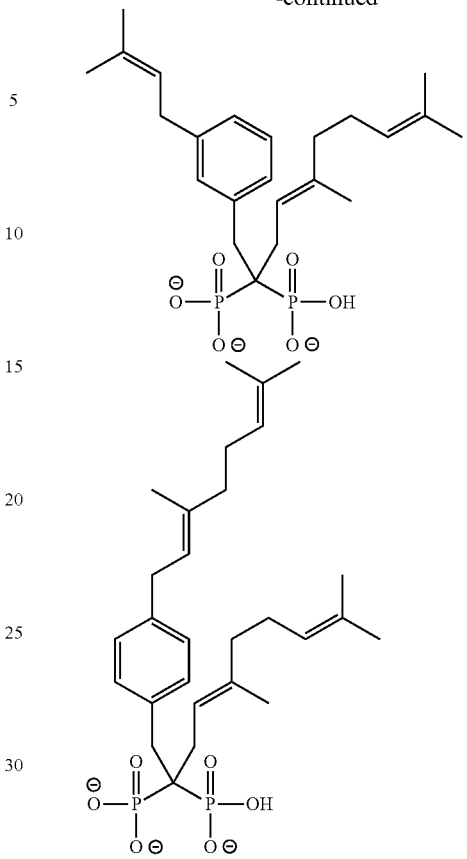

Exemplary methods include methods of treating hypercalcemia, osteoporosis or malignant bone disease. Examples of compounds that treat hypercalcemia, osteoporosis or malignant bone disease include nitrogen containing bisphosphonates, such as zoledronate, aledronate, or pamidronate. Many nitrogen containing bisphosphonates act by inhibiting isoprenoid biosynthesis by inhibiting farnesyl pyrophosphate synthase, ultimately inducing apoptosis. Other mechanisms may also be implicated.

Other exemplary methods include methods of treating hyperproliferative disorders. Hyperproliferative disorders are associated with under-regulated or out-of-control cellular replication, and include diseases such as cancer. Nitrogen-containing bisphosphonates and non-nitrogen-containing bisphosphonates are active against hyperproliferative disorders. Without wishing to be bound by theory, it is believed that non-nitrogen-containing bisphosphonates undergo conversion to non-hydrolyzable ATP analogs that ultimately inhibit cellular replication. For example, at effective concentrations, clodronate induces G1 cell cycle arrest, and may also affect mitochondrial function, which leads to cell death. However, other mechanisms may also be implicated.

Example hyperproliferative disorders include non-small cell lung cancer, small cell lung cancer, colon cancer, leukemia, CNS cancer, melanoma, ovarian cancer, renal cancer, bone metastases, prostate cancer, or breast cancer.

Still other exemplary methods include methods of treating infections by bacteria and non-bacterial parasites. For example, the majority of bacteria can synthesize isoprenoids by the methylerythritol phosphate pathway which includes farnesyl pyrophosphate synthase (Boucher and Doolittle, *Mol. Microbiol.*, vol 37 no. 4, pp. 703-716, 2000) and would be expected to be affected by bisphosphonate inhibitors of farnesyl pyrophosphate synthase. For example, *Bordetella* (e.g. *Bordetella pertussis*), *Campylobacter* (e.g. *Campylobacter jejuni*), *Chlamydia* (e.g. *Chlamydia* pneumonia, and *Chlamydia trachomatis*), *Clostridium* (e.g. *Clostridium difficile*), *Corynebacterium* (e.g. *Corynebacterium diphtheria*), *Escherichia* (e.g. *Escherichia coli*), *Haemophilus* (e.g. *Haemophilus influenza*), *Helicobacter* (e.g. *Helicobacter pylori*), *Mycobacterium* (e.g. *Mycobacterium leprae* and *Mycobacterium tuberculosis*), *Neisseria* (e.g. *Neisseria gonorrhoeae* and *Neisseria meningitides*), *Pseudomonas* (e.g. *Pseudomonas aeruginosa*), *Salmonella* (e.g. *Salmonella typhi* and *Salmonella typhimurium*), *Treponema* (e.g. *Treponema pallidum*), *Vibrio* (e.g. *Vibrio cholera*), *Yersinia* (e.g. *Yersinia pestis*) have been shown to have biosynthetic activity in the methylerythritol phosphate pathway or the genome contains sequences of genes within in this pathway.

Bisphosphonates are also effective against non-bacterial parasites. For example, bisphosphonates are active against *Plasmodium* (e.g. *P. falciparum*) and *Trypanosoma* (e.g. *T. brucei brucei, T. cruzi*, or *T. gondii*) parasites.

The compounds or compositions which are administered may be administered in any of many forms which are well-known to those of skill in the art. For example, they may be administered in any of a variety of art-accepted forms such as tablets, capsules, various injectable formulations, liquids for oral administration and the like, as suitable for the desired means of administration. The preparation which is administered may include one or more than one BP prodrug, and may further contain other suitable substances and excipients, including but not limited to physiological acceptable buffering agents, stabilizers (e.g. antioxidants), flavoring agents, agents to effect the solubilization of the compound, and the like. Administration of the compounds may be effected by any of a variety of routes that are well-known to those of skill in the art, including but not limited to oral, parenteral, intravenously, via inhalation, and the like. Further, the compounds may be administered in conjunction with other appropriate treatment modalities, for example, with nutritional supplements, agents to reduce symptoms and treatment with other agents.

In certain embodiments, the compositions may be administered orally. Administration to human patients or other animals is generally carried out using a physiologically effective amount of a compound of the invention in a physiologically-acceptable carrier. Suitable carriers and their formulation are described, for example, in Remington's Pharmaceutical Sciences by E. W. Martin.

In certain embodiments, the compositions may be administered systemically, for example, formulated in a pharmaceutically-acceptable buffer such as physiological saline. Routes of administration include, for example, subcutaneous, intravenous, intraperitoneally, intramuscular, or intradermal injections that provide continuous, sustained levels of the drug in the patient. Administration to human patients or other animals is generally carried out using a physiologically effective amount of a compound of the invention in a physiologically-acceptable carrier. Suitable carriers and their formulation are described, for example, in Remington's Pharmaceutical Sciences by E. W. Martin.

The formulation and preparation of such compositions are well known to those skilled in the art of pharmaceutical formulation. Formulations can be found in Remington: The Science and Practice of Pharmacy.

For example, compositions according to the invention may be provided in a form suitable for administration by sterile injection. To prepare such a composition, the compositions(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate).

The compositions may be provided in unit dosage forms (e.g., in single-dose ampules), or in vials containing several doses and in which a suitable preservative may be added. A composition of the invention may be in any suitable form such as a solution, a suspension, an emulsion, an infusion device, or a delivery device for implantation or it may be presented as a dry powder to be reconstituted with water or another suitable vehicle before use. The composition may include suitable parenterally acceptable carriers and/or excipients.

The amount of the BP prodrug to be administered varies depending upon the manner of administration, the age and body weight of the subject/patient, and with the subject's symptoms and condition. A compound is generally administered at a dosage that best achieves medical goals with the fewest corresponding side effects.

In some embodiments, the compositions including biologically active fragments, variants, or analogs thereof, can be administered by any suitable route including, but not limited to: oral, intracranial, intracerebral, intraventricular, intraperitoneal, intrathecal, intraspinal topical, rectal, transdermal, subcutaneous, intramuscular, intravenous, intranasal, sublingual, mucosal, nasal, ophthalmic, subcutaneous, intramuscular, intravenous, intra-articular, intra-arterial, sub-arachnoid, bronchial, lymphatic, and intra-uterille administration, and other dosage forms for systemic delivery of active ingredients.

Those of skill in the art will recognize that the precise quantity of such a compound to be administered will vary from case to case, and is best determined by a skilled practitioner such as a physician. For example, the amount may vary based on several characteristics of the patient, e.g. age, gender, weight, overall physical condition, extent of disease, and the like. Further, the individual characteristics of the compound itself (e.g. Ki, selectivity, $IC_{50}$, solubility, bioavailability, and the like) will also play a role in the amount of compound that must be administered. However, in general, the required amount will be such that the concentration of compound in the blood stream of the patient is about equal to or larger than the $IC_{50}$ or $K_i$ of the compound.

The composition may be administered parenterally by injection, infusion or implantation in dosage forms, formulations, or via suitable delivery devices or implants containing conventional, non-toxic pharmaceutically acceptable carriers and/or adjuvants. In one embodiment, the compositions are added to a retained physiological fluid, such as cerebrospinal fluid, blood, or synovial fluid. The compositions of the invention can be amenable to direct injection, application or infusion at a site of disease or injury.

In one approach, a composition of the invention is provided within an implant, such as an osmotic pump, or in a graft comprising appropriately transformed cells. Methods of introduction may also be provided by rechargeable or biodegradable devices. Various slow release polymeric devices have been developed and tested for the controlled delivery of drugs, including proteinaceous biopharmaceuticals. A variety of biocompatible polymers (including hydrogels), including both biodegradable and non-degradable polymers, can be used to form an implant for the sustained release of a bioactive factor at a particular target site.

Dosage

The administration of a compound may be by any suitable means that results in a concentration of the compound that, combined with other components, is effective in preventing, diagnosing, prognosing, ameliorating, reducing, or stabilizing a deficit or disorder.

Generally, the amount of administered agent of the invention will be empirically determined in accordance with information and protocols known in the art. Often the relevant amount will be such that the concentration of compound in the blood stream of the patient is about equal to or larger than the $IC_{50}$, or $EC_{50}$ of the compound. Typically agents are administered in the range of about 10 to 1000 μg/kg of the recipient. Other additives may be included, such as stabilizers, bactericides, and anti-fungals. These additives are present in conventional amounts.

Kits

Another embodiment includes kits, e.g., for the treatment, diagnosis, prophylaxis or prognosis of disease or injury. In one embodiment, the kit includes a composition according to the above embodiments containing an effective amount of a compound according to the above embodiments in unit dosage form. In some embodiments, the kit comprises an outer container or package. The kit can comprise a sterile container which contains the composition according to the above embodiments; such sterile containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

In certain kit embodiments, a composition according to the above embodiments is provided together with instructions for administering it to a subject. Instructions may include information about the use and effects of the composition. In one embodiment, the instructions will include at least one of the following: description of composition of the invention, dosage schedule and administration protocols, precautions, warnings, indications, counter-indications, overdosage information, adverse reactions, animal pharmacology, clinical studies, and/or references.

The instructions may be printed directly on a container (when present), or as a label applied to the container, or as a separate sheet, pamphlet, card, insert, or folder supplied in or with the container. Thus, the instructions may be a separate item in the kit, or be imprinted, embossed, molded or otherwise affixed to another item in the kit; instructions may be printed on an outer container and also included as an insert item in the kit.

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

Where a range of values is provided in the present application, it is understood that each intervening value, to the tenth of the unit of the lower limit unless the context clearly dictates otherwise, between the upper and lower limit of that range and any other stated or intervening value in that stated range, is encompassed within the invention. The end values of any range are included in the range.

Terms listed in single tense also include multiple unless the context indicates otherwise.

The examples disclosed below are provided to illustrate the invention but not to limit its scope. Other variants of the invention will be readily apparent to one of ordinary skill in the art and are encompassed by the appended claims. All publications, databases, and patents cited herein are hereby incorporated by reference for all purposes.

Methods for preparing the compounds of this invention are illustrated in the following Examples. Starting materials are made according to procedures known in the art or as illustrated herein. The following examples are provided so that the invention might be more fully understood. These examples are illustrative only and should not be construed as limiting the invention in any way.

EXAMPLES

Example 1

Design and Synthesis of Bisphosphonamidate Prodrugs

A bisphosphonamidate prodrug strategy for the intracellular release of bisphosphonates (BP) is shown and exemplified by application to bisphosphonic acid and the clinically-used NNBP clodronate. Results suggest bisphosphonamidate prodrugs undergo rapid activation to release the corresponding BP following reductive activation of nitroaryl delivery groups. Further, a remarkable enhancement in anticancer activity of two bisphosphonamidate prodrugs compared to the parent bisphosphonates in A549 cells is demonstrated.

Clodronate and bisphosphonate exhibited minimal activity against A549 cells up to 1 mM. The bisphosphonamidate prodrugs described here exhibit >250-fold increase in growth inhibitory activity A549 cells, compared to the free bisphosphonates. This remarkable enhancement in potency is likely due to increased cell permeability of the prodrug, which allows for a substantial increase in intracellular bisphosphonate concentration, although cytotoxicity of the prodrug itself cannot be ruled out. A partial growth inhibitory effect of the clodronate prodrug on A549 cells was observed as early as 24 h, and complete growth inhibition by the prodrug was observed by 48 and 72 h. The observed partial growth inhibitory effect at 24 h may reflect the dependence upon prodrug activation to release the corresponding bisphosphonate, the conversion of bisphosphonate to its active metabolite ($AppCH_2p$ or $AppCCl_2p$), and subsequent action of these metabolites on cellular target(s). T4 RNA ligase has been shown to effectively convert NNBPs to their ATP analogs (Sillero et al., *FEBS Letters*, vol. 580, no. 24, pp. 5723-5727, 2006). Both bisphosphonate and clodronate are known to be substrates of T4 RNA ligase with clodronate being converted to $AppCCl_2p$ more efficiently than the corresponding conversion of the non-chlorinated bisphosphonate to $AppCH_2p$. On this basis, intracellular conversion of bisphosphonate to $AppCH_2p$ is anticipated to be less efficient than the conversion of clodronate to $AppCCl_2p$. The observed 3-fold decrease in IC50 of 13 compared to 14 is consistent with this idea. Detailed studies to determine the kinetics of intracellular prodrug activation and clodronate metabolism are required to correlate these events with observed growth inhibitory activity.

To provide further evidence for the anticancer activity of bisphosphonamidate prodrugs 13 and 14, a complementary assay was performed to evaluate the effects of the bisphosphonamide prodrugs on cell viability. Absolute cell number was determined at each dose at 24, 48 and 72 h. Interestingly, 14 decreases the viability of A549 cells to just above 50% of control at higher doses over 24 h. However, a more pronounced effect on cell proliferation was observed at 24 h in the MTS assay. The difference between antiproliferative activity and effects on cell viability at 24 h suggests that 13 and 14 exert effects on metabolic activity, which leads to cell death over time. Taken together with the observation that somewhat higher prodrug concentrations are required for effects on cell viability, these results are consistent with a mechanism of action involving prodrug activation to the corresponding bisphosphonate and subsequent conversion to the non-hydrolyzable ATP analog.

The more potent clodronate prodrug 14 was selected for cell cycle analysis studies. PI and flow cytometry analysis of A549 cells treated with the clodronate prodrug over 72 h suggested $G_1$ cell cycle arrest of A549 cells at low concentrations of prodrug 14. $G_1$ cell cycle arrest was unequivocally confirmed in nocodazole-treated cells where an obvious shift from nocodazole-induced $G_2$ arrest to $G_1$ arrest occurred in the low micromolar range of prodrug 14. $G_1$ cell cycle arrest correlates with the antiproliferative activity of this compound, suggesting prodrug 14 affect mitochondrial function, which leads to cell cycle arrest and eventually cell death.

All $^{31}$P and $^1$H NMR spectra were acquired on a 400 mHz Varian NMR. $^{31}$P shifts were recorded in parts per million and referenced to triphenylphosphine oxide (TPPO) as the coaxial reference in either benzene or benzene-$d_6$. $^1$H chemical shifts are reported in parts per million from tetramethylsilane. All reactions were carried out under argon unless otherwise noted. Methylene chloride and diisopropylethylamine were obtained from commercial sources and distilled prior to use. A549 cells were maintained in 1640 RMPI with 10% FBS, 1% pen/strep, 1% Glutamate, and 1% sodium pyruvate. N-Methyl-N-(4-chlorobutyl)amine hydrochloride was synthesized as previously described (Meyers et al., *Org. Lett.*, vol. 3, no. 23, pp. 3765-3768, 2001).

Synthesis

Bisphosphonamide prodrugs were synthesized as shown in Scheme 1. For example, des-chloro bisphosphonamide 13 was prepared via a two-step, one-pot synthesis. N-Methyl-N-chlorobutylamine hydrochloride was prepared as previously described (Meyers et al., *Org. Lett.*, vol. 3, no. 23, pp. 3765-3768, 2001). Coupling of N-methyl-N-chlorobutylamine substituents to methylenebis(phosphonic dichloride) in the presence of DIPEA was monitored using $^{31}$P NMR. Complete conversion to intermediate 12 was confirmed by the disappearance of the starting bisphosphonic acid at −9 ppm (relative to TPPO) and appearance of a new $^{31}$P resonance at 6.2 ppm. Treatment of the corresponding phosphonamide dichloride 12 with nitrobenzyl alcohol in the presence of DIPEA and a nucleophilic catalyst (DMAP) afforded bisphosphonamide prodrug 13. Chlorination of bisphosphonamide 13 with sodium hypochlorite provided clodronate prodrug 14.

Scheme 1. Synthesis of prodrugs 13 and 14.

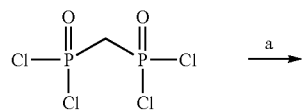

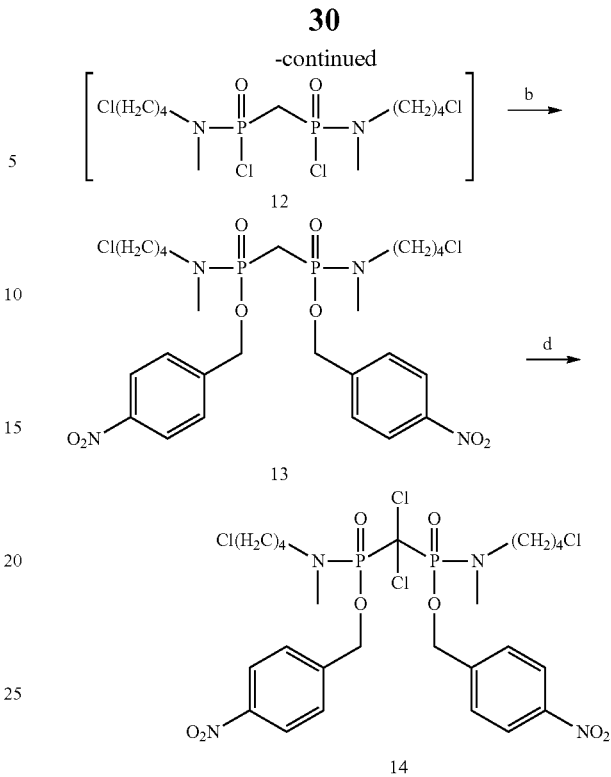

Reaction conditions: (a) N-Methyl-N-(4-chlorobutyl)amine hydrochloride, DIPEA, CH$_2$Cl$_2$, 0° C.; (b) Nitrobenzyl alcohol, DIPEA, DMAP, rt.; (d) NaOCl, benzyltriethyl ammonium chloride, CCl$_4$, MeOH.

Bisphosphonamide 13. Methylenebis(phosphonic dichloride) (0.466 g, 1.87 mmol) and N-methyl-N-(4-chlorobutyl)amine hydrochloride (0.589 g, 3.73 mmol) were dissolved in CH$_2$Cl$_2$ (7.48 ml) and cooled to 0° C. with stirring under an Ar atmosphere. DIPEA (1.56 ml, 8.98 mmol) was added dropwise. The reaction mixture was allowed to warm to room temperature, and stirring was continued for 2 h. Nitrobenzyl alcohol (1.43 g, 9.35 mmol) was added to the reaction mixture in one portion. In a separate flask under an Ar atmosphere, DMAP (0.228 mg, 1.87 mmol) was dissolved in CH$_2$Cl$_2$ (0.2 ml) and DIPEA (0.782 ml, 4.49 mmol), and the resulting mixture was added dropwise to the reaction mixture at room temperature. The reaction mixture was stirred at room temperature for 4 hours and then washed with saturated NH$_4$Cl (1×2 mL). The organic layers were combined, dried over NaSO$_4$ and concentrated under reduced pressure. Purification was accomplished by column chromatography (1:99, MeOH/ethyl acetate) to afford 13 as a pale yellow oil 32% yield. $^{31}$P NMR (CDCl$_3$) δ 0.87 (s, 11.5); 0.762 (s, 6.01); $^1$H NMR (CDCl$_3$) δ 8.20 (d, 4H); 7.59 (d, 4H); 5.20 (m, 2H); 4.90 (m, 2H); 3.50 (t, 4H); 3.18 (m, 2H); 2.95 (m, 2H); 2.60 (d, 6H); 2.4 (t, 2H); 1.65 (m, 8H).

Bisphosphonamide clodronate prodrug 14. Bisphosphonamide 13 (0.350 g, 0.536 mmol) was dissolved in CCl$_4$ (1.2 ml) and MeOH (0.6 ml). Benzyltriethylammonium chloride (0.054 g, 0.236 mmol) was added in one portion. 10% NaOCl solution (1.8 mL) was added with stirring. The reaction was monitored by $^{31}$P NMR over a period of 4 hours until completion. The reaction was quenched with saturated NH$_4$Cl solution (2 mL), and the product was extracted using CH$_2$Cl$_2$ (2×0.5 ml). The chlorinated product was purified by column chromatography (100% ethyl acetate to 5:95 MeOH/ethyl acetate) to afford 14 as a pale yellow oil (60% yield). $^{31}$P NMR (CDCl$_3$) δ −9.53 (s); $^1$H NMR (CDCl$_3$) δ 8.25 (2d, 4H); 7.60 (2d, 4H); 5.40 (m, 2H); 5.30 (m, 2H); 3.55 (m, 4H); 2.85 (m, 6H); 1.7 (br m, 8H).

Confirmation of Bisphosphonamidate Activation.

To confirm the release of a fully unmasked bisphosphonate following reduction of the bisphosphonamidate nitrobenzyl ester, bisphosphonamidate prodrug 13 was subjected to chemical reduction by dithionite under model physiologic conditions, and the subsequent reactions were monitored using $^{31}$P NMR (FIG. 3). Upon solubilization and reduction of 13, a resonance appearing at +2 ppm (relative to TPPO) was observed in the $^{31}$P NMR spectrum (FIG. 3A). Conversion of this peak to a new resonance at −8.5 ppm (FIG. 3B) was observed, and is consistent with elimination and release of the bisphosphonate 17. Confirmation of bisphosphonate release was accomplished by comparison to authentic bisphosphonate 17 (FIG. 3C).

Example 2

Activity of Bisphosphonamidate Prodrugs

In vitro Cell Proliferation Assays.

Cell proliferation was determined using the CellTiter 96 Aqueous One Solution Cell Proliferation Assay MTS assay. A549 NSCLC cells were plated at 1.5×10$^3$ cells per well in flat bottom 96 well plates in 99 μL of media and allowed to adhere overnight. The drugs were serially diluted in 100% DMSO. For each drug treatment group, 1 μL of a 100× stock solution was added to each well for a final DMSO concentration of 1%. Cells were treated for 24, 48 or 72 hours. Cells were incubated with MTS dye (20 μL well$^{-1}$) for 40 min to 2 h. Absorbance at 490 nm was determined using a SpectraMax M2 (Molecular Devices) plate reader. The percent cell proliferation was calculated by converting the experimental absorbance to percentage of control, which was then plotted vs. drug concentration. The IC$_{50}$ values were determined using a non-linear dose-response analysis in GraphPad Prism version 4.0. The IC$_{50}$ is defined as the concentration of drug needed to cause a 50% decrease in proliferation compared to vehicle control.

Figure 4:
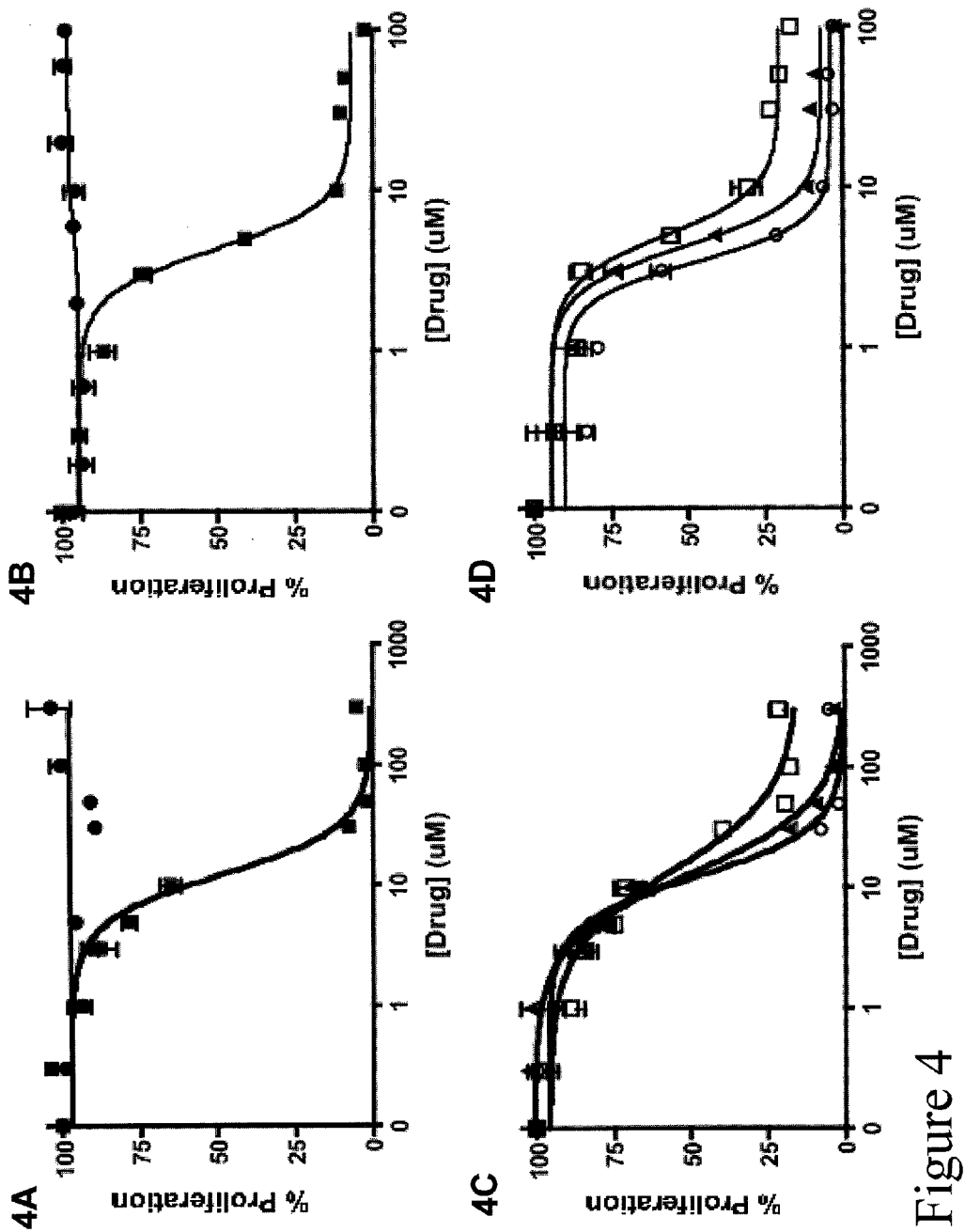
FIG. 4 shows the effect of bisphosphonate prodrug 13 and clodronate prodrug 14 on proliferation, determined using the MTS assay. Results displayed as % of control.

Clodronate has shown little or no antiproliferative effects against multiple cells lines, due in part to low membrane permeability. Bisphosphonamidates 13 and 14 are fully masked and are expected to have increased cell permeability. Both 13 and 14 exhibit potent activity against A549 NSCLC cells in vitro (FIG. 4) as determined by the MTS cell proliferation assay. Dose-response curves were generated using drug concentrations ranging from 0.2 μM to 300 μM and cell proliferation was measured at 24, 48 and 72 hours after drug treatment (FIG. 4, Table 1). Consistent with published reports (Knight et al., *Anticancer Drugs*, vol. 16, no. 9, pp. 969-976, 2005), clodronate does not exhibit a detectable growth inhibitory effect at concentrations up to 1 mM against the growth of A549 cells. In contrast, clodronate prodrug 14 and bisphosphonate prodrug 13 exhibit remarkably enhanced activity with IC$_{50}$ values of 5.2±1 μM and 15.2±0.4 μM, respectively, at 48 h (FIG. 4A, 4B).

TABLE 1

In vitro effects of 13 and 14 on A549 NSCLC cells

| | 13 | | 14 | |
|---|---|---|---|---|
| Time (h) | IC$_{50}$ (μM)[b] | EC$_{50}$ (μM)[c] | IC$_{50}$ (μM)[b] | EC$_{50}$ (μM)[c] |
| 24 | 17 ± 4 | n.d.[a] | 7.6 ± 3 | n.d.[a] |
| 48 | 15 ± 0.4 | 24 ± 4 | 5.2 ± 1 | 19 ± 4 |
| 72 | 13 ± 1 | 25 ± 4 | 4.4 ± 2 | 16 ± 1 |

[a]The viability of A549 cells did not decrease by 50% after 24 h of treatment with 13 or 14.
[b]IC50 is concentration of 13 or 14 that decreased cell proliferation by 50% compared to control.
[c]EC50 is the concentration of 13 or 14 that decreased cell number by 50% compared to control.

In Vitro studies of Clodronate Prodrug in Melanoma

Figure 7:
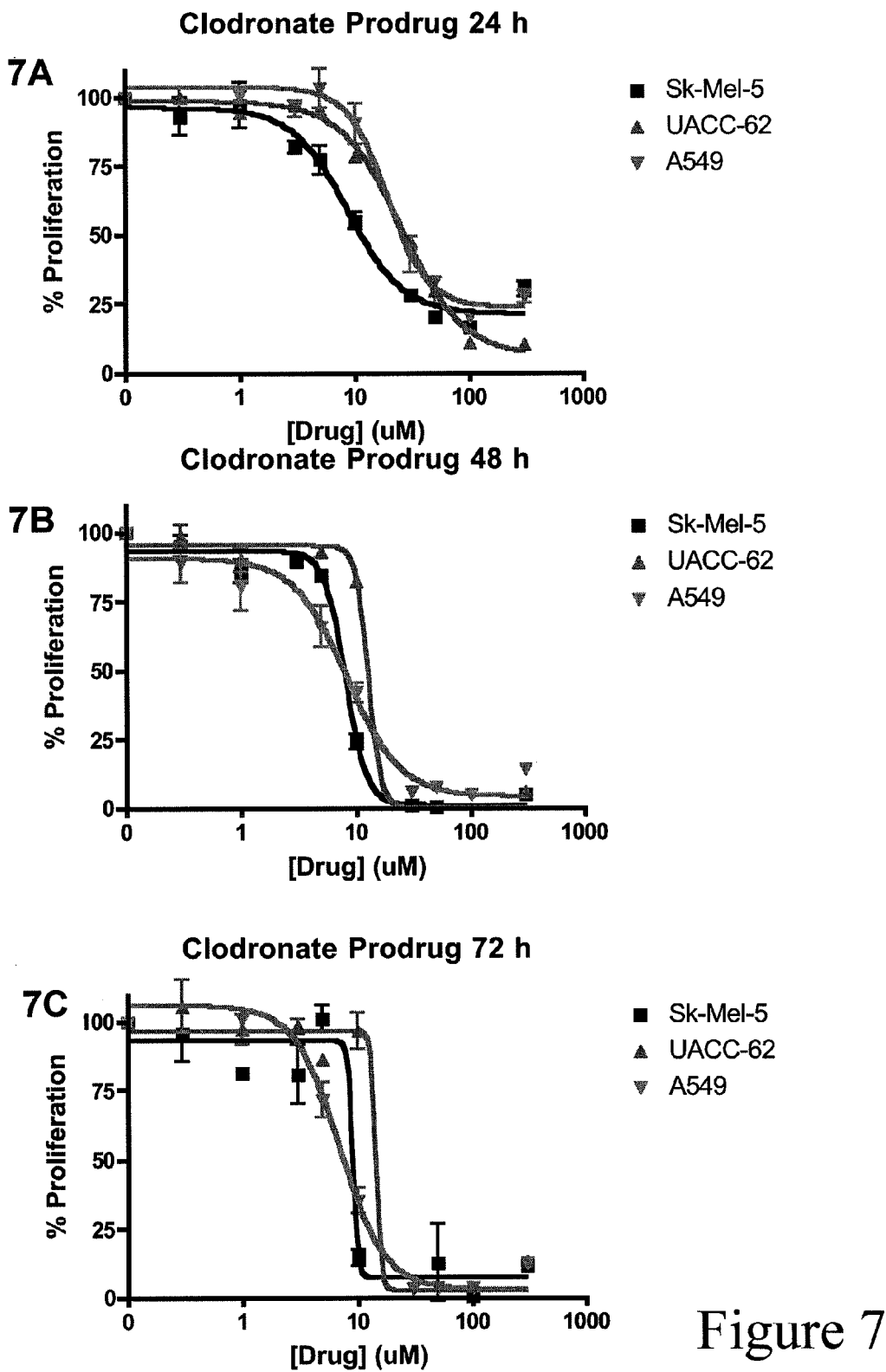
FIG. 7 shows the effect of 14 on proliferation of melanoma cells (UACC-62 and Sk-Mel-5).

Cell proliferation was determined using the CellTiter 96 Aqueous One Solution Cell Proliferation Assay MTS assay. A549 NSCLC cells were plated at 1.5×10$^3$ cells per well in flat bottom 96 well plates in 99 μL of media and allowed to adhere overnight. SK-MeI-5 melanoma cells were plated at 6.3×10$^3$ cells per well and UACC-62 melanoma cells were plated at 3×10$^3$ cells per well in 99 μL of media and they were allowed to adhere overnight. The drugs were serially diluted in 100% DMSO. For each drug treatment group, 1 μL of a 100× stock solution was added to each well for a final DMSO concentration of 1%. Cells were treated for 24, 48 or 72 hours. Cells were incubated with MTS dye (20 μL well$^{-1}$) for 40 min to 2 h. Absorbance at 490 nm was determined using a SpectraMax M2 (Molecular Devices) plate reader. The percent cell proliferation was calculated by converting the experimental absorbance to percentage of control, which was then plotted vs. drug concentration. The IC$_{50}$ values were determined using a non-linear dose-response analysis in GraphPad Prism version 4.0. The IC$_{50}$ is defined as the concentration of drug needed to cause a 50% decrease in proliferation compared to vehicle control as shown in FIG. 7.

Cell Cycle Analysis.

Figure 5:
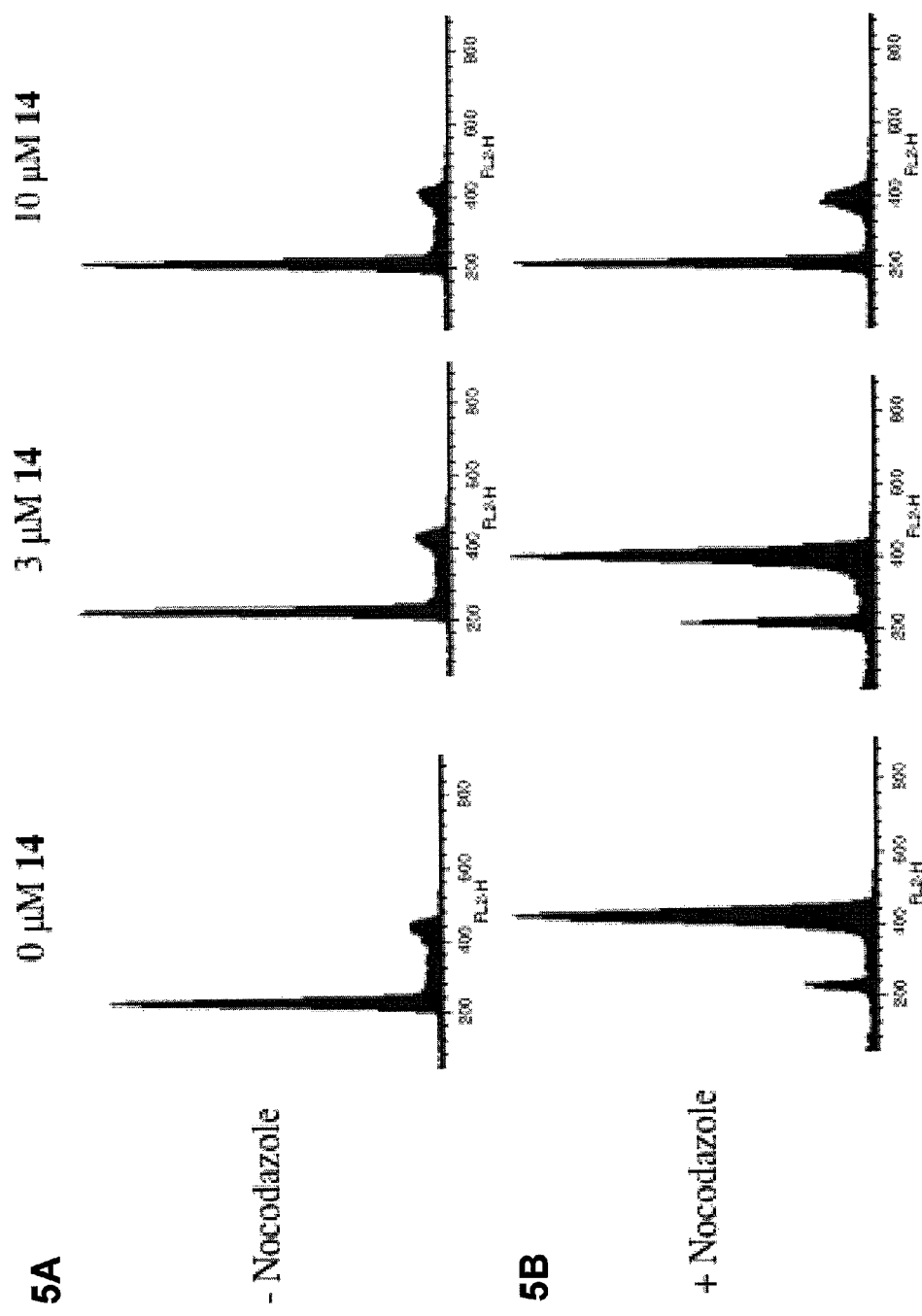
FIG. 5 shows the effect of clodronate prodrug (14) on cell cycle, determined using the PI and FACS analysis. Top row (FIG. 5A) shows A549 cells treated with 0, 3, and 10 μM of 14 for 72 h. Bottom row (FIG. 5B) shows A549 cells treated with 0, 3, and 10 μM of 14 for 72 h and nocodazole for the final 24 h. In the nocodazole-treated cells, accumulation of cells in G1 phase is evident at 3 and 10 uM of 14.

PI and flow cytometry analysis were performed to study the effects of prodrug 14 on cell cycle. Cell cycle analysis of cells treated with 0, 3, or 10 μM 14 for 72 h suggested cell cycle arrest with low micromolar concentrations of 14 (30 μM, data not shown). Support of G$_1$ cell cycle arrest was obtained through flow cytometry analysis of cells treated with 0, 3, or 10 μM 14 for 72 h, and with nocodazole treatment for the last 24 h of prodrug exposure. Nocodazole is a microtubulin polymerization inhibitor, known to cause G$_2$ cell cycle arrest. In the absence of prodrug 14, nocodazole-induced G$_2$ arrest is evident (FIG. 5B). However, in the presence of prodrug, a marked accumulation of cells in G$_1$ is observed as low as 3 μM, indicating G$_1$ cell cycle arrest caused by prodrug 14.

Briefly, A549 NSCLC cells were plated at 6.7×10$^4$ cells per well in flat bottom 6-well plates. Cells were dosed as described above. At 24, 48 or 72 hours following drug treatment, the media was collected, and the cells were washed with 1 mL PBS. Each well was trypsinized with 600 μL trypsin for 3-5 min. The trypsin reaction was quenched with an equal volume of media. All supernatants and washes were combined and centrifuged at 1,500 rpm for 5 min. Supernantant was decanted, and the cells were washed with 2 mL 1% FBS/PBS. Cells were centrifuged at 1,500 rpm for 5 min, and the supernatant was decanted. Cells were resuspended in 1 mL cold PBS, fixed in cold 70% ethanol and incubated at 4° C. for at least 30 min. Cells were centrifuged at 1,500 rpm for 5 min, washed with 1% FBS/PBS, and resuspended in 1 mL of 2:1 1% FBS in PBS/phosphate citric acid buffer (pH 7.8). Cells were incubated at room temperature for 5 min, then spun at 1,500 rpm for 5 min. The supernatant was decanted, the cells were resuspended and incubated in 300 μL PBS/FBS/PURNase solution (10 μg/mL propidium iodide and 3 K.U. of RNase A) for 30 mM at 37° C. Flow cytometry was performed to analyze DNA content, collecting ten thousand PI positive gated events per sample.

Annexin V Staining and Flow Cytometry

Velcade, a proteosome inhibitor, was used as a positive control. A549 NSCLC cells were plated at $9 \times 10^4$ cells per well in a 6 well plate in 2.93 mL media. The cells were incubated overnight at 37° C. 5% $CO_2$. For each drug treatment group, 30 μL of a 100× stock solution was added to each well for a final DMSO concentration of 1%. Cells were treated for 48 hours. Cells were washed with 0.5 mL PBS. 0.5 mL 0.05 trypsin was added to each well and the cells were incubated at 37° C. for 3-5 min. The trypsin was quenched with 0.5 mL media and the cells were transferred to 15 mL conical tubes. The cells were counted using trypan blue and a hemocytometer. The cells were centrifuged at 1,000 rpm for 5 min. Cells were washed 2× with PBS, centrifuging at 1,000 rpm for 5 min after each wash and resuspended in 1× binding buffer (10 mM hepes, 140 mM NaCl, 2.5 mM $CaCl_2$) at a density of $1 \times 10^5$ per 100 μL. Transfer 100 mL of cells to a 5 mL FACS tube. Five 5 μL of Annexin V antibody and 5 μL of 7-AAD were added. The cells were incubated for 15 min at room temperature in the dark. 400 μL of binding buffer was added, and analyzed by flow cytometry within 1 h. Results are shown in FIG. 20.

In Vitro Cell Count—Trypan Blue Assay

A549 NSCLC cells were plated at $1.7 \times 10^4$ cells per well in flat bottom 12-well plates. Cells were dosed as described above. At 24, 48 or 72 hours following drug treatment, the media was collected, and the cells were washed with 200 μL PBS. Each well was trypsinized with 200 μL trypsin for 3-5 min. The trypsin reaction was quenched with an equal volume of media. All supernatants and washes were combined and spun at 1,500 rpm for 5 min. Supernatant was decanted, and the cells were resuspended in 200 μL media. The cells were diluted 1:1 in 0.04% trypan blue and counted using a cytometer. The absolute number of cells was determined at each drug concentration. The cell number for each concentration was converted to percent of control for each time point, and plotted using GraphPad Prism 4.0. The $EC_{50}$ was calculated as the concentration of drug that caused a 50% decrease in number of cells compared to control.

Figure 6:
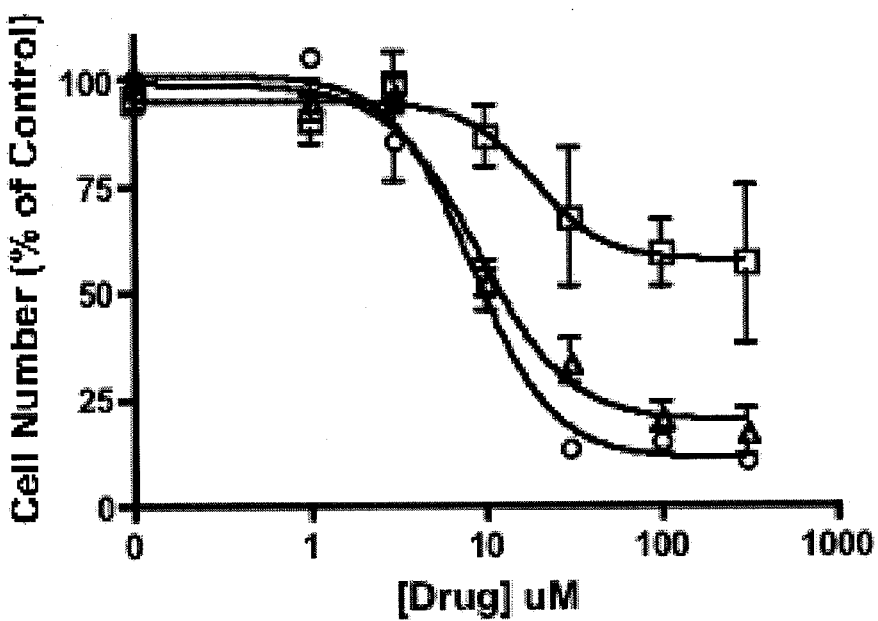
FIG. 6 shows the effect of 14 on cell viability of NSCLC cells. Absolute cell number determined using trypan blue. The decrease in number of NSCLC cells by 14 at 24 ( ), 48 (▲), 72 (●) h is shown in FIG. 6A. Crystal violet staining of A549 NSCLC cells treated with 14 for 72 h is shown in FIG. 6B.
Figure 6:
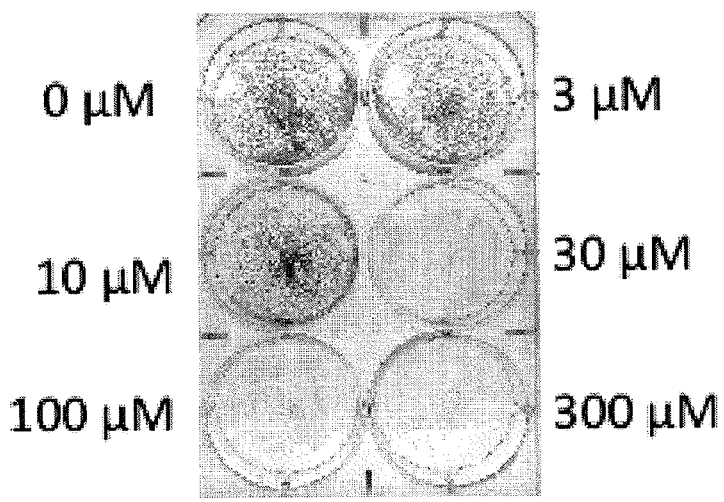

In order to correlate the growth inhibitory effects of 13 and 14 with cell viability, absolute cell number at varying drug concentration was determined using a trypan blue exclusion assay. The number of viable cells at each dose was determined at 0, 24, 48 and 72 hours following drug treatment and plotted as a percent of control (FIG. 6A). The $EC_{50}$ of 14 determined at 48 h is 19±4 μM, ~1.6 fold higher than its $IC_{50}$ determined by the MTS assay (Table 1). A similar difference in the effects of 14 on cell viability versus inhibition of proliferation was observed after a 72 hour drug treatment. Interestingly, at 24 h, cell viability was reduced by only 57% at the highest drug concentration tested; therefore an $EC_{50}$ was not determined. In parallel, viable cells were stained with crystal violet at 72 h following drug treatment to further demonstrate the marked reduction in cell viability upon treatment with clodronate prodrug 14 (FIG. 6B). In order to confirm the loss of viable cells, cells treated with 14 for 72 h, were washed and allowed to growth in fresh media without drug for 48 h. No new growth was observed in the wells that were originally treated with 30, 100 and 300 μM 14. Prodrug 13 affected cell viability in a similar manner with an $EC_{50}$ at 48 h that was ~3.6 fold greater than its IC50 determined using the MTS assay.

Crystal Violet Assay.

A549 NSCLC cells were plated at $1.7 \times 10^4$ cells per well in flat bottom 6-well plates. Cells were dosed as described above. Cells were analyzed at 24, 48 and 72 hours. The media was removed, and the cells were washed twice with PBS. The cells were then stained with crystal violet solution (1 mL well$^{-1}$, 0.5% crystal violet in 95% EtOH) for 5 to 15 min. The stain was removed, and the plates were rinsed with cold water and dried at room temperature. Results are shown in FIG. 6B.

Effect of Drug Treatment Time on Prodrug Effectiveness

Cell proliferation was determined using the CellTiter 96 Aqueous One Solution Cell Proliferation Assay MTS assay. A549 NSCLC cells were plated at $1.5 \times 10^3$ cells per well in flat bottom 96 well plates in 99 μL of media and allowed to adhere overnight. The drugs were serially diluted in 100% DMSO. For each drug treatment group, 1 μL of a 100× stock solution was added to each well for a final DMSO concentration of 1%. Cells were treated for 2, 24, or 48 under normoxic or hypoxic (1-3% oxygen) conditions. Following 2 or 24 h, media containing drug was removed, the cells were washed 1× with fresh media, and 100 μL fresh media was added to each well. Cells were then allowed to grow for an additional 46 or 24 h in drug free media. After 48 h, cells were incubated with MTS dye (20 μL well$^{-1}$) for 40 min to 2 h. Absorbance at 490 nm was determined using a SpectraMax M2 (Molecular Devices) plate reader. The percent cell proliferation was calculated by converting the experimental absorbance to percentage of control, which was then plotted vs. drug concentration. The $IC_{50}$ values were determined using a non-linear dose-response analysis in GraphPad Prism version 4.0.

Figure 8:
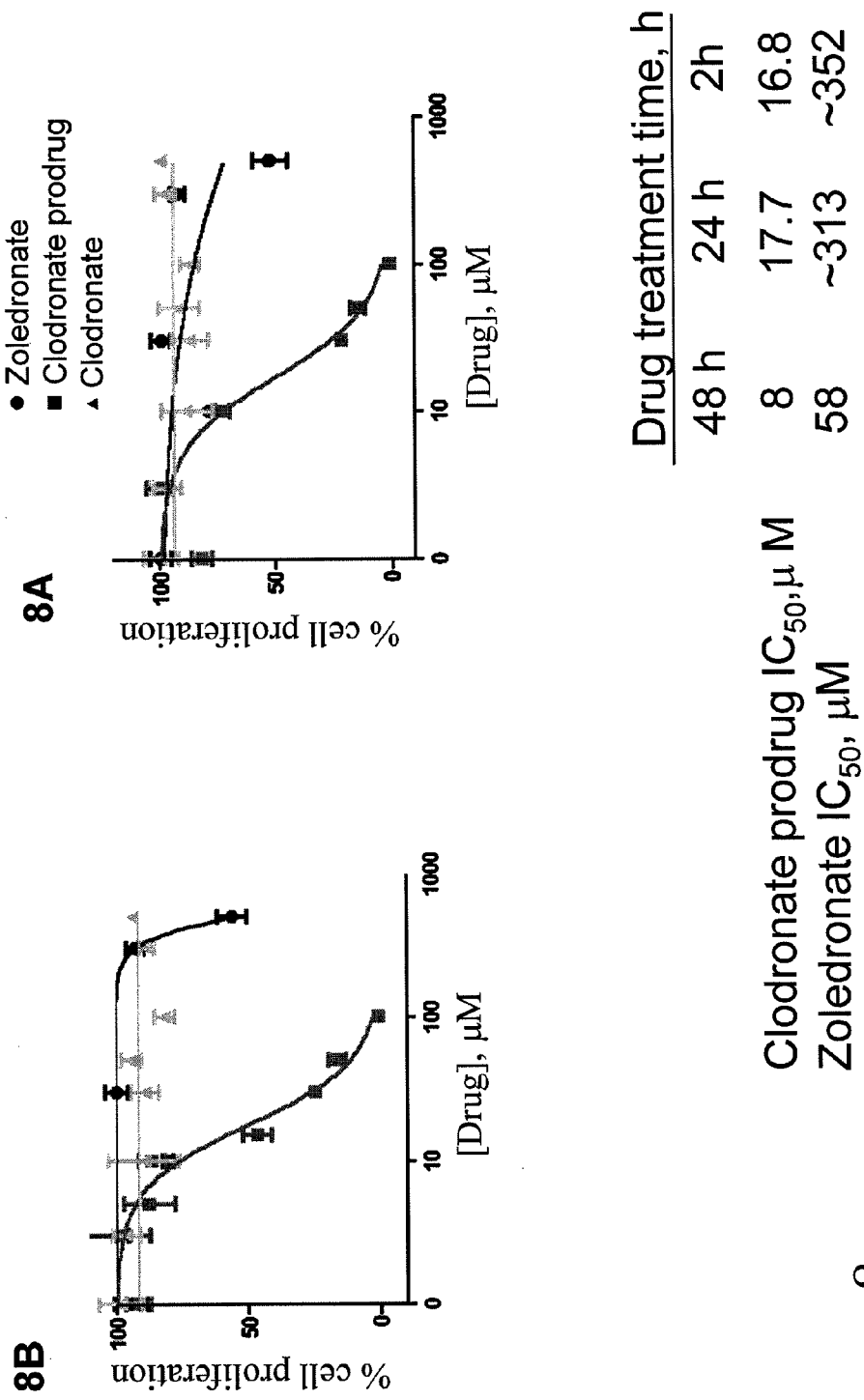
FIG. 8 shows the effect of increased time on the activity of clodronate prodrug (14) compared with zoledronate and clodronate.

A549 cells were treated with prodrug 14 for 24 or 2 h. Prodrug was removed and cell viability measured after 48 h using a standard MTS assay. Longer exposure to zoledronate results in lower 1050. Membrane permeable prodrug exhibits more potent growth inhibition than zoledronate over shorter drug treatment times. See FIG. 8.

Determination of Apoptotic Activity of Clodronate Prodrug

Figure 19:
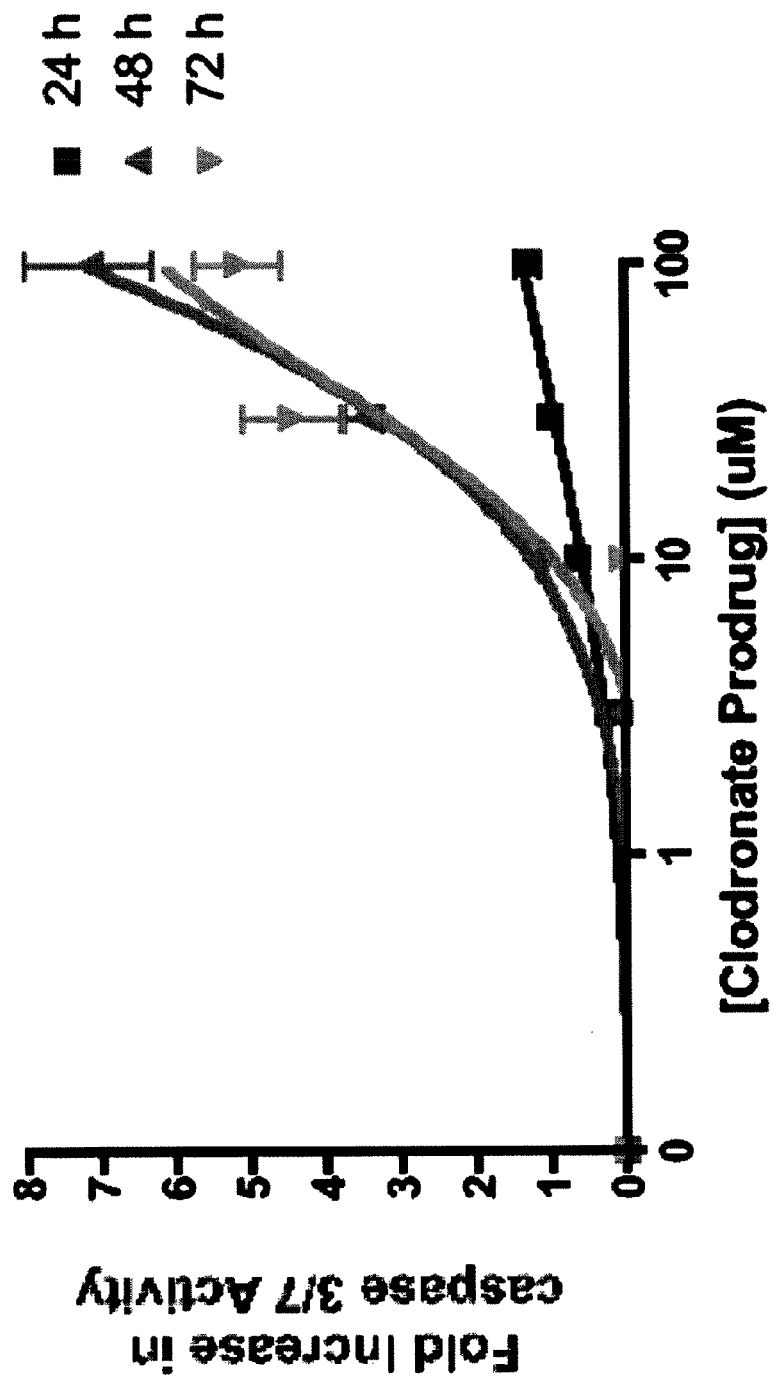
FIG. 19 shows the effect of clodronate prodrug (14) on activation of caspases 3/7.
Figure 20A:
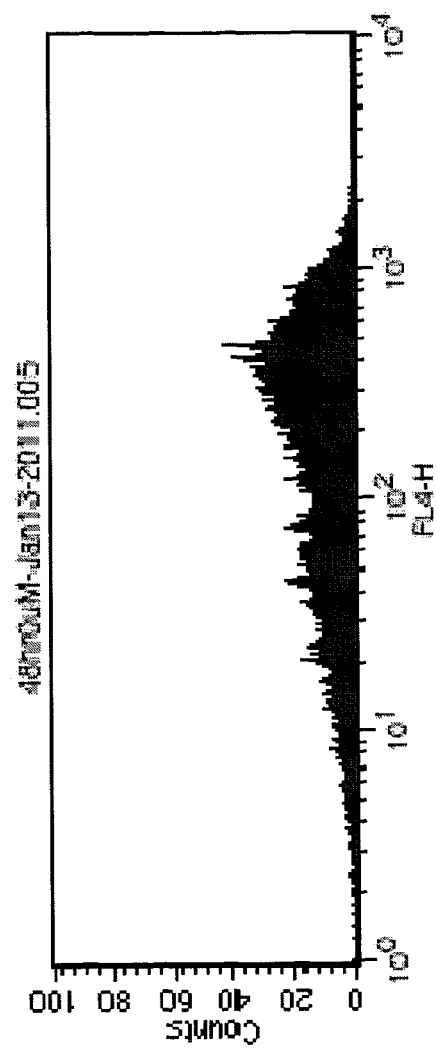
FIG. 20A shows a control with 48 hour treatment with 50 nM velcade (proteosome inhibitor).
Figure 20A:
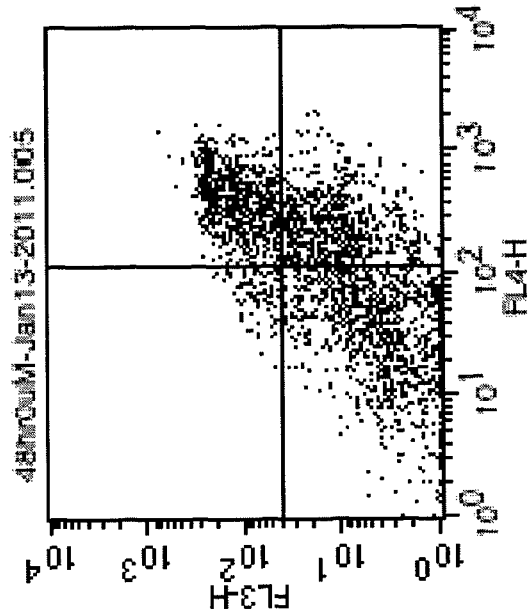
Figure 20B:
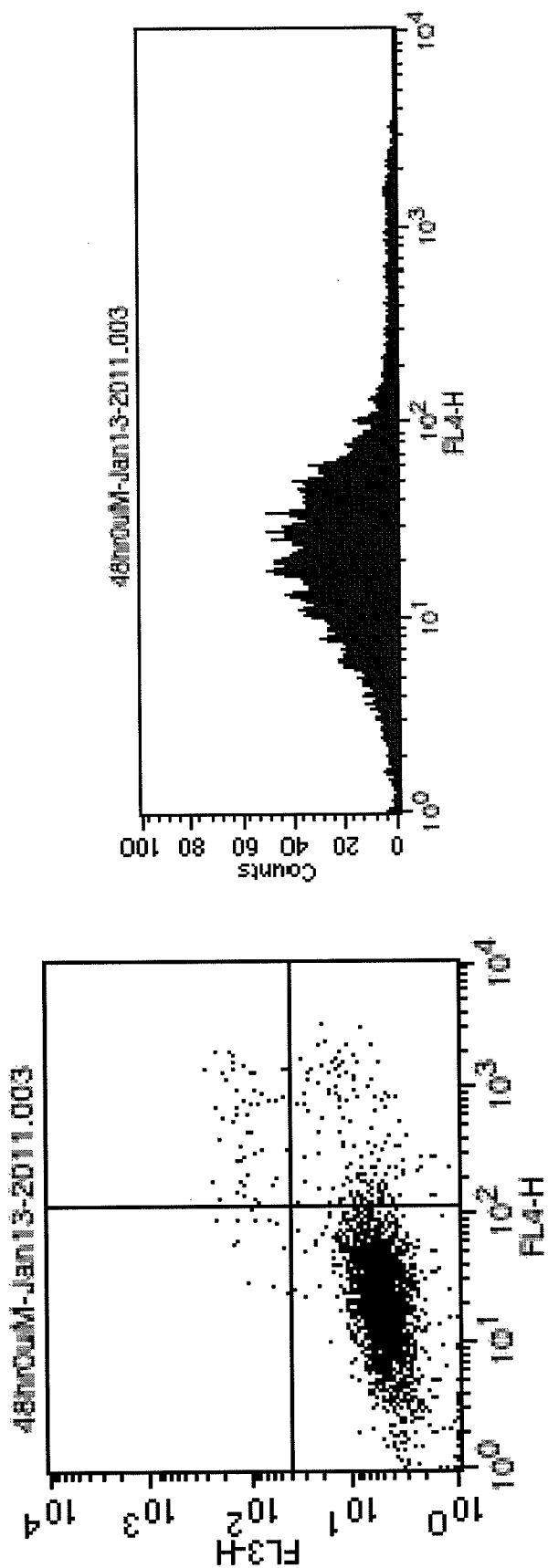
FIG. 20B shows 48 hour treatment with 10 μM clodronate prodrug (14).
Figure 20C:
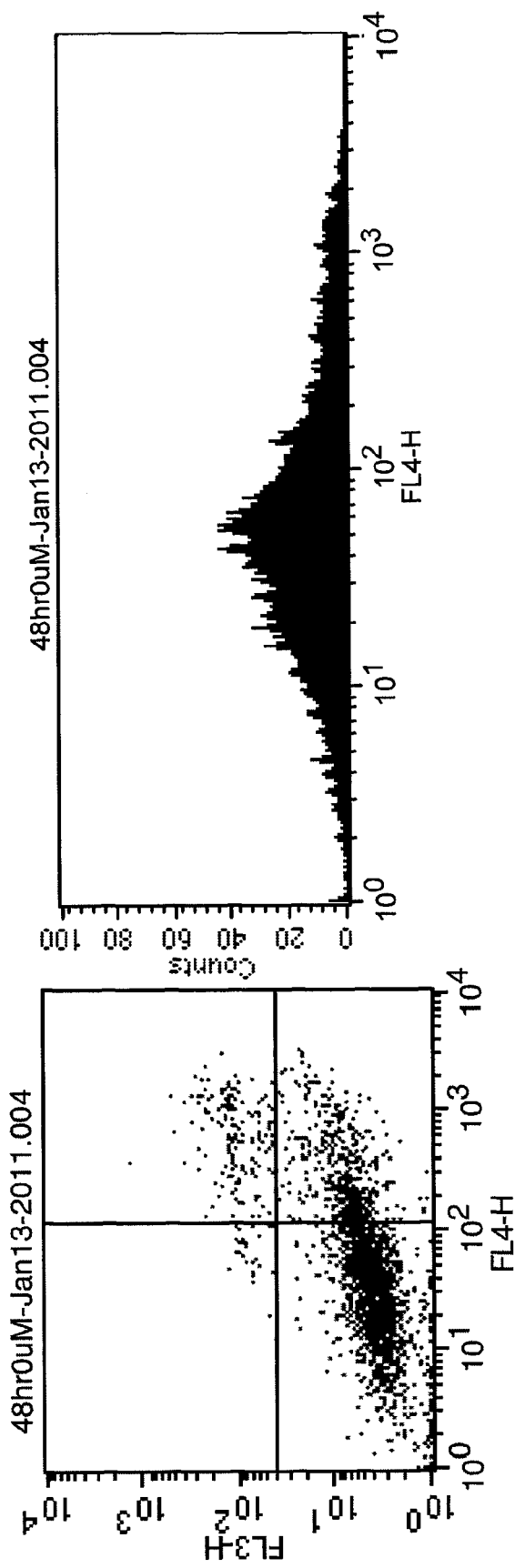
FIG. 20C shows 48 hour treatment with 100 μM clodronate prodrug (14).

Caspase Glo 3/7 (Promega) assay was used to determine caspases 3/7 activation following treatment of cells with clodronate prodrug. Briefly, cells were treated with clodronate prodrug for 24, 48, or 72 h. Caspase glo 3/7 (Promega) reagent (00 μL) was added to each well at 24, 48 or 72 h. The cells were then incubated at room temperature for 1 h, and the luminescence of each well was determined using a luminometer. Activation of caspases 3/7 suggest apoptosis pathways are initiated at higher drug concentrations by 48 hours as shown in FIG. 19.

Determination of Anti-Angiogenic Activity

This assay is an unpublished variation of the assay described (*Microvascular Research* 2003, 66, 102-112) performed by the Hans Hammers Lab at Johns Hopkins University. The assay described in the above reference is described below.

HUVEC were mixed with dextran-coated Cytodex 3 microcarriers (Amersham Pharmacia Biotech, Piscataway, N.J.) at a concentration of 400 HUVEC per bead in 1 ml of EGM-2 medium (Clonetics, Walkersville, Md.). Beads with cells were shaken gently every 20 min for 4 h at 37° C. and 5% $CO_2$. After incubating, beads with cells were transferred to a 25-cm$^2$ tissue culture flask (BD Biosciences, Bedford, Mass.) and left for 12-16 h in 5 ml of EGM-2 at 37° C. and 5% $CO_2$. The following day, beads with cells were washed three times with 1 ml of EGM-2 and resuspended at a concentration of 200 cell-coated beads/ml in 2.5 mg/ml of fibrinogen (Sigma, St. Louis, Mo.) with or without 0.15 units/ml of aprotinin (Sigma) at a pH of 7.4. Five hundred microliters of fibrinogen/bead solution was added to 0.625 units of thrombin (Sigma) in one well of a 24-well tissue culture plate. Fibrinogen/bead solution was allowed to clot for 5 min at room temperature and then at 37° C. and 5% $CO_2$ for 20 min One milliliter of EGM-2 (which contains 2% FBS) with or without 0.15 units/ml aprotinin was added to each well and equilibrated with the fibrin clot for 30 min at 37° C. and 5% $CO_2$. Medium was removed from the well and replaced with 1 ml of fresh medium with or without 0.15 units/ml aprotinin or additional growth factors. Twenty thousand SF were plated on top of the clot and medium was changed every other day. Bead assays were monitored for 7 days. $VEGF_{165}$, bFGF, Angiopoietin-1 (Ang-1), and transforming growth factor-β (TGF-β) (R&D Systems, Minneapolis, Minn.) were used at the indicated concentrations. In these experiments the VEGF that is normally part of the EGM-2 formulation was omitted.

Figure 21:
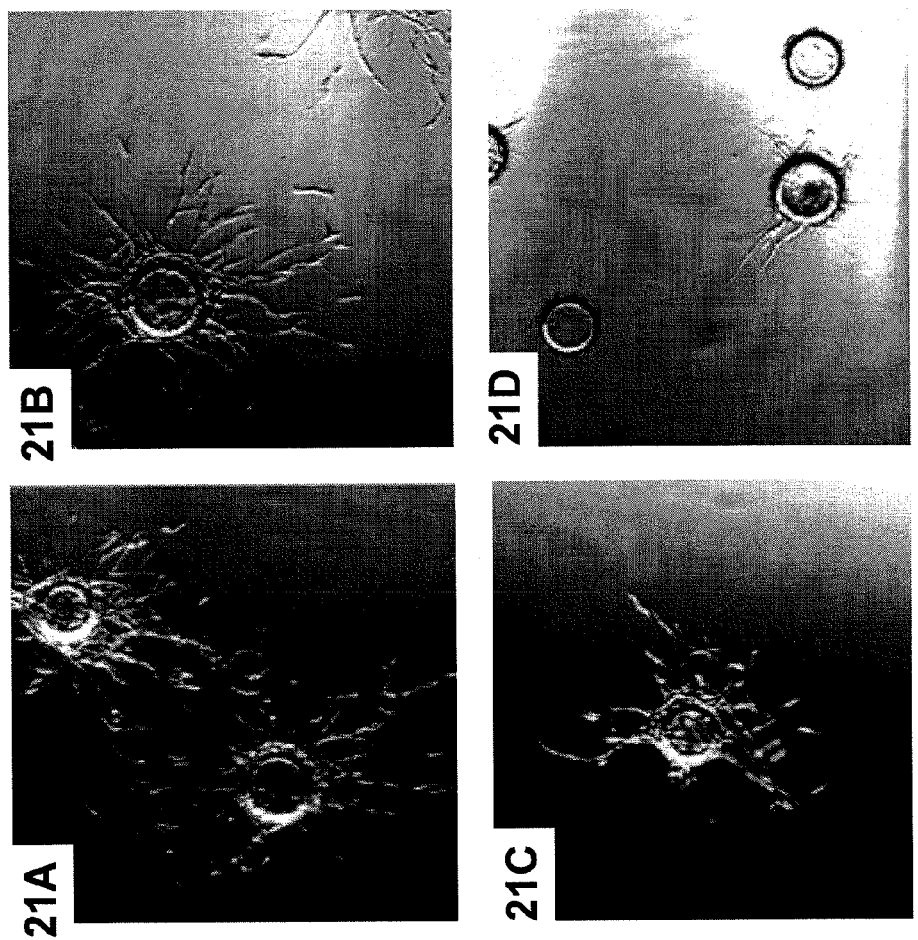
FIG. 21 shows a sprouting assay on dextran beads.

Sprouting assay on dextran beads shown in FIG. 21. FIG. 21A shows sprouting from positive control is supernatant from lung fibroblasts, FIG. 21B shows treatment with 2 μM clodronate prodrug, FIG. 21C shows treatment with 6 μM clodronate prodrug. FIG. 21D shows treatment with 10 μM clodronate prodrug. At 6 μM clodronate prodrug, sprouting was delayed for the first few days and "punched through" late in the assay. At 10 μM clodronate prodrug, sprouting is inhibited.

Effect of Prodrugs During Hypoxia

Figure 9:
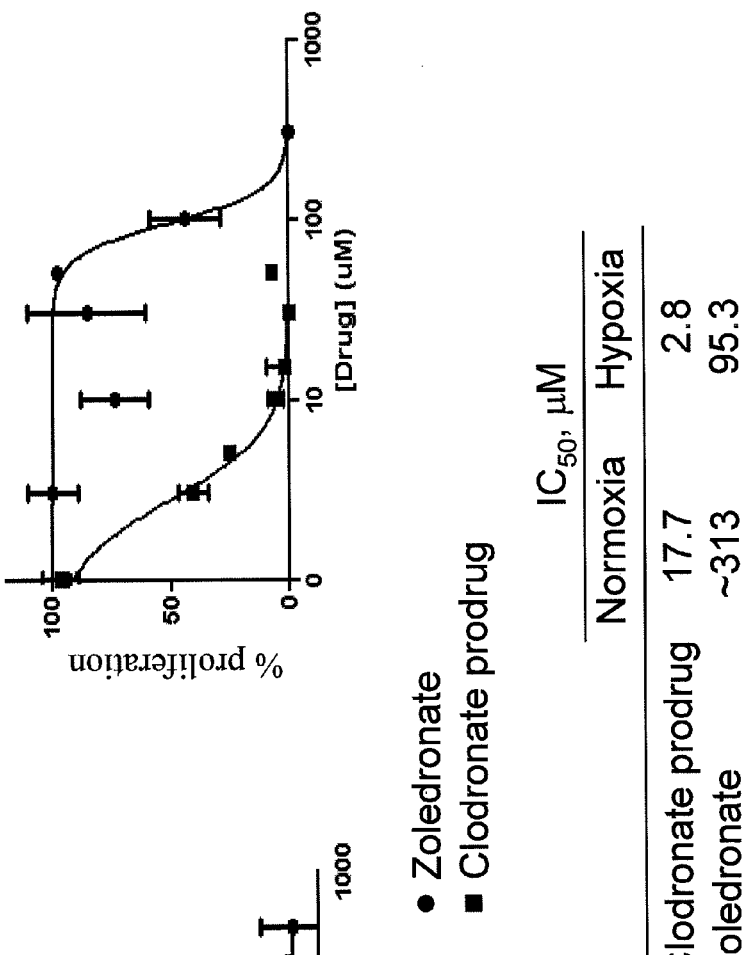
FIG. 9 shows the effect of 14 under hypoxic and normoxic conditions compared with Zoledronate.
Figure 9:
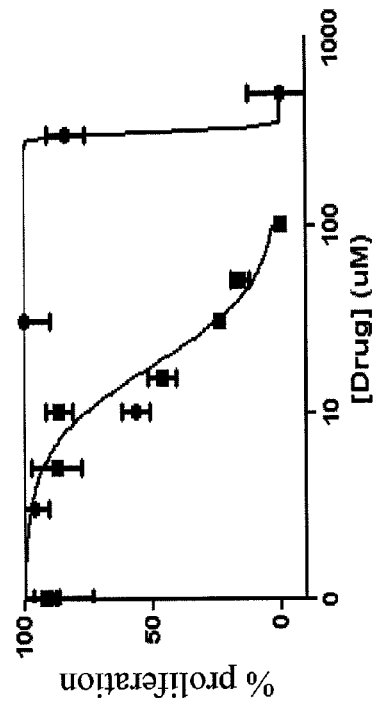

Nitro aromatic-containing prodrugs are often selectively toxic in solid tumors as a result of the more reducing environment within solid tumor cells. A549 cells were plated at $1.5 \times 10^3$ cells per well in 99 μL media in a flat bottom 96 well plate. Cells were either incubated at 20% oxygen, or 3% oxygen for 24 h. The drugs were serially diluted in 100% DMSO. For each drug treatment group, 1 μL of a 100× stock solution was added to each well for a final DMSO concentration of 1%. Cells were treated for 24 hours. Cells were incubated with MTS dye (20 μL well$^{-1}$) for 40 min to 2 h. Absorbance at 490 nm was determined using a SpectraMax M2 (Molecular Devices) plate reader as shown in FIG. 9.

Example 3

Activity of Chlodronate Prodrug on other Cancer Cells

Figure 22:
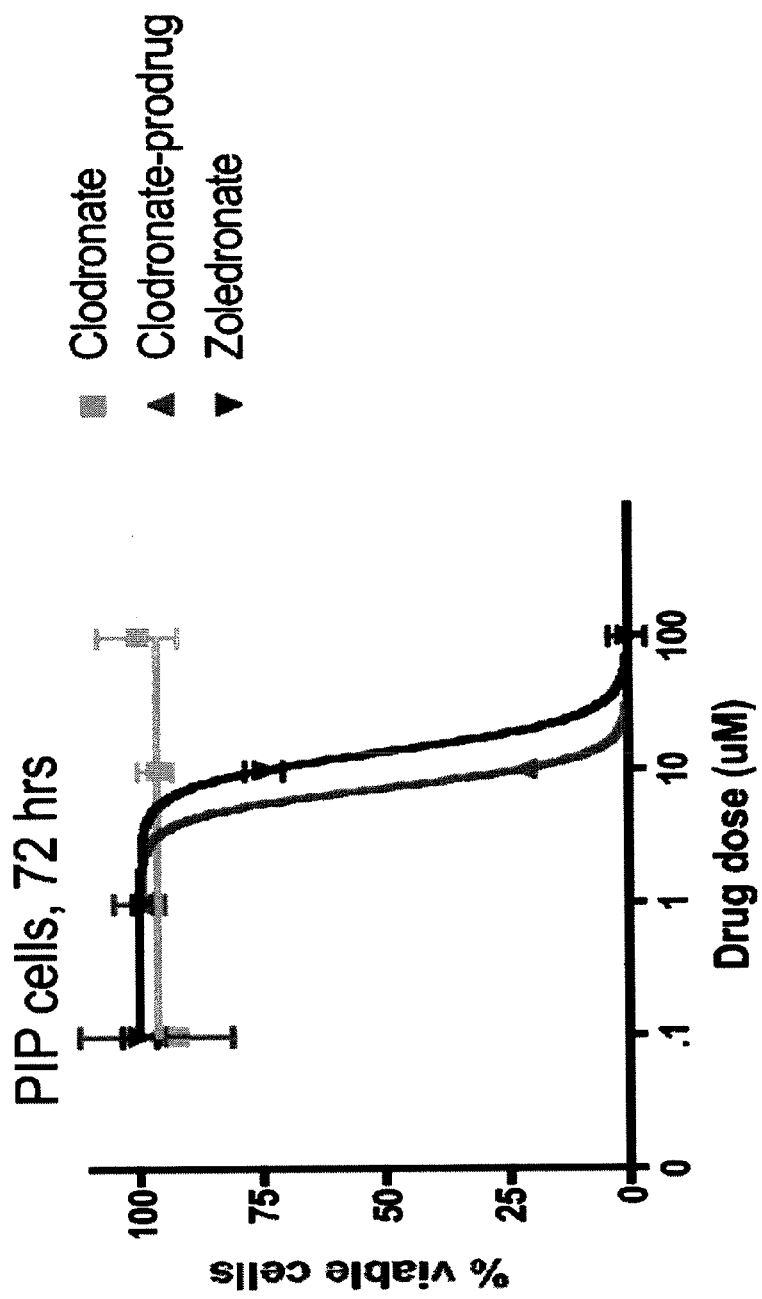
FIG. 22 shows activity of clodronate prodrug (14) against prostate (PIP3) cancer cell line.

The activity of Clodronate prodrug (14) was tested against other cell lines, include prostate (PIP3) and breast (MDA-MB-453) cancer cells lines. Cell proliferation was determined using the CellTiter 96 Aqueous One Solution Cell Proliferation Assay MTS assay as discussed above. Results are shown in FIG. 22 and in the table below.

| Cancer Cell Line | Clodronate Prodrug | Clodronate | Zoledronate |
| --- | --- | --- | --- |
| PIP3 (prostate) | EC50 = 3 μM | EC50 > 1 mM | EC50 = 78 μM |
| MDA-MB-453 (breast) | EC50 = 9 μM | EC50 > 1 mM | EC50 = 191 μM |
| A549 (NSCLC) | EC50 = 8 μM | EC50 > 1 mM | EC50 = 58 μM |

NCI-60 DTP Human Tumor Cell Line Screen

The human tumor cell lines of the cancer screening panel are grown in RPMI 1640 medium containing 5% fetal bovine serum and 2 mM L-glutamine. For a typical screening experiment, cells were inoculated into 96 well microtiter plates in 100 μL at plating densities ranging from 5,000 to 40,000 cells/well depending on the doubling time of individual cell lines. After cell inoculation, the microtiter plates were incubated at 37° C., 5% CO2, 95% air and 100% relative humidity for 24 h prior to addition of experimental drugs. After 24 h, two plates of each cell line were fixed in situ with TCA, to represent a measurement of the cell population for each cell line at the time of drug addition (Tz). Experimental drugs were solubilized in dimethyl sulfoxide at 400-fold the desired final maximum test concentration and stored frozen prior to use. At the time of drug addition, an aliquot of frozen concentrate was thawed and diluted to twice the desired final maximum test concentration with complete medium containing 50 μg/ml gentamicin. Additional four, 10-fold or ½ log serial dilutions were made to provide a total of five drug concentrations plus control. Aliquots of 100 μl of these different drug dilutions were added to the appropriate microtiter wells already containing 100 μl of medium, resulting in the required final drug concentrations.

Following drug addition, the plates were incubated for an additional 48 h at 37° C., 5% CO2, 95% air, and 100% relative humidity. For adherent cells, the assay was terminated by the addition of cold TCA. Cells were fixed in situ by the gentle addition of 50 μl of cold 50% (w/v) TCA (final concentration, 10% TCA) and incubated for 60 minutes at 4° C. The supernatant was discarded, and the plates washed five times with tap water and air dried. Sulforhodamine B (SRB) solution (100 μl) at 0.4% (w/v) in 1% acetic acid was added to each well, and plates incubated for 10 minutes at room temperature. After staining, unbound dye was removed by washing five times with 1% acetic acid and the plates were air dried. Bound stain was subsequently solubilized with 10 mM trizma base, and the absorbance read on an automated plate reader at a wavelength of 515 nm. For suspension cells, the methodology was the same except that the assay was terminated by fixing settled cells at the bottom of the wells by gently adding 50 μl of 80% TCA (final concentration, 16% TCA). Using the seven absorbance measurements [time zero, (Tz), control growth, (C), and test growth in the presence of drug at the five concentration levels (Ti)], the percentage growth was calculated at each of the drug concentrations levels. Percentage growth inhibition were calculated as:

[(Ti−Tz)/(C−Tz)]×100 for concentrations for which Ti>/=Tz [(Ti−Tz)/Tz]×100 for concentrations for which Ti<Tz.

Three dose response parameters were calculated for each experimental agent. Growth inhibition of 50% (GI50) was calculated from [(Ti−Tz)/(C−Tz)]×100=50, which was the drug concentration resulting in a 50% reduction in the net protein increase (as measured by SRB staining) in control cells during the drug incubation. The drug concentration resulting in total growth inhibition (TGI) was calculated from Ti=Tz. The LC50 (concentration of drug resulting in a 50% reduction in the measured protein at the end of the drug treatment as compared to that at the beginning) indicating a net loss of cells following treatment was calculated from [(Ti−Tz)/Tz]×100=−50. Values were calculated for each of these three parameters if the level of activity is reached; however, if the effect was not reached or was exceeded, the value for that parameter is expressed as greater or less than the maximum or minimum concentration tested.

| Panel/Cell Line | $Log_{10}GI50$ | $Log_{10}TGI$ | $Log_{10}LC50$ |
| --- | --- | --- | --- |
| Leukemia | | | |
| CCRF-CEM | −5.50 | >−4.00 | >−4.00 |
| HL-60(TB) | −5.39 | >−4.00 | >−4.00 |
| K-562 | −5.45 | >−4.00 | >−4.00 |
| MOLT-4 | −5.53 | −5.04 | >−4.00 |
| RPMI-8226 | −5.57 | >−4.00 | >−4.00 |

-continued

| Panel/Cell Line | Log₁₀GI50 | Log₁₀TGI | Log₁₀LC50 |
|---|---|---|---|
| SR | −5.43 | >−4.00 | >−4.00 |
| Non-Small Cell Lung Cancer | | | |
| A549/ATCC | −5.37 | >−4.00 | >−4.00 |
| EKVX | −5.50 | >−4.00 | >−4.00 |
| HOP-62 | >−4.00 | >−4.00 | >−4.00 |
| NCI-H226 | −5.52 | >−4.00 | >−4.00 |
| NCI-H23 | −5.58 | >−4.00 | >−4.00 |
| NCI-H322M | −5.34 | >−4.00 | >−4.00 |
| NCI-H460 | −5.42 | >−4.00 | >−4.00 |
| NCI-H522 | −5.66 | −5.11 | >−4.00 |
| Colon Cancer | | | |
| COLO 205 | −5.53 | −5.10 | >−4.00 |
| HCC-2998 | −5.25 | >−4.00 | −4.46 |
| HCT-116 | −5.58 | >−4.00 | >−4.00 |
| HCT-15 | −5.41 | >−4.00 | >−4.00 |
| HT29 | −5.48 | −4.65 | >−4.00 |
| KM12 | −5.46 | >−4.00 | >−4.00 |
| SW-620 | −5.27 | >−4.00 | >−4.00 |
| CNS Cancer | | | |
| SF-268 | −5.55 | >−4.00 | >−4.00 |
| SF-295 | −5.61 | −4.77 | >−4.00 |
| SF-539 | −5.44 | >−4.00 | >−4.00 |
| SNB-19 | −5.30 | >−4.00 | >−4.00 |
| SNB-75 | −5.65 | −5.17 | >−4.00 |
| U251 | −5.45 | >−4.00 | >−4.00 |
| Melanoma | | | |
| LOX IMVI | −5.75 | −5.33 | −4.26 |
| MALME-3M | −5.39 | >−4.00 | >−4.00 |
| M14 | −5.40 | >−4.00 | >−4.00 |
| MDA-MB-435 | −5.55 | −4.65 | >−4.00 |
| SK-MEL-2 | −5.60 | −5.18 | >−4.00 |
| SK-MEL-28 | −5.42 | >−4.00 | >−4.00 |
| SK-MEL-5 | −5.69 | −5.37 | −5.05 |
| UACC-257 | −5.56 | −5.10 | >−4.00 |
| UACC-62 | −5.70 | −5.30 | −4.11 |
| Ovarian Cancer | | | |
| IGROV1 | −5.39 | >−4.00 | >−4.00 |
| OVCAR-3 | −5.40 | >−4.00 | >−4.00 |
| OVCAR-4 | −5.54 | >−4.00 | >−4.00 |
| OPVCAR-5 | −5.45 | >−4.00 | >−4.00 |
| OVCAR-8 | −5.38 | >−4.00 | >−4.00 |
| NCI/ADR-RES | −5.58 | >−4.00 | >−4.00 |
| SK-OV-3 | −5.19 | >−4.00 | >−4.00 |
| Renal Cancer | | | |
| 786-0 | −5.28 | >−4.00 | >−4.00 |
| A498 | −5.74 | −5.17 | >−4.00 |
| ACHN | −5.49 | >−4.00 | >−4.00 |
| CAKI-1 | −5.54 | >−4.00 | >−4.00 |
| RXF 393 | −5.50 | −4.38 | >−4.00 |
| SN12C | −5.42 | >−4.00 | >−4.00 |
| TK-10 | −5.35 | >−4.00 | >−4.00 |
| UO-31 | −5.76 | >−4.00 | >−4.00 |
| Prostate Cancer | | | |
| PC-3 | −5.44 | >−4.00 | >−4.00 |
| DU145 | −5.40 | >−4.00 | >−4.00 |
| Breast Cancer | | | |
| MCF7 | −5.47 | −4.82 | >−4.00 |
| MDA-MB-231/ATCC | −5.51 | >−4.00 | >−4.00 |
| HS 578T | −5.53 | −5.04 | >−4.00 |
| BT-549 | −5.50 | −5.03 | >−4.00 |
| T-47D | −5.27 | >−4.00 | >−4.00 |
| MDA-MB-468 | −5.58 | −5.07 | >−4.00 |

The NCI renamed the IC50 value, the concentration that causes 50% growth inhibition, the GI50 value to emphasize the correction for the cell count at time zero; thus, GI50 is the concentration of test drug where 100×(T−T0)/(C−T0)=50 (Boyd et al., In Cytotoxic Anticancer Drugs: Models and Concepts for Drug Discovery and Development; Vleriote et al., Eds., Kluwer Academic: Hingham, Mass., pp 11-34, 1992; Monks et al., JNCI, J. Natl. Cancer Inst., vol. 83, pp. 757-766, 1991). The optical density of the test well after a 48-h period of exposure to test drug is T, the optical density at time zero is T0, and the control optical density is C. The "50" is called the GI50PRCNT, a T/C-like parameter that can have values from +100 to −100. The GI50 measures the growth inhibitory power of the test agent. The TGI is the concentration of test drug where 100×(T−T0)/(C−T0)=0. Thus, the TGI signifies a cytostatic effect. The LC50, which signifies a cytotoxic effect, is the concentration of drug where 100×(T−T0)/T0=−50. The control optical density is not used in the calculation of LC50.

Example 4

Antiparasitic Activity

Determination of Antimalarial Activity with Cytotoxicity assays.

Plasmodium falciparum culture. NF54 P. falciparum parasites were maintained in O+ positive erythrocytes (obtained weekly from a rotating pool of screened healthy donors) in complete medium containing RPMI (Sigma), 25 mM N-2-hydroxyethylpiperazine-N'-2-ethanesulfonic acid (HEPES; Sigma), 27 mM sodium bicarbonate (Sigma) and 10% heat-inactivated male O+ serum in non-vented flasks. Hematocrit was maintained at 2.4%. Flasks were gassed with a mixture of 3% oxygen, 4% carbon dioxide, 93% nitrogen. Parasitemia was maintained at 0.1-5% by changing medium and erythrocytes two to three times a week.

Figure 10:
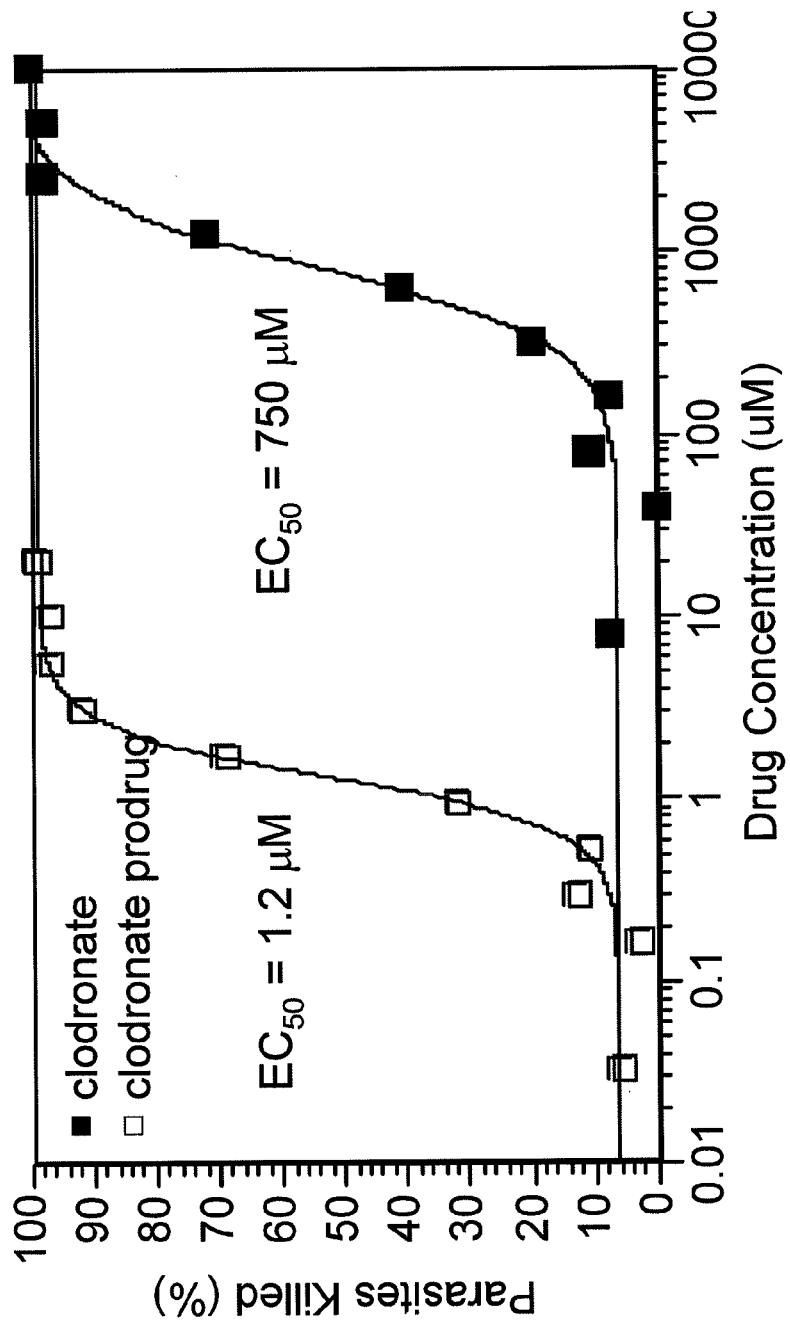
FIG. 10 shows the effect of clodronate prodrug (14) on parasite *P. falciparum* compared to clodronate.
Figure 11:
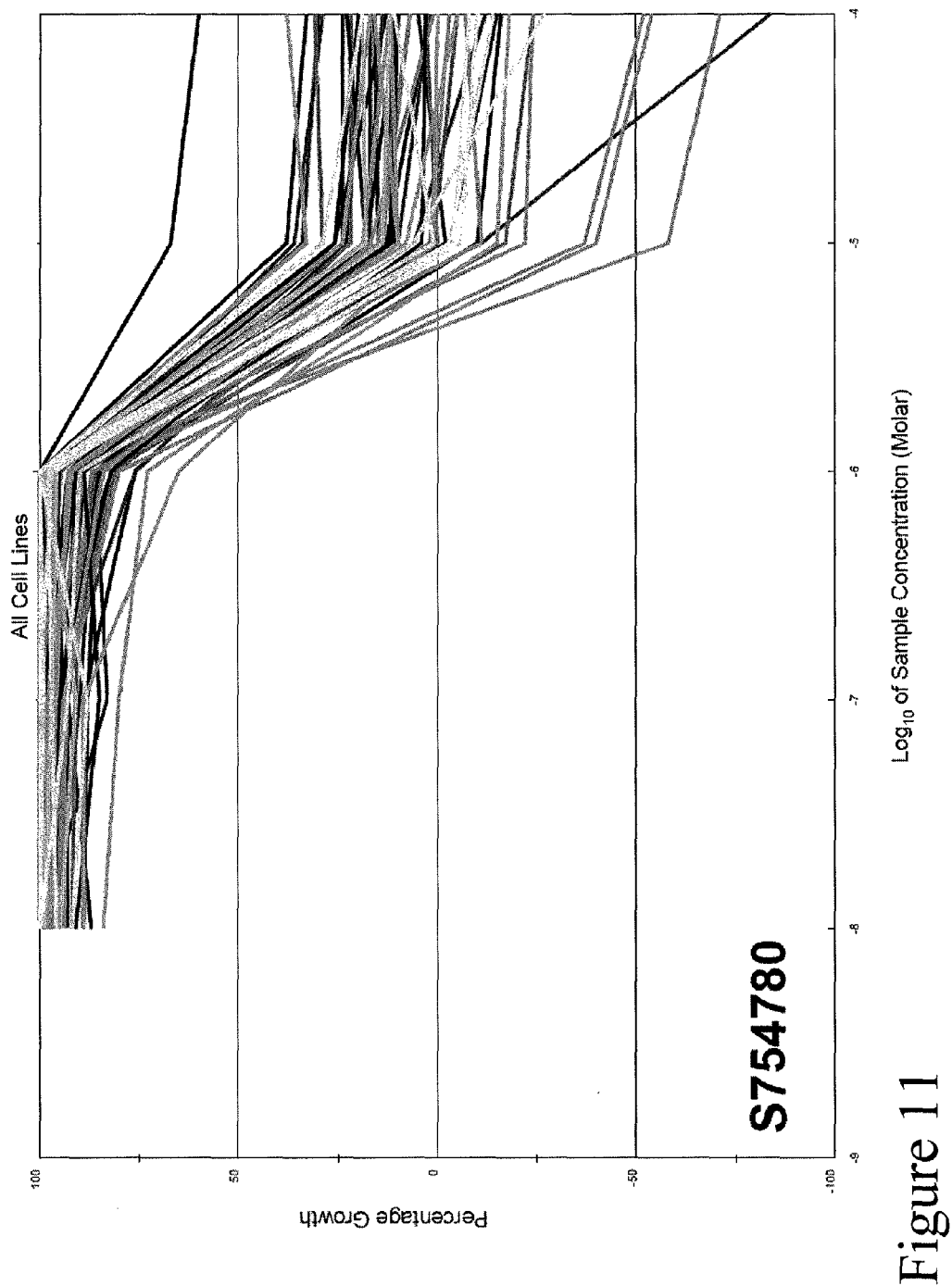
FIG. 11 shows the effect of clodronate prodrug (14) on cell viability of all 60 cancer cells lines in the NCI-60 human cancer cell library.
Figure 12:
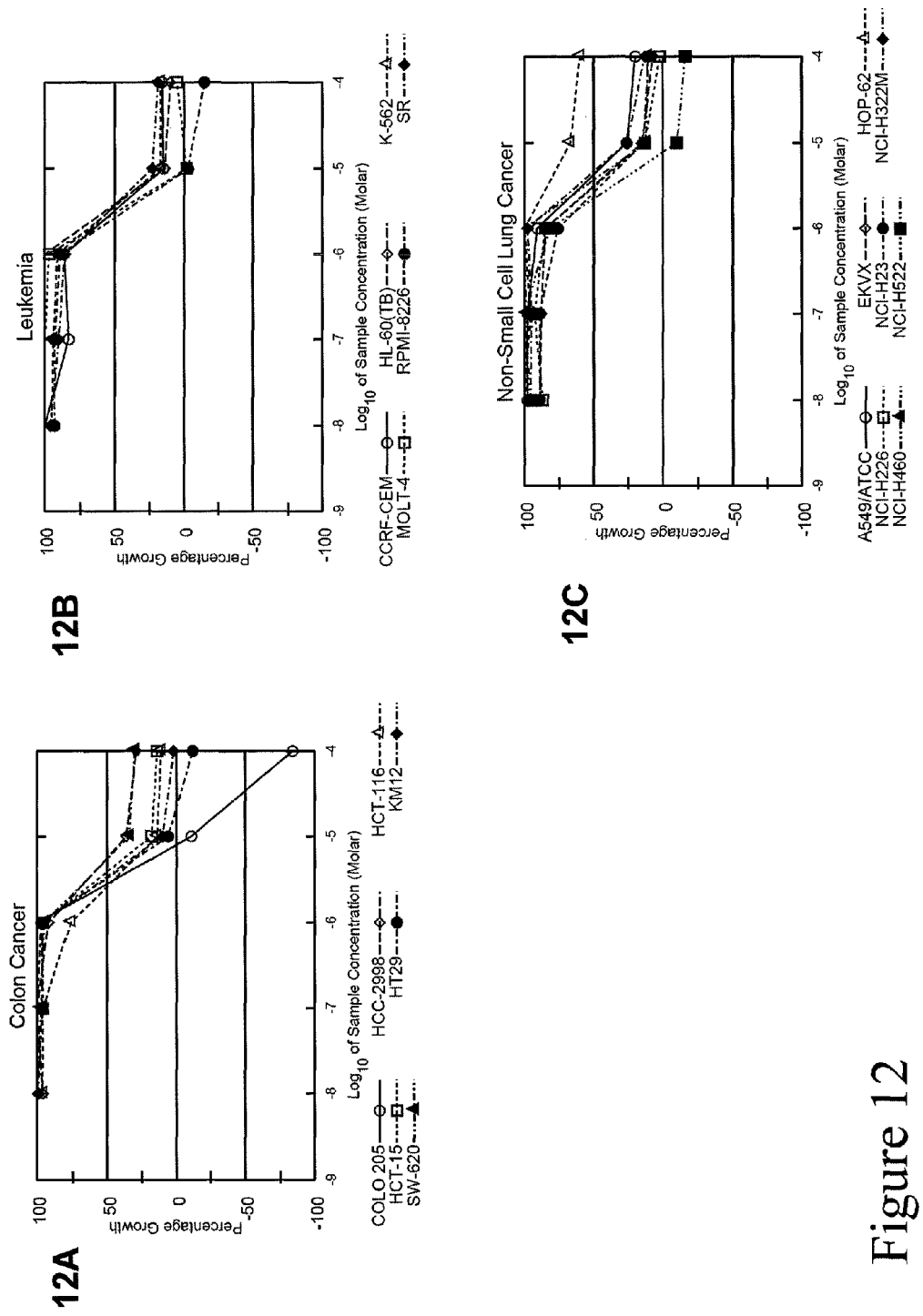
FIG. 12 shows the effect of 14 on cell viability for different cancer types within the NCI-60 human cancer cell library; Colon Cancer (FIG. 12A), Leukemia (FIG. 12B), Non-Small Cell Lung Cancer (FIG. 12C), CNS Cancer (FIG. 12D), Melanoma (FIG. 12E), Ovarian Cancer (FIG. 12F), Renal Cancer (FIG. 12G), Prostate Cancer (FIG. 12H), Breast Cancer (FIG. 12I).

Antimalarial activity was measured using a [$^3$H]-hypoxanthine incorporation assay as described previously (Desjardins et al., Antimicrob. Agents Chemother., vol. 16, p. 710, 1979; Milhous et al., Antimicrob. Agents Chemother., vol. 27, np. 525, 1985). Briefly, 100 µL of complete medium containing P. falciparum culture at 0.25% parasitemia was incubated with 100 µL of medium containing solvent or 2× serially diluted compound (44 to 48 h, 37° C.). For surveys, each concentration was assayed in triplicate while in expansions, each concentration was assayed in quadruplicate. To each well, 0.64 µCi of [$^3$H]-hypoxanthine (10-30 Ci/mmol; Perkin Elmer) was added and the plate was incubated for an additional 20 to 24 h. Samples from each well were harvested on filter paper and tritium counts were measured on the Beckmann Coulter LS6500 scintillation counter. Curve fitting and 50% effective concentration ($EC_{50}$) were obtained with the $E_{max}$ model and DeltaGraph Pro 3.5. Values considered as outliers according to Chauvenet's criterion were discarded and dropped from analysis. One survey and at least one expansion was performed for each compound. Results are shown in FIG. 10.

Determination of Antitrypanosomal Activity with Cytotoxicity assays.

All experiments were performed with bloodstream form Trypanosoma brucei brucei (MiTat 1.2 strain 427; doubling time 6-8 h), grown at 37° C. in HMI-9 containing 10% fetal bovine serum, 10% Serum Plus and 0.8 µg/mL G418 (Gibco BRL Life Technologies, Inc.).

Cytotoxicity Assay.

Assays were performed according to methods described by Posner et al. (Tetrahedron, vol. 53, no. 1, pp. 37-50, 1997). Briefly, compounds were assayed for anti-trypanosomal activity using an acid phosphatase-based 96-well plate method (Bodley, 1995). Briefly, 100 µL of cells (2×10⁵/mL) were incubated with 100 µL of medium containing solvent or 2× serially diluted compound (20-24 h, 37° C.). Each concentration was assayed in quadruplicate. Final DMSO concentrations did not exceed 1%. Lethality was confirmed by microscopic examination for motility. Acid phosphatase activity from surviving cells was measured by adding 20 μL of buffer containing 20 mg/mL p-nitrophenyl phosphate in 1M sodium acetate pH 5.5, 1% Triton X-100 (5 h, 37° C.). Absorbance was measured at 405 nm. Each compound was assayed at least times. Curve fitting and $EC_{50}$ determinations were obtained with the $E_{max}$ model and DeltaGraph Pro 3.5. Based on Chauvenet's criterion, values were identified as outliers and were dropped from analysis.

Results

Antiparasitic results are shown, for example, in FIG. 10 and the table below.

|  | P. falciparum (NF54) | T. brucei brucei | L1210 |
|---|---|---|---|
| Clodronate Prodrug, $IC_{50}$ (μM) | 0.98 ± 0.21 | 4.05 ± 0.64 | 11.65 ± 1.78 |
| Clodronate, $IC_{50}$ (μM) | 750 | — | 830 |
| Bisphosphonate Prodrug, $IC_{50}$ (μM) | 5.2 ± 0.21 | 6.1 | 27 |
| Diethylamine Analog, $IC_{50}$ (μM) | 3.3 | 9.1 | — |
| Chlorobenzyl analog, $IC_{50}$ (μM) | 5.9 | 8.6 | — |
| Nitrophenethyl analog, $IC_{50}$ (μM) | 0.97 ± 0.21 | 4 | — |
| Methoxy analog, $IC_{50}$ (μM) | 22 | — | — |

Example 5

Synthesis and Activity of Other Esters

Compounds were designed to evaluate the importance of nitroaryl group to bisphosphonate prodrug activity. Activity was not expected in analogs lacking a nitro group or those designed to be incapable of undergoing elimination. Surprisingly, activity was found for all analogs, suggesting there may be alternative activation pathways for this prodrug class.

Deschloromethoxy Analog (not tested):

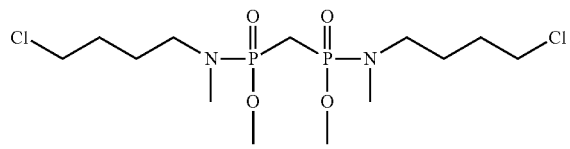 [SMILES: COP(=O)(CP(=O)(OC)N(C)CCCCCl)N(C)CCCCCl]

Methylenebis(phosphonic dichloride) (0.181 g, 0.725 mmol) and N-methyl-N-(4-chlorobutyl)amine hydrochloride (0.229 g, 1.45 mmol) were dissolved in $CH_2Cl_2$ (2.9 mL) and cooled to 0° C. with stiffing under an Ar atmosphere. DIPEA (0.606 ml, 3.48 mmol) was added dropwise. The reaction mixture was allowed to warm to room temperature, and stirring was continued for 2 h. In a separate flask under an Ar atmosphere combine, DMAP (0.089 mg, 0.725 mmol), methanol (0.118 mL, 2.9 mmol), DIPEA (0.303 mL, 1.74 mmol) in $CH_2Cl_2$ (0.1 ml) wre combined and added to the reaction mixture dropwise. The reaction was stirred at room temperature for 2 h. The crude reaction mixture was pushed forward into the chlorination reaction. $^{31}P$ NMR($C_6D_6$) δ 1.1 (2 s, 1).

Methoxy Analog:

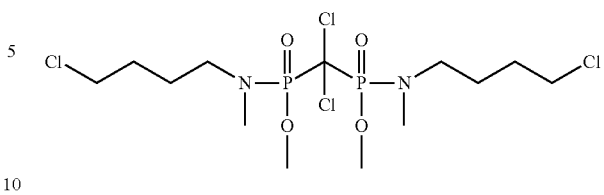

The deschloromethoxy analog (0.297 g, 0.725 mmol) was dissolved in $CCl_4$ (2.32 ml) and MeOH (0.422 ml). Benzyltriethylammonium chloride (0.073 g, 0.319 mmol) was added in one portion. 10% NaOCl solution (4.46 mL) was added with stiffing and the reaction stirred over night. The reaction was quenched with saturated $NH_4Cl$ solution (1 mL), and the organic layer was concentrated under reduced pressure. The chlorinated product was purified by pipette column chromatography (100% ethyl acetate) to afford the above compound as a pale yellow oil. $^{31}P$ NMR (CDCl$_3$) δ −8.2 (s); $^1H$ NMR (CDCl$_3$) δ 3.88 (d, 4H); 3.52 (t, 6H); 5.4 (m, 2H); 5.2 (m, 2H); 2.8 (t, 6H); 1.75 (br m, 8H).

Deschlorobenzyl Analog:

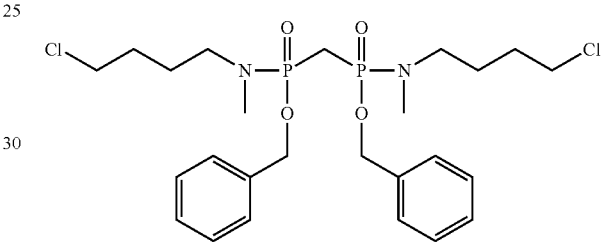

Methylenebis(phosphonic dichloride) (0.0704 g, 0.282 mmol) and N-methyl-N-(4-chlorobutyl)amine hydrochloride (0.089 g, 0.564 mmol) were dissolved in $CH_2Cl_2$ (1.1 mL) and cooled to 0° C. with stiffing under an Ar atmosphere. DIPEA (0.235 ml, 1.35 mmol) was added dropwise. The reaction mixture was allowed to warm to room temperature, and stiffing was continued for 2 h. In a separate flask under an Ar atmosphere combine, DMAP (0.034 mg, 0.28 mmol), benzyl alcohol (0.117 mL, 1.1 mmol), DIPEA (0.118 mL, 0.68 mmol) in $CH_2Cl_2$ (0.5 ml) were combined and added to the reaction mixture dropwise. The reaction was stirred at room temperature for 2 h. The reaction mixture was washed with saturated $NH_4Cl$, the organic layer was dried over sodium sulfate and concentrated under reduced pressure. Purification was accomplished by column chromatography (1:19, methanol/ethyl acetate) to afford the above compound as a pale yellow oil 17% yield. $^{31}P$ NMR (CD$_3$OD) δ 2.4 (2 s, 1); $^1H$ NMR (CD$_3$OD) δ 7.30 (m, 10H); 4.8 (m, 4H); 3.3 (q, 4H); 3.0 (m, 2H); 2.8 (m, 2H); 2.5 (d, 6H); 1.6 (m, 8H).

Chlorobenzyl Analog:

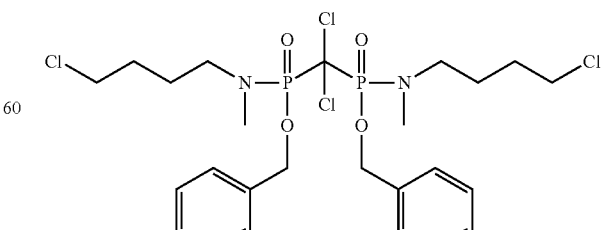

The deschlorobenzyl analog (0.027 g, 0.047 mmol) was dissolved in CCl$_4$ (0.103 ml) and MeOH (0.05 ml). Benzyltriethylammonium chloride (0.005 g, 0.021 mmol) was added in one portion. 10% NaOCl solution (0.16 mL) was added with stirring. The reaction was monitored by $^{31}$P NMR over a period of 4 hours until completion. The reaction was quenched with saturated NH$_4$Cl solution (2 mL), and the product was extracted using CH$_2$Cl$_2$ (2×0.5 ml). The chlorinated product was purified by column chromatography (100% ethyl acetate to afford the above compound as a pale yellow oil. $^{31}$P NMR (CDCl$_3$) δ-10.2 (2 s); $^1$H NMR (CDCl$_3$) δ 7.2 (m, 10H); 5.2 (d, 4H); 3.4 (m, 4H); 3.3 (m, 2H); 3.0 (m, 2H); 2.75 (m, 4H); 1.6 (br m, 8H).

Deschloro Nitrophenethyl Analog (not tested):

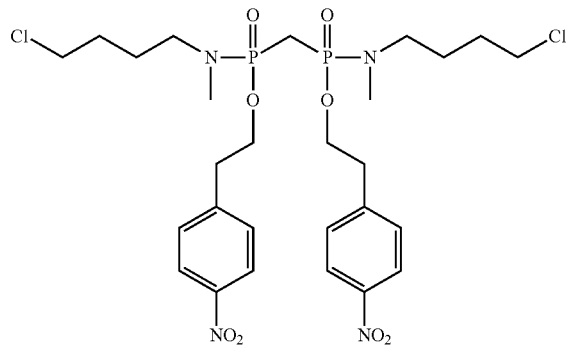 [SMILES: CN(CCCCCl)P(=O)(CP(=O)(OCCc1ccc([N+](=O)[O-])cc1)N(C)CCCCCl)OCCc1ccc([N+](=O)[O-])cc1]

Methylenebis(phosphonic dichloride) (0.177 g, 0.709 mmol) and N-methyl-N-(4-chlorobutyl)amine hydrochloride (0.224 g, 1.42 mmol) were dissolved in CH$_2$Cl$_2$ (2.8 ml) and cooled to 0° C. with stirring under an Ar atmosphere. DIPEA (0.593 ml, 3.4 mmol) was added dropwise. The reaction mixture was allowed to warm to room temperature, and stirring was continued for 2 h. In a separate flask under an Ar atmosphere, DMAP (0.087 mg, 0.71 mmol) and 4-Nitrophenethyl alcohol (0.355 g, 2.12 mmol) were dissolved in CH$_2$Cl$_2$ (1.5 ml) and DIPEA (0.296 ml, 0.1.7 mmol) added. The reaction mixture was stirred at room temperature for 2 h.

Nitrophenethyl Analog:

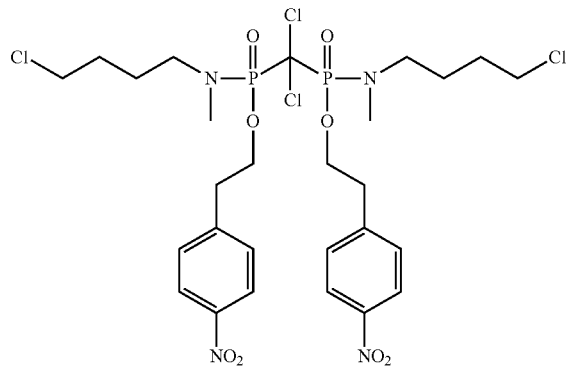 [SMILES: CN(CCCCCl)P(=O)(OCCc1ccc([N+](=O)[O-])cc1)C(Cl)(Cl)P(=O)(OCCc1ccc([N+](=O)[O-])cc1)N(C)CCCCCl]

The deschloronitrophenethyl analog (0.457 g, 0.67 mmol) was dissolved in CCl$_4$ (1.5 mL) and MeOH (0.75 mL). Benzyltriethylammonium chloride (0.067 g, 0.241 mmol) was added in one portion. 10% NaOCl solution (2.26 mL) was added with stirring. The reaction was monitored by $^{31}$P NMR over a period of 4 hours until completion. The reaction was quenched with saturated NH$_4$Cl solution (2 mL), and the product was extracted using CH$_2$Cl$_2$ (3×0.5 mL). The chlorinated product was purified by column chromatography (1:20 methanol/ethyl acetate) to afford the above compound as a pale yellow oil. $^{31}$P NMR (CDCl$_3$) δ −11.0 (2 s); $^1$H NMR (CDCl$_3$) δ 8.19 (d, 4H); 7.42 (d, 4H); 4.58 (m, 2H); 4.3 (m, 2H); 3.5 (m, 4H); 3.38 (m, 4H); 3.2 (br m, 4H); 3.05 (br m, 4H); 2.7 (m, 6H); 1.2 (m, 4H); 0.8 (m, 4H). ESI-MS m/z 749, 751, 753 (M+1).

Deschlorodiethylamine Analog:

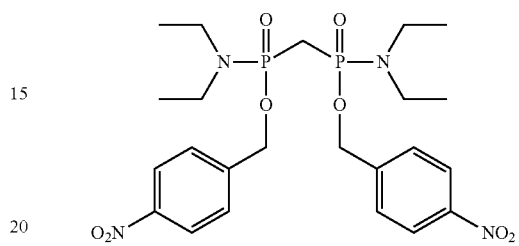

Methylenebis(phosphonic dichloride) (0.0896 g, 0.359 mmol) and diethyl amine (0.052 g, 0.717 mmol) were dissolved in CH$_2$Cl$_2$ (1.43 ml) and cooled to 0° C. with stirring under an Ar atmosphere. DIPEA (0.150 ml, 0.862 mmol) was added dropwise. The reaction mixture was allowed to warm to room temperature, and stirring was continued for 2 h. In a separate flask under an Ar atmosphere, DMAP (0.228 mg, 1.87 mmol) and nitrobenzyl alcohol (0.275 g, 1.795 mmol) were dissolved in CH$_2$Cl$_2$ (0.2 ml) and DIPEA (0.150 ml, 0.862 mmol) added. The reaction was stirred at room temperature for 2 h. Purification was accomplished by column chromatography (1:9, hexanes/ethyl acetate) to afford the above compound. $^{31}$P NMR (CDCl$_3$) δ 0.13 (s, 1); −0.15 (s, 1.5); $^1$H NMR (CDCl$_3$) δ 8.1 (2d, 4H); 7.5 (2d, 4H); 5.18 (m, 2H); 4.90 (m, 2H); 3.10 (br m, 8H); 1.05 (m, 12H).

Diethylamine Analog (tested in parasites only):

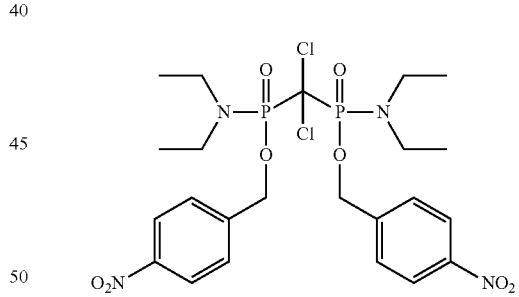

The deschlorodiethylamine analog (0.008 g, 0.014 mmol) was dissolved in CCl$_4$ (0.035 ml) and MeOH (0.02 ml). Benzyltriethylammonium chloride (0.001 g, 0.006 mmol) was added in one portion. 10% NaOCl solution (0.042 mL) was added with stirring. The reaction mixture was stirred overnight. The reaction was quenched with saturated NH$_4$Cl solution (0.1 mL), and the product extracted using CH$_2$Cl$_2$ (2×0.5 ml). The chlorinated product was purified by pipette column chromatography (100% ethyl acetate) to afford the above compound as a pale yellow oil. $^{31}$P NMR (CDCl$_3$) δ −3.7 (2 s); $^1$H NMR (CDCl$_3$) δ 8.2 (2d, 4H); 7.6 (2d, 4H); 5.4 (m, 2H); 5.2 (m, 2H); 3.4 (br m, 4H); 3.2 (br m, 4H); 1.2 (m, 12H).

Bisphosphonate Prodrug with 4-(p-methoxy-phenoxy)butyl (PMP) linker (as precursor to analogs with modified R groups at bridging methylene):

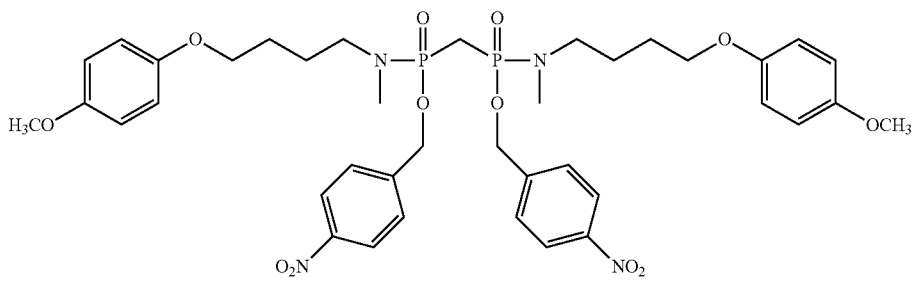 [SMILES: COc1ccc(OCCCCN(C)P(=O)(CP(=O)(OCc2ccc([N+](=O)[O-])cc2)N(C)CCCCOc2ccc(OC)cc2)OCc2ccc([N+](=O)[O-])cc2)cc1]

Methylenebis(phosphonic dichloride) (0.324 g, 1.3 mmol) and N-methyl-butyl-PMP (0.541 g, 2.6 mmol) were dissolved in $CH_2Cl_2$ (5.2 mL) and cooled to 0° C. with stirring under an Ar atmosphere. DIPEA (1.09 ml, 6.24 mmol) was added dropwise. The reaction mixture was allowed to warm to room temperature, and stiffing was continued for 2 h. Nitrobenzyl alcohol (0.697 g, 4.5 mmol) was added as a solid in one aliquot. In a separate flask under an Ar atmosphere, DMAP (0.159 mg, 0.1.3 mmol) was dissolved in $CH_2Cl_2$ (0.5 mL) and DIPEA (0.499 ml, 3.12 mmol) was added. The reaction mixture was stirred at room temperature for 2 h. The reaction was washed with saturated $NH_4Cl$. The organic layer was dried over sodium sulfate and concentrated under reduced pressure. Purification was accomplished by column chromatography (1:19, methanol/ethyl acetate). $^{31}P$ NMR ($CD_3OD$) δ 3.01 (s, 1); $^1H$ NMR ($CD_3OD$) δ 8.20 (2d, 4H); 7.59 (2d, 4H); 5.1 (2 m, 4H); 4.80 (2 s, 8H); 3.9 (2 s, 4H); 3.3 (s, 6H); 3.1 (2 m, 4H); 2.8 (t, 2H); 2.5 (2 s, 6H); 1.1 (m, 8H).

Synthesis of BP prodrugs bearing other substituents at the bridging methylene may be accessible from the PMP analog. The PMP protective group avoids any amine cyclization chemistry taking place as a result of deprotonation of the bridging C—H. The 4-(p-methoxyphenoxy)butyl group may be readily converted into the final 4-chlorobutyl group or other suitable substituent with a leaving group using chemistry known in the art.

Activity of Other Esters

A549 NSCLC cells were plated at $1.7 \times 10^4$ cells per well in flat bottom 12-well plates. Cells were dosed as described above. At 24, 48 or 72 hours following drug treatment, the media was collected, and the cells were washed with 200 μL PBS. Each well was trypsinized with 200 μL trypsin for 3-5 min. The trypsin reaction was quenched with an equal volume of media. All supernatants and washes were combined and spun at 1,500 rpm for 5 min. Supernatant was decanted, and the cells were resuspended in 200 μL media. The cells were diluted 1:1 in 0.04% trypan blue and counted using a cytometer. The absolute number of cells was determined at each drug concentration. The cell number for each concentration was converted to percent of control for each time point, and plotted using GraphPad Prism 4.0. The $EC_{50}$ was calculated as the concentration of drug that caused a 50% decrease in number of cells compared to control. The results shown in FIG. 13 are from a single experiment only.

Figure 13:
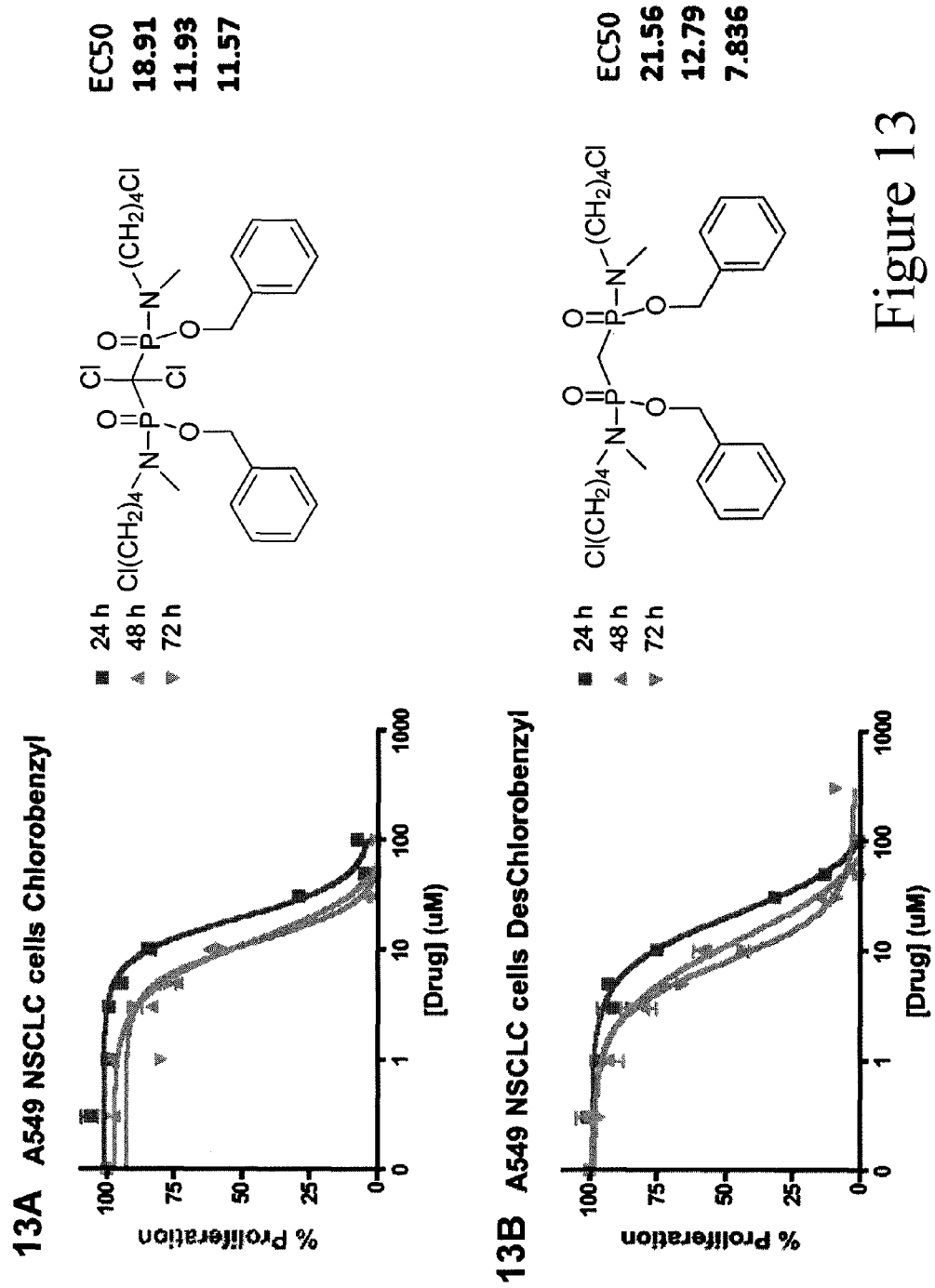
FIG. 13 shows the activity of various esters of bisphosphonamidate prodrugs of clodronate and bisphosphonate against NSCLC; benzyl ester prodrug of clodronate (FIG. 13A), benzyl ester prodrug of bisphosphonate (FIG. 13B), nitrophenethyl prodrug of clodronate (FIG. 13C), methyl ester prodrug of clodronate (FIG. 13D).

Results are shown in FIG. 13 and in the table below

|  | $IC_{50}$ 24 h | $IC_{50}$ 48 h | $IC_{50}$ 72 h |
|---|---|---|---|
| Chlorobenzyl, 13A | 18.9 μM | 11.9 μM | 11.6 μM |
| Deschlorobenzyl, 13B | 21.6 μM | 12.8 μM | 7.8 μM |
| Nitrophenethyl, 13C | 4.8 μM | 3.1 μM | 2.1 μM |
| Methoxy, 13D | 93.4 μM | 100 μM | 76.3 μM |

Activity comparison between Nitrophenethyl prodrug (shown in FIG. 13C) and bisphosphonate prodrug (13) using the trypan blue assay (discussed previously) is shown in FIGS. 13E and 13F and the table below.

|  | $EC_{50}$ 24 h | $EC_{50}$ 48 h | $EC_{50}$ 72 h |
|---|---|---|---|
| Clodronate Prodrug | n.d. | 19 ± 4 μM | 16 ± 1 μM |
| Nitrophenethyl, 13C | ~10 μM | 3.5 μM | 4.2 μM |
| Bisphosphonate Prodrug | n.d. | 24 ± 4 μM | 24 ± 4 |
| Bisphosphonate | n.d. | n.d. | n.d |
| Clodronate | n.d. | n.d. | n.d. |

Example 6

In vivo Tolerance Study of Clodronate Prodrug

I.V. Dosing (Tail Vein Injections)

Ten Balb/c mice were split into three groups: untreated, vehicle and clodronate prodrug. Untreated mice received no treatment or injection. The vehicle was 100 μL 10% cremaphor in ddH20 injected into the tale vein. 100 μL of 3 mM Clodronate Prodrug dissolved in 10% cremaphor in ddH20. (100 μL of 3 mM is about 14 mg/kg). Results are shown in the table below.

| | Mouse weight (g) | | | | | |
|---|---|---|---|---|---|---|
| ID # | Mar. 21, 2011 | Mar. 23, 2011 | Mar. 25, 2011 | Mar. 28, 2011 | Treatment | Δ in weight (g) |
| 795 | 15.5 | 15.8 | 16 | 16.2 | untreated | 0.7 |
| 796 | 17.2 | 17.7 | 18.3 | 18.5 | vehicle | 1.3 |
| 798 | 17.2 | 17.2 | 16.9 | 17.6 | vehicle | 0.4 |
| 799 | 17.1 | 17.2 | 17.2 | 17.2 | vehicle | 0.1 |

|  | Mouse weight (g) | | | | | |
| --- | --- | --- | --- | --- | --- | --- |
| ID # | Mar. 21, 2011 | Mar. 23, 2011 | Mar. 25, 2011 | Mar. 28, 2011 | Treatment | Δ in weight (g) |
| 797 | 16.9 | 17.3 | 16.8 | 17.8 | untreated | 0.9 |
| 777 | 14.5 | 16.4 | 16.8 | 17.2 | cloprodrug | 2.7 |
| 776 | 15.6 | 16.2 | 16.4 | 16.2 | cloprodrug | 0.6 |
| 790 | 17.3 | 18.5 | 19.1 | 19.2 | failed injection | 1.9 |
| 792 | 15.9 | 17.6 | 18.2 | 18.1 | cloprodrug | 2.2 |
| 789 | 14.6 | 16.5 | 16.6 | 16.3 | untreated | 1.7 |

Mouse 799 lost its ear tag on Mar. 28, 2011
Clodronate prodrug average weight gain after 7 days: 1.83
Vehicle average weight gain after 7 days: 0.6
Untreated average weight gain after 7 days: 1.1

There is no significant difference in weight between the three treatment groups. There was no unusual behavior observed.

Intraparitoneal Dosing Experiment:

Thirteen Balb/C mice were split into four groups; untreated, vehicle, dose 1 and dose 2. Untreated mice received no treatment or injection. The vehicle was 100 μL of corn oil. Mice receiving dose 1 received 100 μL of 30 mM clodronate prodrug dissolved in corn oil (2.17 mg/dose), which is about 110 mg/kg dose. Mice receiving dose 2 received 100 μL of 50 mM clodronate prodrug dissolved in corn oil (3.61 mg/dose), which is about a 200 mg/kg dose. Mice were dosed on Monday of each week for two weeks. The weights were measured for 4 consecutive days following dosing.

| Treatment | ID | Dose (mg/kg) | Wt (g) | | | | | Weight Δ (g) |
| --- | --- | --- | --- | --- | --- | --- | --- | --- |
| | | | Apr. 11, 2011 | Apr. 12, 2011 | Apr. 13, 2011 | Apr. 14, 2011 | Apr. 15, 2011 | |
| Vehicle | 867 | | 19.6 | 19.9 | 20.3 | 20.1 | 20.5 | 0.9 |
| | 868 | | | 19.6 | 19.6 | 19.7 | 20.03 | 0.73 |
| | 875 | | 20.1 | 20 | 20.7 | 20.3 | 20.7 | 0.6 |
| Untreated | 790 | | | 19.9 | 20.1 | 20.1 | 20.3 | 0.4 |
| | 797 | | | 18.9 | 19.7 | 19.5 | 19.3 | 0.4 |
| | 795 | | | 17.2 | 18.6 | 18.5 | 18.1 | 0.9 |
| | 872 | | | 18.3 | 19.1 | 18.8 | 18.9 | 0.6 |
| Dose 1 | 861 | 113.02 | 19.2 | 19.3 | 19.8 | 19.8 | 19.5 | 0.30 |
| | 869 | 118.58 | 18.3 | 18.1 | 18.8 | 18.7 | 19.01 | 0.71 |
| | 873 | 111.86 | 19.4 | 18.4 | 18.7 | 19.1 | 18.8 | −0.60 |
| Dose 2 | 870 | 193.05 | 18.7 | 17.8 | 19.07 | 19.03 | 18.7 | 0.00 |
| | 871 | 198.35 | 18.2 | 17.7 | 18.8 | 18.8 | 18.2 | 0.00 |
| | 874 | 189.01 | 19.1 | 18.2 | 18.8 | 19.1 | 19.6 | 0.50 |

| 2nd week of treatment, same Balb/c mice-Dose 2 on Apr. 18, 2011 follow weight for 1 week | | | | | | | | |
| --- | --- | --- | --- | --- | --- | --- | --- | --- |
| Treatment | ID | Dose (mg/kg) | Wt (g) | | | | | Weight Δ (g) |
| | | | Apr. 18, 2011 | Apr. 19, 2011 | Apr. 20, 2011 | Apr. 21, 2011 | Apr. 22, 2011 | |
| Vehicle | 867 | | 20.3 | 20.1 | 19.8 | 20.2 | 20 | −0.3 |
| | 868 | | 19.7 | 19.5 | 19.5 | 19.6 | 20.1 | 0.4 |
| | 875 | | 20.5 | 20.3 | 20 | 20.3 | 19.6 | −0.9 |
| | 797 | | 20.6 | 19.9 | 19.6 | 20.3 | 20.3 | 0.4 |
| Untreated | 790 | | 20.3 | 19.7 | 20 | 20.3 | 20.6 | 0.9 |
| | 795 | | 18.8 | 18.2 | 18.2 | 17.9 | 18.4 | 0.2 |
| | 872 | | 19 | 18.4 | 18.5 | 18.9 | 19 | 0.6 |
| Dose 1 | 861 | 112.44 | 19.3 | 19.3 | 19.4 | 19.1 | 19.3 | 0.00 |
| | 869 | 115.43 | 18.8 | 18.9 | 18.9 | 18.9 | 19.2 | 0.40 |
| | 873 | 117.93 | 18.4 | 18.3 | 18.4 | 18.6 | 18.3 | −0.10 |
| Dose 2 | 870 | 187.05 | 19.3 | 19.1 | 18.8 | 19 | 18.9 | −0.40 |
| | 871 | 189.01 | 19.1 | 19.3 | 19 | 19.4 | 19.5 | 0.40 |
| | 874 | 185.13 | 19.5 | 19.5 | 19 | 19.4 | 20 | 0.50 |

Note:
After two doses, there was no significant difference in weight between the four dosing groups.

Example 7

Cyclic Bisphosphonamidate Prodrugs

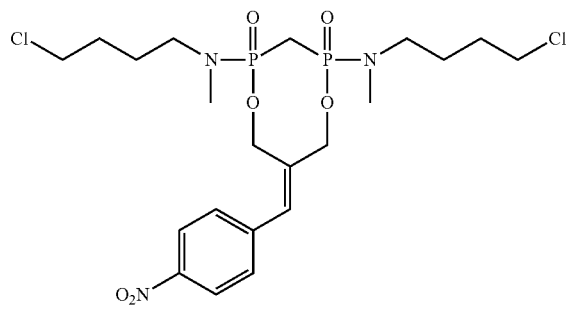 [SMILES: CN(CCCCCl)P1(=O)CP(=O)(N(C)CCCCCl)OCC(=Cc2ccc([N+](=O)[O-])cc2)CO1]

Methylenebis(phosphonic dichloride) (0.084 g, 0.340 mmol) and N-methyl-N-(4-chlorobutyl)amine hydrochloride (0.107 g, 0.68 mmol) were dissolved in $CH_2Cl_2$ (1.36 mL) and cooled to 0° C. with stiffing under an Ar atmosphere. DIPEA (0.284 mL, 1.63 mmol) was added dropwise. The reaction mixture was allowed to warm to room temperature, and stirring was continued for 2 h. After 2 h, 2.72 mL $CH_2Cl_2$ was added to the reaction mixtures. Nitrobenzylidene diol (0.071 g, 0.340 mmol) was added as a solid. In a separate flask under an Ar atmosphere, DMAP (0.0415 mg, 0.340 mmol) was dissolved in $CH_2Cl_2$ (0.1 mL) and DIPEA (0.142 ml, 0.815 mmol) was added. The reaction stirred at room temperature for 2 h. The reaction was washed with saturated $NH_4Cl$ and the organic layer was concentrated under reduced pressure. $^{31}P$ NMR (CDCl$_3$) δ 0.89 (d, 0.94); 0.91 (d, 1). $^1H$ NMR (CDCl$_3$) δ 8.1 (2d, 4H); 7.3 (2d, 4H); 6.5 (2d, 2H); 5.18 (2 m, 4H); 4.20 (2d, 4H); 2.9 (br m, 8H); 2.6 (m, 4H); 2.2 (m, 2H); 1.6 (2 m, 8H). ESI-MS; (m+1)=557.9.

Cyclized Diethylamine Bisphosphonate Model Compound:

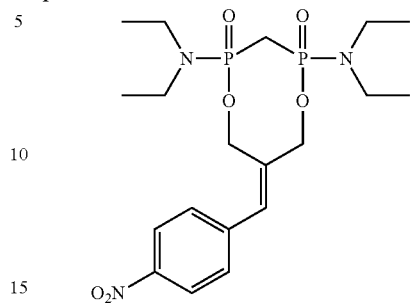

Methylenebis(phosphonic dichloride) (0.104 g, 0.416 mmol) and diethyl amine (0.061 g, 0.832 mmol) were dissolved in $CH_2Cl_2$ (1.66 mL) and cooled to 0° C. with stirring under an Ar atmosphere. DIPEA (0.174 mL, 0.998 mmol) was added dropwise. The reaction mixture was allowed to warm to room temperature, and stiffing was continued for 2 h. Nitrobenzylidene diol (0.087 g, 0.416 mmol) was added dissolved in 2.5 mL $CH_2Cl_2$. The diol was added to the reaction mixture. In a separate flask under an Ar atmosphere, DMAP (0.228 mg, 1.87 mmol) and DIPEA (0.0.174 mL, 0.998 mmol) were combined in $CH_2Cl_2$ (0.2 ml). The reaction mixture was stirred at room temperature for 2 h. The reaction was quenched with saturated $NH_4Cl$. The organic layer was separated and concentrated under reduced pressure. $^{31}P$ NMR (CDCl$_3$) δ −0.03 (m, 1). ESI-MS; (m+1) 460.1; (m+Na)=482.1

Synthesis of Cyclized Zoledronate Diester:

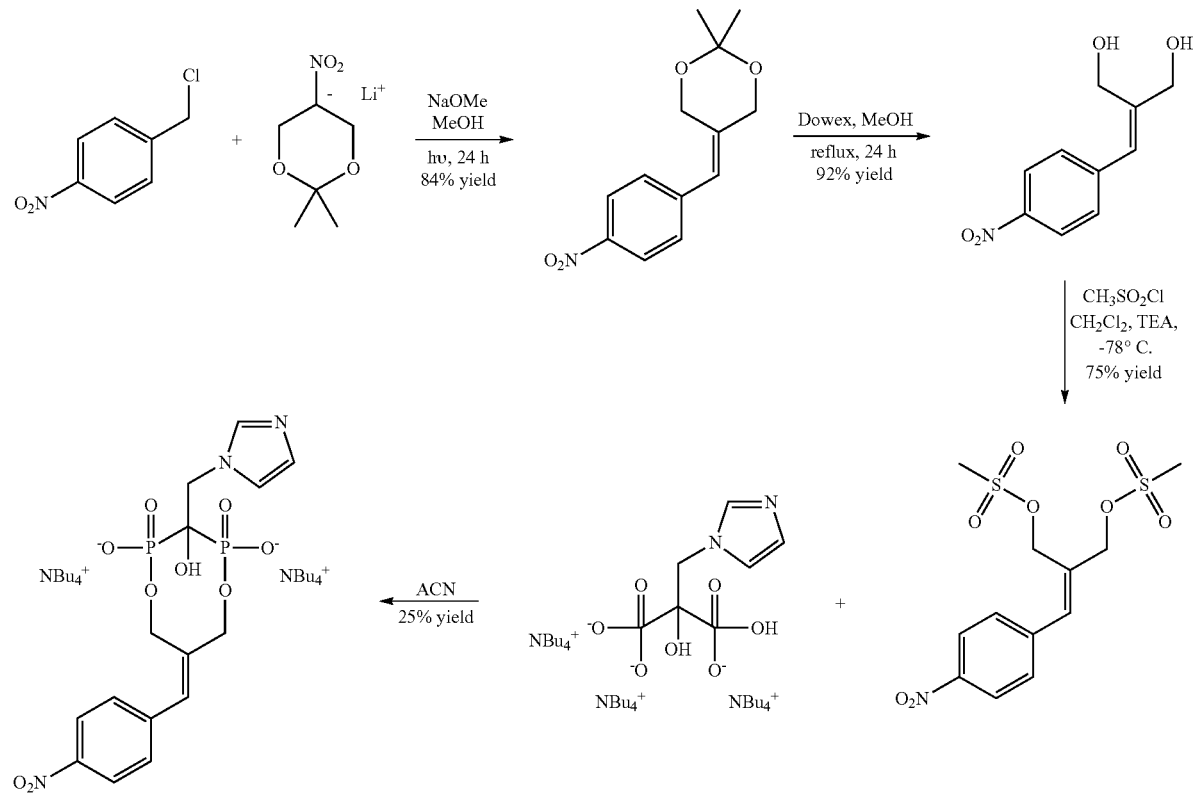

| Cell | | Zoledronic Acid (uM) | | Cyclized Zoldronate Intermediate (uM) | |
|---|---|---|---|---|---|
| Line | (hrs) | Normoxia | Hypoxia | Normoxia | Hypoxia |
| A549 | 48 | $IC_{50}$ = 98 μM | $IC_{50}$ = 350 μM | $IC_{50}$ = 416 μM | $IC_{50}$ = 919 μM |
|  | 72 | $IC_{50}$ = 45 μM | $IC_{50}$ = 205 μM | $IC_{50}$ = 534 μM | $IC_{50}$ = 1180 μM |
| H358 | 48 | $IC_{50}$ = 59 μM | $IC_{50}$ = 87 μM | $IC_{50}$ = 485 μM | $IC_{50}$ = 233 μM |
|  | 72 | $IC_{50}$ = 15 μM | $IC_{50}$ = 135 μM | $IC_{50}$ = 177 μM | $IC_{50}$ = 151 μM |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

We claim:

1. A compound having the formula

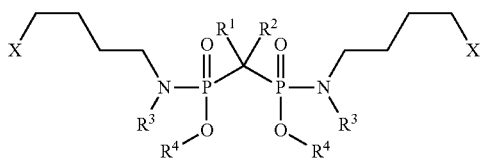

wherein

X is a leaving group;

$R^1$ and $R^2$ are the same or different and each is selected from the group consisting of H, halogen, alkyl, alkenyl, haloalkyl, aralkyl, heteroaralkyl, aryloxy, arylthio, aminoalkyl, hydroxylalkyl, alkoxyalkyl, hydroxyl, amino, alkylamino, arylamino, heteroarylamino, alkylaminoalkyl, arylaminoalkyl, heteroarylaminoalkyl, alkoxy, alkoxyalkyl, alkylthio, O-acyl, N-acyl, and S-acyl, or $R^1$ is H, halogen, alkyl, alkenyl, haloalkyl, aralkyl, heteroaralkyl, aryloxy, arylthio, aminoalkyl, hydroxylalkyl, or alkoxyalkyl and $R^2$ is H, halogen, alkyl, alkenyl, haloalkyl, hydroxyl, amino, alkoxy, alkylthio, O-acyl, N-acyl, or S-acyl;

each $R^3$ is the same or different and is alkyl, hydroxyl, or alkoxy;

each $R^4$ is the same or different and is alkyl, aralkyl, heteroaralkyl or

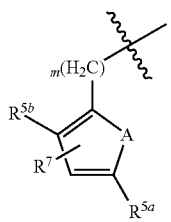

where m is 1, 2, 3, 4, 5, or 6; one of $R^{5a}$ and $R^{5b}$ is H or $R^7$ and the other of $R^{5a}$ and $R^{5b}$ is H, halogen, nitro, alkyl, haloalkyl, hydroxyl, amino, alkoxy, alkylthio, O-acyl, N-acyl, S-acyl, or N—O-acyl; and $R^7$ represents one or more substituents up to the total number of available positions and is hydrogen, halogen, alkyl, haloalkyl, or alkoxy; A is —O—, —S—, —N($R^8$)—, —C=C—; —C=N—, or N=C and $R^8$ is hydrogen or alkyl; or both $R^4$ taken together are

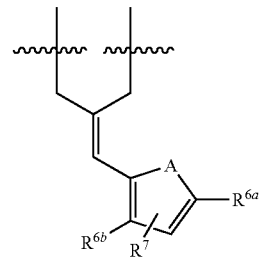

wherein $R^7$ and A are defined as above and one of $R^{6a}$ and $R^{6b}$ is H or $R^7$ and the other of $R^{6a}$ and $R^{6b}$ is nitro, O-acyl, N-acyl, N—O-acyl or —N=N—$R^9$ where $R^9$ is alkyl or aryl;

and pharmaceutically acceptable salts thereof.

2. The compound of claim 1, where $R^1$ is hydrogen, alkyl, halogen, aminoalkyl, thioaryl, or heteroalkyl.

3. The compound of claim 1, where $R^2$ is H, halogen, or hydroxyl.

4. The compound of claim 1, where $R^1$ and $R^2$ are H.

5. The compound of claim 1, where $R^1$ and $R^2$ are Cl.

6. The compound of claim 1, where $R^1$ is heteroaralkyl or aminoalkyl, and $R^2$ is hydroxyl.

7. The compound of claim 1, where $R^3$ is alkyl.

8. The compound of claim 1, where $R^4$ is alkyl or aralkyl.

9. The compound of claim 1, where X is Cl.

10. The compound of claim 1, having the formula

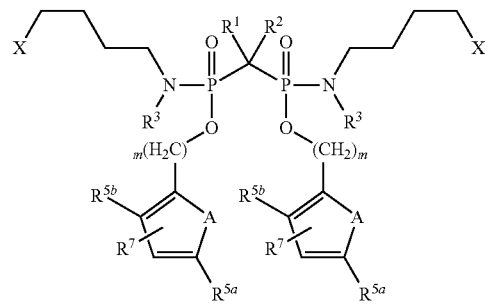

wherein $R^1$ is H, halogen, alkyl, haloalkyl, aralkyl, heteroaralkyl, aryloxy, arylthio, aminoalkyl, hydroxylalkyl, alkoxyalkyl;

$R^2$ is H, halogen, alkyl, haloalkyl, hydroxyl, amino, alkoxy, alkylthio, O-acyl, N-acyl, or S-acyl.

11. The compound of claim 10, where $R^{5a}$ or $R^{5b}$ are hydrogen or nitro.

12. The compound of claim 10, where A is —C=C—.

13. The compound of claim 10, where $R^1$ is hydrogen, alkyl, halogen, aminoalkyl, thioaryl, heteroalkyl.

14. The compound of claim 10, where $R^2$ is H, halogen, or hydroxyl.

15. The compound of claim 10, where $R^1$ and $R^2$ are H.

16. The compound of claim 10, where $R^1$ and $R^2$ are Cl.

17. The compound of claim 10, where $R^1$ is heteroaralkyl or aminoalkyl, and $R^2$ is hydroxyl.

18. The compound of claim 10, where $R^3$ is alkyl.

19. The compound of claim 10, where X is Cl.

20. The compound of claim 6, having the structure

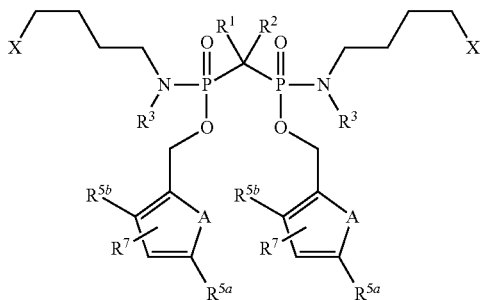

wherein one of $R^{5a}$ and $R^{5b}$ is H or $R^7$ and the other of $R^{5a}$ and $R^{5b}$ is nitro, O-acyl, N-acyl, or N—O-acyl.

21. The compound of claim 20, where $R^{5a}$ is nitro and $R^{5b}$ is H or $R^7$.

22. The compound of claim 20, where $R^1$ is hydrogen, alkyl, halogen, aminoalkyl, thioaryl, heteroaralkyl.

23. The compound of claim 20, where $R^2$ is H, halogen, or hydroxyl.

24. The compound of claim 20, where $R^1$ and $R^2$ are H.

25. The compound of claim 20, where $R^1$ and $R^2$ are Cl.

26. The compound of claim 20, where $R^1$ is heteroaralkyl or aminoalkyl, and $R^2$ is hydroxyl.

27. The compound of claim 20, where $R^3$ is alkyl.

28. The compound of claim 20, where A is —C═C—.

29. The compound of claim 20, where X is Cl.

30. The compound of claim 1, having the structure

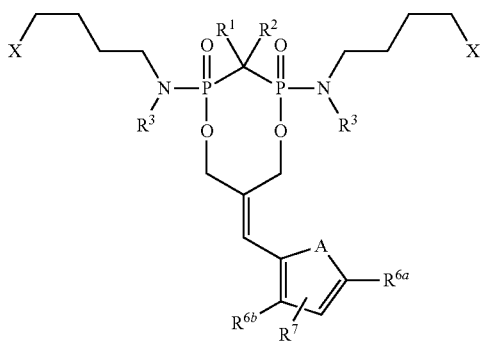

wherein
$R^1$ is H, halogen, alkyl, haloalkyl, aralkyl, heteroaralkyl, aryloxy, arylthio, aminoalkyl, hydroxylalkyl, alkoxyalkyl; and
$R^2$ is H, halogen, alkyl, haloalkyl, hydroxyl, amino, alkoxy, alkylthio, O-acyl, N-acyl, or S-acyl.

31. The compound of claim 30, where $R^{6a}$ is nitro and $R^{6b}$ is H or $R^7$.

32. The compound of claim 30, where $R^1$ is hydrogen, alkyl, halogen, aminoalkyl, thioaryl, heteroaralkyl.

33. The compound of claim 30, where $R^2$ is H, halogen, or hydroxyl.

34. The compound of claim 30, where $R^1$ and $R^2$ are H.

35. The compound of claim 30, where $R^1$ and $R^2$ are Cl.

36. The compound of claim 30, where $R^1$ is heteroaralkyl or aminoalkyl, and $R^2$ is hydroxyl.

37. The compound of claim 30, where $R^3$ is alkyl.

38. The compound of claim 30, where A is —C═C—.

39. The compound of claim 30, where X is Cl.

40. A pharmaceutical composition comprising a compound of claim 1.

41. A method of treating a disease comprising administering to a subject in need of treatment a therapeutically effective amount of the compound of claim 1, wherein the disease is selected from the group consisting of hypercalcemia, osteoporosis, malignant bone disease, and combinations.

42. A method of treating a hyperproliferative disorder comprising administering to a subject in need of treatment a therapeutically effective amount of the compound of claim 1,
wherein the hyperproliferative disorder is selected from the group consisting of non-small cell lung cancer, colon cancer, leukemia, CNS cancer, melanoma, ovarian cancer, renal cancer, prostate cancer, breast cancer, and combinations.

43. A method of treating a parasitical infection comprising administering to a subject in need of treatment a therapeutically effective amount of the compound of claim 1,
wherein the parasitical infection is selected from the group consisting of infection by *plasmodium falciparum*, infection by *trypanosoma brucei brucei*, and combinations.

44. A method of treating an infection by a parasite comprising administering to a subject in need of treatment a therapeutically effective amount of the compound of claim 1,
wherein the parasite is selected from the group consisting of a *plasmodium* parasite, a *trypanosoma* parasite, and combinations.

45. A method of treating an infection by a parasite comprising administering to a subject in need of treatment a therapeutically effective amount of the compound of claim 1,
wherein the parasite is selected from the group consisting of *trypanosoma cruzi, trypanosoma gondii*, and combinations.

* * * * *